(12) United States Patent
Durette et al.

(10) Patent No.: US 6,645,939 B1
(45) Date of Patent: Nov. 11, 2003

(54) SUBSTITUTED β-ALANINE DERIVATIVES AS CELL ADHESION INHIBITORS

(75) Inventors: Philippe L. Durette, New Providence, NJ (US); William K. Hagmann, Westfield, NJ (US); Ihor E. Kopka, Warren, NJ (US); Malcolm MacCoss, Freehold, NJ (US); Sander G. Mills, Scotch Plains, NJ (US); Richard A. Mumford, Red Bank, NJ (US); Plato A. Magriotis, Scotch Plains, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/317,789

(22) Filed: May 24, 1999

Related U.S. Application Data

(63) Continuation-in-part of application No. 09/198,680, filed on Nov. 24, 1998, now abandoned.
(60) Provisional application No. 60/066,484, filed on Nov. 24, 1997.

(51) Int. Cl.$^7$ ................................................. C07K 5/06
(52) U.S. Cl. ........................... 514/19; 514/18; 530/331; 548/535
(58) Field of Search ....................... 514/18, 19; 530/331

(56) References Cited

U.S. PATENT DOCUMENTS

| 5,439,930 A | 8/1995 | Seredenin et al. | 514/423 |
|---|---|---|---|
| 5,510,332 A | 4/1996 | Korgan et al. | 514/14 |
| 5,580,855 A | * 12/1996 | Ferreira | 514/18 |
| 5,688,913 A | * 11/1997 | Arrhenius | 530/330 |

FOREIGN PATENT DOCUMENTS

| DE | 44 45 5000 | 6/1996 |
|---|---|---|
| EP | 343 911 | 11/1989 |
| EP | 618 223 | 10/1994 |
| GB | 2 292 149 | 2/1996 |
| WO | WO 95/15973 | 6/1995 |
| WO | WO 95/35308 | 12/1995 |
| WO | WO 96/01644 | 1/1996 |
| WO | WO 96/06108 | 2/1996 |
| WO | WO 96/20216 | 7/1996 |
| WO | WO 96/22966 | 8/1996 |
| WO | WO 96/31206 | 10/1996 |
| WO | WO 96/40781 | 12/1996 |
| WO | WO 97/02289 | 1/1997 |
| WO | WO 97/03094 | 1/1997 |
| WO | WO 97/20856 | 6/1997 |
| WO | WO 98/04913 | 6/1998 |
| WO | WO 98/47523 | 10/1998 |
| WO | WO 98/53814 | 12/1998 |
| WO | WO 98/53817 | 12/1998 |
| WO | WO 98/53818 | 12/1998 |
| WO | WO 98/54207 | 12/1998 |
| WO | WO 99/06432 | 2/1999 |
| WO | WO 99/06437 | 2/1999 |
| WO | WO 99/61421 | 12/1999 |

OTHER PUBLICATIONS

Dutta Journal of Peptide Science 6, 321–341, 2000.*
Komoriya, Akira J. Biol. Chem. 266(23), 15075–9, 1991.*
Haworth, Duncan Br. J. Pharmacol. 126(8), 1751–1760, 1999.*
Haubner J Am Chem Soc 118, 7881, 1996.*
Yang Y European Journal of Immunology 28 (3) 995–1004, 1998.*
Smith, Emil, L., et al.—Chemical Abstracts 52:21196.
Halpern, Berthold, et al.—Chemical Abstracts 65:5524f.
Nagano, Masanobu, et al.—Chemical Abstracts 127:66223.
Takasugi, Hisashi, et al.—Chemical Abstracts 123:285545.
Yamamoto, Osamu, et al.—Chemical Abstracts 131:310838.
Fernandez–Megia, Eduardo, et al.—J. Org. Chem., Vol. 59 (25) 7643–52, 1994.
Reshetova, O.S., et al.—Chemical Abstracts 106:210288.
Schroff, Hitesh N., et al. Bio Organic & Medicinal Chemistry Letters, Vol. 6, No. 21, pp. 2495–2500 (1996).
Jackson, David Y. et al. Med. Chem., 40 pp. 3359–3368 (1997).

* cited by examiner

*Primary Examiner*—Christopher S. F. Low
*Assistant Examiner*—David Lukton
(74) *Attorney, Agent, or Firm*—Mollie M. Yang; David L. Rose

(57) ABSTRACT

β-Alanine derivatives of Formula I are antagonists of VLA-4 and/or $\alpha_4\beta_7$, and as such are useful in the inhibition or prevention of cell adhesion and cell-adhesion mediated pathologies. These compounds may be formulated into pharmaceutical compositions and are suitable for use in the treatment of asthma, allergies, inflammation, multiple sclerosis, and other inflammatory and autoimmune disorders.

7 Claims, No Drawings

US 6,645,939 B1

SUBSTITUTED β-ALANINE DERIVATIVES AS CELL ADHESION INHIBITORS

CROSS REFERENCE TO RELATED APPLICATIONS

This application is based on, and claims priority from, U.S. provisional application No. 60/066,484 filed Nov. 24, 1997, and is a continuation-in-part of U.S. patent application Ser. No. 09/198,680 filed Nov. 24, 1998, now abandoned which are hereby incorporated by reference in their entirety.

BACKGROUND OF THE INVENTION

The present invention relates to novel substituted β-alanine derivatives which are useful for the inhibition and prevention of leukocyte adhesion and leukocyte adhesion-mediated pathologies. This invention also relates to compositions containing such compounds and methods of treatment using such compounds.

Many physiological processes require that cells come into close contact with other cells and/or extracellular matrix. Such adhesion events may be required for cell activation, migration, proliferation and differentiation. Cell-cell and cell-matrix interactions are mediated through several families of cell adhesion molecules (CAMs) including the selectins, integrins, cadherins and immunoglobulins. CAMs play an essential role in both normal and pathophysiological processes. Therefore, the targetting of specific and relevant CAMs in certain disease conditions without interfering with normal cellular functions is essential for an effective and safe therapeutic agent that inhibits cell-cell and cell-matrix interactions.

The integrin superfamily is made up of structurally and functionally related glycoproteins consisting of α and β heterodimeric, transmembrane receptor molecules found in various combinations on nearly every mammalian cell type. (for reviews see: E. C. Butcher, Cell, 67, 1033 (1991); T. A. Springer, Cell, 76, 301 (1994); D. Cox et al., "The Pharmacology of the Integrins." Medicinal Research Rev. 14, 195 (1994) and V. W. Engleman et al., "Cell Adhesion Integrins as Pharmaceutical Targets." in Ann. Repts. in Medicinal Chemistry, Vol. 31, J. A.

Bristol, Ed.; Acad. Press, N.Y., 1996, p. 191).

VLA-4 ("very late antigen-4"; CD49d/CD29; or $\alpha_4\beta_1$) is an integrin expressed on all leukocytes, except platelets and mature neutrophils, including dendritic cells and macrophage-like cells and is a key mediator of the cell-cell and cell-matrix interactions of of these cell types (see M. E. Hemler, "VLA Proteins in the Integrin Family: Structures, Functions, and Their Role on Leukocytes." Ann. Rev. Immunol. 8, 365 (1990)). The ligands for VLA-4 include vascular cell adhesion molecule-1 (VCAM-1) and the CS-1 domain of fibronectin (FN). VCAM-1 is a member of the Ig superfamily and is expressed in vivo on endothelial cells at sites of inflammation. (See R. Lobb et al. "Vascular Cell Adhesion Molecule 1." in Cellular and Molecular Mechanisms of Inflammation, C. G. Cochrane and M. A. Gimbrone, Eds.; Acad. Press, San Diego, 1993, p. 151,) VCAM-1 is produced by vascular endothelial cells in response to pro-inflammatory cytokines (See A. J. H. Gearing and W. Newman, "Circulating adhesion molecules in disease.", Immunol. Today, 14, 506 (1993). The CS-1 domain is a 25 amino acid sequence that arises by alternative splicing within a region of fibronectin. (For a review, see R. O. Hynes "Fibronectins.", Springer-Velag, N.Y., 1990.) A role for VLA-4/CS-1 interactions in inflammatory conditions has been proposed (see M. J. Elices, "The integrin $\alpha_4\beta_1$ (VLA-4) as a therapeutic target" in Cell Adhesion and Human Disease, Ciba Found. Symp., John Wiley & Sons, NY, 1995, p. 79).

$\alpha_4\beta_7$ (also referred to as LPAM-1 and $\alpha_4 \beta_p$) is an integrin expressed on leukocytes and is a key mediator of leukocyte trafficking and homing in the gastrointestinal tract (see C. M. Parker et al., Proc. Natl. Acad. Sci. USA, 89, 1924 (1992)). The ligands for $\alpha_4 \beta_7$ include mucosal addressing cell adhesion molecule-1 (MadCAM-1) and, upon activation of $\alpha_4 \beta_7$, VAM-1 and fibronectin (Fn). MadCAM-1 is a member of the Ig superfamily and is expressed in vivo on endothelial cells of gut-associated mucosal tissues of the small and large intestine ("Peyer's Patches") and lactating mammary glands. (See M. J. Briskin et al., Nature, 363, 461 (1993); A. Hamann et al., J. Immunol., 152, 3282 (1994)). MadCAM-1 can be induced in vitro by proinflammatory stimuli (See E. E. Sikorski et al. J. Immunol., 151, 5239 (1993)). MadCAM-1 is selectively expressed at sites of lymphocyte extravasation and specifically binds to the integrin, $\alpha_4\beta_7$.

The $\alpha_4\beta_1$ integrin is found on airway smooth muscle cells, non-intestinal epithelial cells (see Palmer et al., J. Cell Biol., 123, 1289 (1993)), and neutrophils, and, less so, on hepatocytes and basal keratinocytes (see Yokosaki et al., J. Biol. Chem., 269,24144 (1994)). Neutrophils, in particular, are intimately involved in acute inflammatory repsonses. Attenuation of neutrophil involvement and/or activation would have the effect of lessening the inflammation. Thus, inhibition of α9 β1 binding to its respective ligands would be expected to have a positive effect in the treatment of acute inflammatory conditions.

Neutralizing anti-$\alpha_4$ antibodies or blocking peptides that inhibit the interaction between VLA-4 and/or $\alpha_4\beta_7$ and their ligands have proven efficacious both prophylactically and therapeutically in several animal models of disease, including i) experimental allergic encephalomyelitis, a model of neuronal demyelination resembling multiple sclerosis (for example, see T. Yednock et al., "Prevention of experimental autoimmune encephalomyelitis by antibodies against $\alpha_4\beta_1$ integrin." Nature, 356, 63 (1993) and E. Keszthelyi et al., "Evidence for a prolonged role of α4 integrin throughout active experimental allergic encephalomyelitis." Neurology, 47, 1053 (1996)); ii) bronchial hyperresponsiveness in sheep and guinea pigs as models for the various phases of asthma (for example, see W. M. Abraham et al., "$\alpha_4$-Integrins mediate antigen-induced late bronchial responses and prolonged airway hyperresponsiveness in sheep." J. Clin. Invest. 93, 776 (1993) and A. A. Y. Milne and P. P. Piper, "Role of VLA-4 integrin in leucocyte recruitment and bronchial hyperresponsiveness in the gunea-pig." Eur. J. Pharmacol., 282, 243 (1995)); iii) adjuvant-induced arthritis in rats as a model of inflammatory arthritis (see C. Barbadillo et al., "Anti-VLA-4 mAb prevents adjuvant arthritis in Lewis rats." Arthr. Rheuma. (Suppl.), 36 95 (1993) and D. Seiffge, "Protective effects of monoclonal antibody to VLA-4 on leukocyte adhesion and course of disease in adjuvant arthritis in rats." J. Rheumatol., 23, 12 (1996)); iv) adoptive autoimmune diabetes in the NOD mouse (see J. L. Baron et al., "The pathogenesis of adoptive murine autoimmune diabetes requires an interaction between $\alpha_4$-integrins and vascular cell adhesion molecule-1.", J. Clin. Invest., 93, 1700 (1994), A. Jakubowski et al., "Vascular cell adhesion molecule-Ig fusion protein selectively targets activated $\alpha_4$-integrin receptors in vivo: Inhibition of autoimmune diabetes in an adoptive transfer model in nonobese diabetic mice." J. Immunol., 155, 938 (1995), and X. D. Yang et al., "Involvement of beta 7 integrin and mucosal addressin cell adhesion molecule-1 (MadCAM-1) in the development of diabetes in nonobese diabetic mice", Diabetes, 46, 1542 (1997)); v) cardiac allograft survival in mice as a model of organ transplantation (see M. Isobe et al., "Effect of anti-VCAM-1 and anti-VLA-4 monoclonal antibodies on cardiac allograft survival and response to soluble antigens in mice.", Tranplant. Proc., 26, 867 (1994) and S. Molossi et al., "Blockade of very late antigen-4 integrin binding to fibronectin with connecting segment-1 peptide reduces accelerated coronary arteripathy in rabbit cardiac allografts." J. Clin Invest., 95, 2601 (1995)); vi) spontaneous chronic colitis in cotton-top tamarins which resembles human ulcerative colitis, a form of inflammatory bowel disease (see D. K. Podolsky et al., "Attenuation of colitis in the Cottoh-top tamarin by anti-$\alpha_4$ integrin monoclonal antibody.", J. Clin. Invest., 92, 372 (1993)); vii) contact hypersensitivity models as a model for skin allergic reactions (see T. A. Ferguson and T. S. Kupper, "Antigen-independent processes in antigen-specific immunity.", J. Immunol., 150, 1172 (1993) and P. L. Chisholm et al., "Monoclonal antibodies to the integrin $\alpha$-4 subunit inhibit the murine contact hypersensitivity response." Eur. J. Immunol., 23, 682 (1993)); viii) acute neurotoxic nephritis (see M. S. Mulligan et al., "Requirements for leukocyte adhesion molecules in nephrotoxic nephritis.", J. Clin. Invest., 91, 577 (1993)); ix) tumor metastasis (for examples, see M. Edward, "Integrins and other adhesion molecules involved in melanocytic tumor progression.", Curr. Opin. Oncol., 7, 185 (1995)); x) experimental autoimmune thyroiditis (see R. W. McMurray et al., "The role of $\alpha$4 integrin and intercellular adhesion molecule-1 (ICAM-1) in murine experimental autoimmune thyroiditis." Autoimmunity, 23, 9 (1996); and xi) ischemic tissue damage following arterial occlusion in rats (see F. Squadrito et al., "Leukocyte integrin very late antigen-4/vascular cell adhesion molecule-1 adhesion pathway in splanchnic artery occlusion shock." Eur. J. Pharmacol., 318, 153 (1996; xii) inhibition of TH2 T-cell cytokine production including IL-4 and IL-5 by VLA-4 antibodies which would attenuate allergic responses (J.Clinical Investigation 100, 3083 (1997). The primary mechanism of action of such antibodies appears to be the inhibition of lymphocyte and monocyte interactions with CAMs associated with components of the extracellular matrix, thereby limiting leukocyte migration to extravascular sites of injury or inflammation and/or limiting the priming and/or activation of leukocytes.

There is additional evidence supporting a possible role for VLA-4 interactions in other diseases, including rheumatoid arthritis; various melanomas, carcinomas, and sarcomas; inflammatory lung disorders; acute respiratory distress syndrome (ARDS); atherosclerotic plaque formation; restenosis; uveitis and circulatory shock (for examples, see A. A. Postigo et al., "The $\alpha_4\beta_1$ VCAM-1 adhesion pathway in physiology and disease.", Res. Immunol., 144, 723 (1994) and J.-X. Gao and A. C. Issekutz, "Expression of VCAM-1 and VLA-4 dependent T-lymphocyte adhesion to dermal fibroblasts stimulated with proinflammatory cytokines." Immunol. 89, 375 (1996)).

At present, there is a humanized monoclonal antibody (Antegren® Athena Neurosciences/Elan ) against VLA-4 in clinical development for the treatment of "flares" associated with multiple sclerosis and a humanized monoclonal antibody (ACT-1®/LDP-02 LeukoSite) against $\alpha_4\beta_7$ in clinical development for the treatment of inflammatory bowel disease. Several peptidyl antagonists of VLA-4 have been described (D. Y. Jackson et al., "Potent $\alpha$4$\beta$1 peptide antagonists as potential anti-inflammatory agents", J. Med. Chem., 40, 3359 (1997); H. N. Shroff et al., "Small peptide inhibitors of $\alpha_4\beta_7$ mediated MadCAM-1 adhesion to lymphocytes", Bioorg. Med. Chem. Lett., 6, 2495 (1996); U.S. Pat. No. 5,510,332, WO97/03094, WO97/02289, WO96/40781, WO96/22966, WP96/20216, WO96/01644, WO96/06108, WO95/15973). There is one report of non-peptidyl inhibitors of the ligands for $\alpha_4$-integrins (WO96/31206). There still remains a need for low molecular weight, specific inhibitors of VLA-4- and $\alpha$4$\beta$7-dependent cell adhesion that have improved pharmacokinetic and pharmacodynamic properties such as oral bioavailability and significant duration of action. Such compounds would prove to be useful for the treatment, prevention or suppression of various pathologies mediated by VLA-4 and $\alpha_4\beta_7$ binding and cell adhesion and activation.

SUMMARY OF THE INVENTION

The compounds of the present invention are antagonists of the VLA-4 integrin ("very late antigen-4"; CD49d/CD29; or $\alpha_4\beta_1$), the $\alpha$4$\beta$7 integrin (LPAM-1 and $\alpha_4\beta_p$), and/or the $\alpha_9\beta_1$ integrin, thereby blocking the binding of VLA-4 to its various ligands, such as VCAM-1 and regions of fibronectin, $\alpha_4\beta_7$ to its various ligands, such as MadCAM-1, VAM-1 and fibronectin, and /or $\alpha_9\beta$1 to its various ligands, such as tenascin, osteopontin and VCAM-1. Thus, these antagonists are useful in inhibiting cell adhesion processes including cell activation, migration, proliferation and differentiation. These antagonists are useful in the treatment, prevention and suppression of diseases mediated by VLA-4-, $\alpha$4$\beta$7-, and/or $\alpha$9$\beta$1-binding and cell adhesion and activation, such as AIDS-related dementia, allergic conjunctivitis, allergic rhinitis, Alzheimer's disease, aortic stenosis, asthma, atherosclerosis, autologous bone marrow transplantation, certain types of toxic and immune-based nephritis, contact dermal hypersensitivity, inflammatory bowel disease including ulcerative colitis and Crohn's disease, inflammatory lung diseases, inflammatory sequelae of viral infections, meningitis, multiple sclerosis, myocarditis, organ transplantation, psoriasis, restenosis, retinitis, rheumatoid arthritis, septic arthritis, stroke, tumor metastasis, type I diabetes, vascular occlusion following angioplasty.

DETAILED DESCRIPTION OF THE INVENTION

The present invention provides novel compounds of Formula I

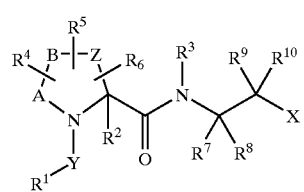

or a pharmaceutically acceptable salt thereof wherein:
  A and Z are independently selected from —C—, —C=C— and —C—C—;
  B is selected from the group consisting of
    1) a bond,
    2) —C—
    3) —C—C—,
    3) —C=C—,
    4) a heteroatom selected from the group consisting of nitrogen, oxygen, and sulfur, 5) —S(O)$_m$—, and
  6) N—Y—R$^1$;
X is 1) —C(O)OR$^d$,
  2) —P(O)(OR$^d$)(OR$^e$)
  3) —P(O)(R$^d$)(OR$^e$)
  4) —S(O)$_m$OR$^d$,
  5) —S(O)$_m$NR$^d$R$^h$;
  6) —C(O)NR$^d$R$^h$, or
  7) —5-tetrazolyl;
Y is 1) —C(O)—,
  2) —O—C(O)—,
  3) —NR$^e$—C(O)—,
  4) —S(O)$_2$—,
  5) —P(O)(OR$^4$) or
  6) C(O)C(O);
R$^1$ is 1) C$_{1-10}$alkyl,
  2) C$_2$10alkenyl,
  3) C$_{2-10}$alkynyl,
  4) Cy,
  5) Cy-C$_{1-10}$aryl,
  6) Cy-C$_{2-10}$alkenyl,
  7) Cy-C$_{2-10}$alkynyl,
wherein alkyl, alkenyl, and alkynyl are optionally substituted with one to four substituents independently selected from R$^a$; and Cy is optionally substituted with one to four substituents independently selected from R$^b$;
R$^2$ is 1) hydrogen,
  2) C$_{1-10}$alkyl,
  3) C$_{2-10}$alkenyl,
  4) C$_{2-10}$alkynyl,
  5) aryl,
  6) aryl—C$_{1-10}$alkyl,
  7) heteroaryl,
  8) heteroaryl-C$_{1-10}$alkyl,
wherein alkyl, alkenyl, and alkynyl are optionally substituted with one to four substituents independently selected from R$^a$; and aryl and heteroaryl optionally substituted with one to four substituents independently selected from R$^b$;
R$^3$ is 1) hydrogen,
  2) C$_{1-10}$alkyl,
  3) Cy, or
  4) Cy-C$_{1-10}$alkyl,
wherein alkyl is optionally substituted with one to four substituents independently selected from R$^a$; and Cy is optionally substituted with one to four substituents independently selected from R$^b$;
R$^4$, R$^5$ and R$^6$ are each independently selected from the group consisting of
  1) hydrogen, or
  2) a group selected from R$^b$; or
two of R$^4$, R$^5$ and R$^6$ and the atom to which both are attached, or two of R$^4$, R$^5$ and R$^6$ and the two adjacent atoms to which they are attached, together form a 5–7 membered saturated or unsaturated monocyclic ring containing zero to three heteroatoms selected from N, O or S,
R$^7$ and R$^8$ are independently selected from the group consisting of:
  1) hydrogen,
  2) C$_{1-10}$alkyl,
  3) C$_{2-10}$alkenyl,
  4) C$_{1-10}$alkynyl,
  5) Cy-(Cy$^1$)$_p$,
  6) Cy-(Cy$^1$)$_p$-C$_{1-10}$alkyl,
  7) Cy-(Cy$^1$)$_p$-C$_{2-10}$alkenyl,
  8) Cy-(Cy$^1$)$_p$-C$_{2-10}$alkynyl,
  9) CO$_2$R$^d$ alkyl, alkenyl and alkynyl are optionally substituted with one to four substituents independently selected from R$^a$; and Cy and Cy$^1$ are optionally substituted with one to four substituents independently selected from R$^b$; or
  R7, R$^8$ and the carbon to which they are attached form a 4–10 membered monocyclic ring optionally containing 0–2 heteroatoms selected from N, O and S;
R$^9$ is 1) hydrogen,
  2) C$_{1-10}$alkyl,
  3 C$_{2-10}$oalkenyl,
  4) C$_{2-10}$alkynyl,
  5) Cy,
  6) Cy-C$_{1-10}$alkyl,
  7) Cy-C$_{2-10}$alkenyl,
  8) Cy-C$_{2-10}$alkynyl,
  9) C$_{1-10}$alkoxy,
  10) Cy-O,
  11) Cy-C$_{1-10}$alkoxy,
  12) —S(O)mR$^d$,
  13) —SR$^d$,
  14) —S(O)$_2$OR$^d$,
  15) —S(O)$_m$NR$^d$R$^e$,
  16) hydroxy,
  17) —NR$^d$R$^e$,
  18) —O(CR$^f$R$^g$)$_n$R$^d$R$^e$,
  19) —OC(O)R$^d$,
  20) —CN,
  21) —C(O)NR$^d$R$^e$,
  22) —NR$^d$C(O)R$^e$,
  23) —OC(O)NR$^d$R$^e$,
  24) —NR$^d$C(O)OR$^e$, and
  25) —NR$^d$C(O)NR$^d$R$^e$,
wherein alkyl, alkenyl and alkynyl are optionally substituted with one to four substituents selected from R$^a$, and Cy is optionally substituted with one to four substituents independently selected from R$^b$; or
R$^{10}$ is 1) hydrogen,
  2) C$_{1-10}$alkyl,
  3) C$_{2-10}$alkenyl,
  4) C$_{2-10}$alkynyl,
  5) aryl,
  6) aryl-C$_{1-10}$alkyl,
  7) heteroaryl,
  8) heteroaryl-C$_{1-10}$alkyl,
wherein alkyl, alkenyl and alkynyl are optionally substituted with one to four substituents selected from R$^a$, and aryl and heteroaryl are optionally substituted with one to four substituents independently selected from R$^b$;
R$^a$ is 1) —CF$_3$;
  2) —OR$^d$,
  3) —NO$_2$,
  4) halogen
  5) —S(O)$_m$R$^d$,
  6) —SR$^d$
  7) —S(O)$_2$OR$^d$,
  8) —S(O)$_m$NR$^d$R$^e$,
  9) —NR$^d$R$^e$,
  10) —O(CR$^f$R$^g$)$_n$NR$^d$R$^e$,
  11) —C(O)R$^d$,
  12) —CO$_2$R$^e$,
  13) —CO$_2$(CR$^f$R$^g$)$_n$CONR$^d$R$^e$,
  14) —OC(O)R$^d$,
  15) —CN,
  16) —C(O)NR$^d$R$^e$,
  17) —NR$^d$C(O)R$^e$,
  18) —OC(O)NR$^d$R$^e$,
  19) —NR$^d$C(O)OR$^e$, or 20) —NR$^d$C(O)NR$^d$R$^e$;
21) —CR$^d$(N—OR$^e$), or
22) Cy optionally substituted with a group independently selected from R$^c$;

R$^b$ is 1) a group selected from R$^a$,
2) C$_{1-10}$alkyl,
3) C$_{2-10}$alkenyl,
4) C$_{2-10}$alkynyl, or
5) Cy-C$_{1-10}$alkyl,
wherein alkyl, alkenyl, alkynyl, and Cy are optionally substituted with a group independently selected from R$^c$;
substituted with a group independently selected from R$^c$;
R$^c$ is 1) halogen,
2) CN,
3) NH(C$_{1-5}$alkyl),
4) N(C$_{1-5}$alkyl)$_2$,
5) amino,
6) carboxy,
7) CC$_{1-4}$alkyl,
8) C$_{1-4}$alkoxy,
9) aryl,
10) aryl C$_{1-4}$alkyl, or
11) aryloxy;
R$^d$ and R$^e$ are independently selected from hydrogen, C$_{1-10}$alkyl, C$_{2-10}$alkenyl, C$_{2-10}$alkynyl, Cy and Cy-C$_{1-10}$alkyl, wherein alkyl, alkenyl, alkynyl and Cy is optionally substituted with one to four substituents independently selected from R$^c$; or
R$^d$ and R$^e$ together with the atoms to which they are attached form a heterocyclic ring of 5 to 7 members containing 0–2 additional heteroatoms independently selected from oxygen, sulfur and nitrogen;
R$^f$ and R$^g$ are independently selected from hydrogen, C$_{1-10}$alkyl, Cy and Cy-C$_{1-10}$alkyl; or
R$^f$ and R$^g$ together with the carbon to which they are attached form a ring of 5 to 7 members containing 0–2 heteroatoms independently selected from oxygen, sulfur and nitrogen;
R$^h$ is 1) hydrogen,
2) C$_{1-10}$alkyl,
3) C$_{2-10}$alkenyl,
4) C$_{2-10}$alkynyl,
5) cyano,
6) aryl,
7) aryl C$_{1-10}$alkyl,
8) heteroaryl,
9) heteroaryl C$_{1-10}$alkyl, or
10) —SO$_2$R$^i$;
wherein alkyl, alkenyl, and alkynyl are optionally substituted with one to four substituents independently selected from R$^a$; and aryl and heteroaryl are each optionally substituted with one to four substituents independently selected from R$^b$;
R$^i$) C$_{1-10}$alkyl,
2) C$_{1-10}$alkenyl,
3) C$_{2-10}$alkynyl, or
4) aryl;
wherein alkyl, alkenyl, alkynyl and aryl are each optionally substituted with one to four substituents independently selected from R$^c$;
Cy and Cy$^1$ are
1) cycloalkyl,
2) heterocyclyl,
3) aryl, or
35 4) heteroaryl;
m is an integer from 1 to 2;
n is an integer from 1 to 10;
p is 0 or 1.

In one subset of compounds of formula I R$^1$ is Cy or Cy-C$_{1-10}$alkyl where Cy and alkyl are optionally substituted as provided above under formula I. For the purpose of R$^1$, Cy is preferably aryl or heteroaryl each optionally substituted with one or two groups selected from R$^b$. Preferred R$^1$ groups are phenyl and pyridyl, each substituted with one or two groups independently selected from halogen, O—C$_{1-3}$alkyl, and trifluoromethyl. A more preferred R$^1$ is 3,5-dichlorophenyl (3,5-diCl—Ph) or (3—CF$_3$—Ph).

In another subset of compounds of formula I Y is —C(O)— or SO$_2$.
Preferred Y is SO$_2$.

In another subset of compounds of formula I R$^2$ is H or C$_{1-6}$alkyl.
Preferred R$^2$ groups are H and methyl.

In another subset of compounds of formula I X is —C(O)OR$^d$.

In another subset of compounds of formula I R$^7$ is hydrogen and R$^8$ is C$_{1-10}$alkyl, C$_{2-10}$alkenyl, Cy-(Cy$^1$)$_p$ or Cy-(Cy$^1$)$_p$—C$_{1-10}$alkyl, wherein alkyl, Cy and Cy$^1$ are optionally substituted as provided above under formula I, and p is 0 or 1. For the purpose of R$^8$, Cy and Cy$^1$ are preferably independently aryl, heteroaryl, or heterocyclyl each optionally substituted with one to three groups selected from R$^b$. Preferred R$^8$ are optionally substituted aryl, heteroaryl, aryl-C$_{1-3}$alkyl, heteroaryl-C$_{1-3}$alkyl, heteroaryl-aryl, heterocyclyl-aryl, aryl-aryl, aryl-aryl-C$_{1-10}$alkyl, and heteroaryl-aryl-C$_{1-3}$alkyl wherein the optional substituents are one to three groups independently selected from halogen, CN, OR$^d$, O(CO)R$^d$, C$_{1-5}$alkyl optionally substituted with one or two groups selected from R$^c$, CF$_3$, and OC(O)NR$^d$R$^e$; R$^c$, R$^d$ and R$^e$ are as defined under formula I. More preferred R$^8$ are optionally substituted phenyl, phenylmethyl, biphenyl, biphenylmethyl, heteroaryl-phenyl, heteryocyclyl-phenyl, and heteroaryl-phenylmethyl, wherein the optional substituents are one or two groups independently selected from halogen, CN, OR$^d$, O(CO)R$^d$, C$_{1-5}$alkyl optionally substituted with one or two groups selected from R$^c$, CF$_3$, and OC(O)NR$^d$R$^e$; R$^c$, R$^d$ and R$^e$ are as defined under formula I. Examples of R$^8$ include benzyl, phenyl, 4-fluorophenyl, 4-fluorobenzyl, 2'-methoxybiphenylmethyl, biphenyl, 2'-methoxybiphenyl, 4-hydroxyphenyl, 4-t-butoxyphenyl, 2'-cyano-biphenyl, 2'-formylbiphenyl, 2'-dimethylaminomethylbiphenyl, 2'-hydroxymethyl-biphenyl, 4-(2-methyl-5-CF$_3$-benzoxazol-7-yl)phenyl, 4-(pyrimidin-5-yl)phenyl, 4'-fluorobiphenyl, 2'-CF$_3$O-biphenyl, 3'-methoxybiphenyl, 2'-methoxy-3'-fluoro-iphenyl, 3'-methoxy-2'-fluorobiphenyl, 2'-methoxy-5'-fluoro-biphenyl, 3'-methoxy-5'-fluoro-biphenyl, 2'-methoxy-6'-fluorobiphenyl, 4-methoxyphenyl, 2'-CF$_{30-4}$'-fluorobiphenyl, 2'-methoxy-4'-fluorobiphenyl, 4-hydroxyphenyl, 4-(3'-pyridyl)-phenyl, 4-(N-pyrrolidinylcarbonyl)oxyphenyl, 3-(N-pyrrolidinylcarbonyl)oxyphenyl, 4-(2-methoxyethoxy)phenyl, 2'-cyanophenoxyphenyl, 3-(2'-methoxyphenyl)phenyl, 4-pyridyl, 3-quinolyl, 4-(2-pyridyl)phenyl, 4-(2-oxo-3-pyridyl)phenyl, 4-(2-methoxy-3-pyridyl)phenyl, 4-(2'-cyclopropoxy)biphenyl, 4-trifluoromethoxyphenyl, 2',6'-dimethoxybiphenyl, 2',5'-dimethoxybiphenyl, 2'-trifluoromethoxy-6'-methoxybiphenyl, 2'-fluoro-4',6'-dimethoxybiphenyl, 3'-fluoro-2',6'-dimethoxy-biphenyl, 3',5,-difluoro-2',6'-dimethoxybiphenyl, 4-cyclopentoxyphenyl, 4-(5-t-butylthiazol-2-yl)phenyl, 2,5-dimethoxyphenyl, 4-(thiazol-2-yl)phenyl, 2', 6'-dicyclopropoxybiphenyl, 4-eth6xyphenyl, 4-(2,2,2-trifluoroethoxy)

phenyl, 4-(fluoromethoxy)phenyl, 4-(3-tetrahydrofuranyloxy)phenyl, 4-(difluoromethoxy)-phenyl, 6-methoxy-3-pyridyl, 6-diallylamino-3-pyridyl, 3-benzyl-1,2,4-oxadiazol-5-yl, 2'-(fluorobenzyl)-1,2,4-oxadiazol-5-yl, 2'-(methoxybenzyl)-1,2,4-oxadiazol-5-yl.

In another subset of compounds of formula I $R^9$ and $R^{10}$ are each hydrogen.

In another subset of compounds of formula I the group

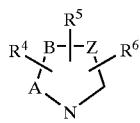

represents pyrrolidine, piperidine, piperazine, azetidine, oxazoline, thiazoline or tetrahydroisoquinoline.

A preferred embodiment of compounds of formula I are compounds of formula Ia:

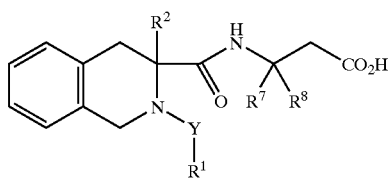

Ia wherein $R^2$ is H or $C_{1-6}$alkyl; Y is $-SO_2-$; $R^1$ is aryl or aryl-Cl 6alkyl wherein aryl is optionally substituted with one or two groups selected from $R^b$, and alkyl is substituted with one to four groups selected from $R^a$; $R^7$ is hydrogen; $R^8$ is aryl, aryl-aryl or aryl-$C_{1-6}$alkyl wherein aryl is optionally substituted with one to three groups selected from $R^b$, and alkyl is substituted with one to four groups selected from $R^a$.

Another preferred embodiment of compounds of formula I are compounds of formula Ib:

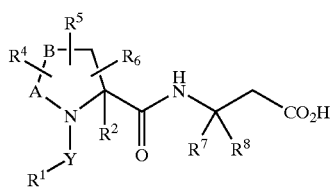

Ib wherein
$R^1$ is Cy or Cy-$C_{1-10}$alkyl where Cy and alkyl are optionally substituted as provided above under formula I;
$R^2$ is H or $C_{1-6}$ alkyl;
B is N, O, S, a bond, $CH_2$ or $CH_2CH_2$;
A is —C— or —C—C—;
Y is CO or $-SO_2-$;
$R^4$, $R^5$, $R^6$ are independently selected from H, $C_{1-6}$ alkyl and halogen;
$R^7$ is hydrogen;
$R^8$ is $C_{1-10}$alkyl, $C_{2-10}$alkenyl, Cy-$(Cy^1)_p$, Cy-$(Cy^1)_p$-$C_{1-10}$alkyl, or $CO_2R^d$
wherein alkyl, Cy and $Cy^1$ are optionally substituted as provided above under formula I, and p is 0 or 1.

In a more preferred embodiment of compounds of formula Ib, $R^1$ is aryl, heteroaryl or aryl-$C_{1-6}$alkyl wherein aryl is optionally substituted with one or two groups selected from halogen, O-$C_{1-3}$alkyl, and trifluoromethyl;

$R^2$ is H or methyl;
$R^8$ is optionally substituted aryl, heteroaryl, aryl-$C_{1-3}$ alkyl, heteroaryl-$C_{1-3}$alkyl, heteroaryl-aryl, aryl-aryl, aryl-aryl-$C_{1-3}$alkyl, heteroaryl-aryl-$C_{1-3}$alkyl, or $CO_2R^d$ wherein the optional substituents are one to three groups independently elected from halogen, CN, $OR^d$, $O(CO)R^d$, $C_{1-5}$alkyl optionally substituted with one or two groups selected from $R^c$, $CF_3$, and $OC(O)NR^dR^e$; $R^c$, $R^d$ and $R^e$ are as defined under formula I.

In another more preferred embodiment of compounds of formula Ib, $R^1$ is phenyl optionally substituted with one or two groups selected from halogen, O-$C_{1-3}$alkyl, and trifluoromethyl;
Y is $SO_2$;
A is —C—;
B is selected from $CH_2$, O, S and a bond;
$R^2$ is H or methyl;
$R^4$, $R^5$, $R^6$ are independently selected from H, $C_{1-3}$alkyl and halogen;
$R^7$ is hydrogen;
$R^8$ is aryl, heteroaryl, aryl-aryl, aryl-heteroaryl or heteroaryl-aryl wherein aryl and heteroaryl are optionally substituted with one to three groups selected from halogen, CN, $OR^d$, $O(CO)R^d$, $C_{1-5}$alkyl optionally substituted with one or two groups selected from $R^c$, $CF_3$, and $OC(O)NR^dR^e$; $R^c$, $R^d$ and $R^e$ are as defined under formula I.

In one subset of formula Ib are compounds of formula Ic:

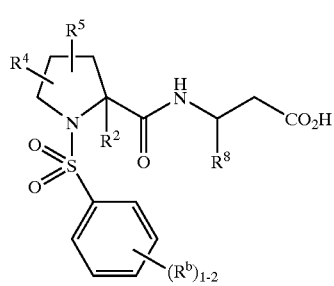

Ic wherein
$R^2$ is H or methyl;
$R^4$ and $R^5$ are independently H, halogen and $CH_3$;
$R^8$ is aryl, aryl-aryl, heteroaryl-aryl (wherein aryl is attached to the propionic acid backbone) and wherein aryl and heteroaryl are optionally substituted with one to three groups selected from halogen, CN, $OR^d$, $O(CO)R^e$, $C_{1-5}$alkyl optionally substituted with one or two groups selected from $R^c$, $CF_3$, and $OC(O)NR^dR^e$;
$R^b$ is 1) halogen,
2) CN,
3) $OR^d$,
4) $O(CO)R^d$,
5) $C_{1-5}$alkyl optionally substituted with one or two groups selected from $R^c$,
6) $CF_3$, or
7) $OC(O)NR^dR^e$;
$R^c$, $R^d$ and $R^e$ are as defined under formula I.

More preferred compounds of formula Ic are those wherein for $R^8$ aryl is phenyl and heteroaryl is selected from the group consisting of pyridyl, pyrimidinyl, thiazolyl and oxadiazolyl.

Another subset of formula Ib are compounds of formula Id:

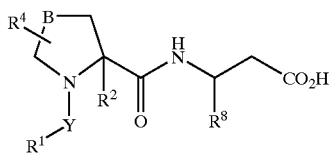

Id wherein
- B is a bond, O or S;
- Y is SO$_2$;
- R$^1$ is phenyl optionally substituted with one or two groups selected from halogen, O-C$_{1-3}$alkyl, and trifluoromethyl;
- R$^2$ is H or methyl;
- R$^4$ is selected from H, C$_{1-10}$alkyl and halogen;
- R$^8$ is aryl, heteroaryl, aryl-aryl, aryl-heteroaryl or heteroaryl-aryl wherein aryl and heteroaryl are optionally substituted with one to three groups selected from halogen, CN, OR$^d$, O(CO)R$^d$, C$_{1-5}$alkyl optionally substituted with one or two groups selected from R$^c$, CF$_3$, and OC(O)NR$^d$R$^e$; R$^c$, R$^d$ and R$^e$ are as defined under formula I.

In one preferred subset of compounds of formula Id are compounds of formula Ie:

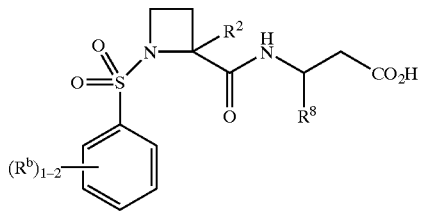

wherein
- R$^2$ is H or methyl; R$^8$ is aryl, heteroaryl, aryl-aryl, aryl-heteroaryl or heteroaryl-aryl wherein aryl and heteroaryl are optionally substituted with one to three groups selected from halogen, CN, OR$^d$, O(CO)R$^d$, C$_{1-5}$alkyl optionally substituted with one or two groups selected from Rc, CF$_3$, and OC(O)NR$^d$R$^e$;
- R$^b$ is 1) halogen,
  2) OR$^d$, or
  3) CF$_3$.

In another preferred subset of Id are compounds of formula If

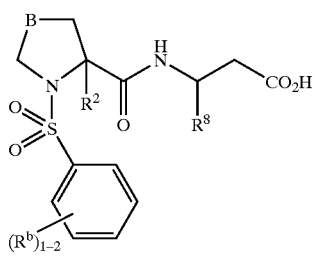

If wherein
- B is O or S;
- R$^2$ is H or methyl;
- R$^8$ is aryl, heteroaryl, aryl-aryl, aryl-heteroaryl or heteroaryl-aryl wherein aryl and heteroaryl are optionally substituted with one to three groups selected from halogen, CN, OR$^d$, O(CO)R$^d$, C$_{1-5}$alkyl optionally substituted with one or two groups selected from R$^c$, CF$_3$, and OC(O)NR$^d$R$^e$;
- R$^b$ is 1) halogen,
  2) OR$^d$, or
  3) CF$_3$.

R$^e$presentative compounds of formula I are as follows (biphenyl is 4-biphenyl, unless otherwise specified):

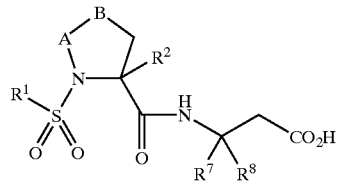

R$^7$ hydrogen unless otherwise specified.

| 2/3* | A-B | R$^1$ | R$^2$ | R$^8$ |
|---|---|---|---|---|
| S/S | CH$_2$—CH$_2$ | 3,5-diCl-Ph | H | CO$_2$H |
| S/R | CH$_2$—CH$_2$ | 3,5-diCl-Ph | H | trans-1-propenyl |
| S/R | CH$_2$—CH$_2$ | 3,5-diCl-Ph | H | isobutyl |
| S/S | CH$_2$—CH$_2$ | 3,5-diCl-Ph | H | isobutyl |
| S/R | CH$_2$—CH$_2$ | 3,5-diCl-Ph | H | benzyl |
| S/R | CH$_2$—CH$_2$ | 3,5-diCl-Ph | H | phenyl |
| S/S | CH$_2$—CH$_2$ | 3,5-diCl-Ph | H | phenyl |
| S/R | CH$_2$—CH$_2$ | 3-Cl-Ph | H | phenyl |
| S/S | CH$_2$CH$_2$—CH$_2$ | 4-NO$_2$-Ph | H | 3,4-methylenedioxyphenyl |
| S/R | CH$_2$—CH$_2$ | 3,5-diCl-Ph | CH$_3$ | 4-F-phenyl |
| S/R | CH$_2$—CH$_2$ | 3,5-diCl-Ph | H | 2-naphthylmethyl |
| S/R | CH$_2$—CH$_2$ | 3,5-diCl-Ph | H | 4-fluorophenyl |
| S/S | CH$_2$—CH$_2$ | 3,5-diCl-Ph | H | 4-fluorophenyl |
| S/R | CH$_2$—CH$_2$ | 3,5-diCl-Ph | H | 4-fluorobenzyl |
| S/R | CH$_2$—CH$_2$ | 3,5-diCl-Ph | CH$_3$ | 4-fluorobenzyl |
| S/S | CH$_2$—CH$_2$ | 3,5-diCl-Ph | CH$_3$ | 4-F-phenyl |
| S/S | CH$_2$—CH$_2$ | 3,5-diCl-Ph | H | 2'-methoxybiphenylmethyl |
| S/R | CH$_2$—CH$_2$ | 3,5-diCl-Ph | H | biphenyl |
| S/S | CH$_2$—CH$_2$ | 3,5-diCl-Ph | H | biphenyl |
| S/R | CH$_2$—CH$_2$ | 3,5-diCl-Ph | H | 2'-methoxybiphenyl |
| S/S | CH$_2$—CH$_2$ | 3,5-diCl-Ph | H | 2'-methoxybiphenyl |
| S/R | CH$_2$—CH$_2$ | 3,5-diCl-Ph | H | 4-hydroxyphenyl |
| S/S | CH$_2$—CH$_2$ | 3,5-diCl-Ph | H | 4-hydroxyphenyl |
| S/R | CH$_2$—CH$_2$ | 3,5-diCl-Ph | H | 4-t-butoxyphenyl |
| S/R | CH$_2$—CH$_2$ | 3,5-diCl-Ph | H | 2'-cyanobiphenyl |
| S/R | CH$_2$—CH$_2$ | 3,5-diCl-Ph | H | 2'-formylbiphenyl |
| S/R | CH$_2$—CH$_2$ | 3,5-diCl-Ph | H | 2'-dimethylamino-methylbiphenyl |
| S/R | CH$_2$—CH$_2$ | 3,5-diCl-Ph | H | 2'-hydroxymethylbiphenyl |
| S/R | CH$_2$—CH$_2$ | 3,5-diCl-Ph | H | 4-(2-methyl-5-CF$_3$-benzoxazol-7-yl)phenyl |
| S/R | CH$_2$—CH$_2$ | 3,5-diCl-Ph | H | 4-(pyrimidin-5-yl)-phenyl |
| S/R | CH$_2$—CH$_2$ | Ph | H | 2'-methoxybiphenyl |
| S/R | CH$_2$—CH$_2$ | 3-pyridyl | H | 2'-methoxybiphenyl |
| S/R | CH$_2$—CH$_2$ | Ph | CH$_3$ | 2'-methoxybiphenyl |
| S/R | CH$_2$—CH$_2$ | 3-pyridiyl | CH$_3$ | 2'-methoxybiphenyl |
| S/R | CH$_2$—CH$_2$ | 3,5-diCl-Ph | CH$_3$ | 2'-methoxybiphenyl |
| S/R | CH$_2$—CH$_2$ | Ph | CH$_3$ | 4'-fluorobiphenyl |
| S/R | CH$_2$—CH$_2$ | 3,5-diCl-Ph | H | 4'-fluorobiphenyl |
| S/R | CH$_2$—CH$_2$ | 3,5-diCl-Ph | H | 2'-CF$_3$O-biphenyl |
| S/R | CH$_2$—CH$_2$ | 3,5-diCl-Ph | CH$_3$ | 2'-CF$_3$O-biphenyl |
| S/R | CH$_2$—CH$_2$ | 3,5-diCl-Ph | CH$_3$ | 3'-methoxybiphenyl |
| S/R | CH$_2$—CH$_2$ | 3,5-diCl-Ph | H | 3'-methoxybiphenyl |
| S/R | CH$_2$—CH$_2$ | 3,5-diCl-Ph | CH$_3$ | 2'-methoxy-3'-F-biphenyl |
| S/R | CH$_2$—CH$_2$ | 3,5-diCl-Ph | H | 2'-methoxy-3'-F-biphenyl |
| S/R | CH$_2$—CH$_2$ | 3,5-diCl-Ph | CH$_3$ | 3'-methoxy-2'-F-biphenyl |
| S/R | CH$_2$—CH$_2$ | 3,5-diCl-Ph | H | 3'-methoxy-2'-F-biphenyl |
| S/R | CH$_2$—CH$_2$ | 3,5-diCl-Ph | CH$_3$ | 2'-methoxy-5'-F-biphenyl |
| S/R | CH$_2$—CH$_2$ | 3,5-diCl-Ph | H | 2'-methoxy-5'-F-biphenyl |
| S/R | CH$_2$—CH$_2$ | 3,5-diCl-Ph | CH$_3$ | 3'-methoxy-5'-F-biphenyl |
| S/R | CH$_2$—CH$_2$ | 3,5-diCl-Ph | H | 3'-methoxy-5'-F-biphenyl |
| S/R | CH$_2$—CH$_2$ | 3,5-diCl-Ph | CH$_3$ | 2'-methoxy-6'-F-biphenyl |

-continued

| 2/3* | A-B | R¹ | R² | R⁸ |
|---|---|---|---|---|
| S/R | CH$_2$—CH$_2$ | 3,5-diCl-Ph | H | 2'-methoxy-6'-F-biphenyl |
| S/R | CH$_2$—CH$_2$ | 3-Cl-Ph | CH$_3$ | 2'-methoxybiphenyl |
| S/R | CH$_2$—CH$_2$ | 3,5-diCl-Ph | CH$_3$ | 4-methoxyphenyl |
| S/R | CH$_2$—CH$_2$ | 3,5-diCl-Ph | H | 4-methoxyphenyl |
| S/R | CH$_2$CH$_2$—CH$_2$ | 3,5-diCl-Ph | H | 2'-methoxybiphenyl |
| S/R | CH$_2$—CH$_2$ | 3,5-diCl-Ph | CH$_3$ | 2'-CF$_3$O-4'-F-biphenyl |
| S/R | CH$_2$—CH$_2$ | 3,5-diCl-Ph | H | 2'-CF$_3$O-4'-F-biphenyl |
| S/R | CH$_2$—CH$_2$ | 3,5-diCl-Ph | H | 2'-methoxy-4'-F-biphenyl |
| S/R | CH$_2$—CH$_2$ | 3,5-diCl-Ph | CH$_3$ | 2'-methoxy-4'-F-biphenyl |
| S/R | CH$_2$—CH$_2$ | 3,5-diCl-Ph | CH$_3$ | 4-hydroxyphenyl |
| S/R | CH$_2$—CH$_2$ | 3,5-diCl-Ph | CH$_3$ | 4-(3'-pyridyl)phenyl |
| S/R | CH$_2$—CH$_2$ | 3,5-diCl-Ph | H | 4-(N-pyrrolidinyl-carbonyl)oxyphenyl |
| S/R | CH$_2$—CH$_2$ | 3,5-diCl-Ph | H | 3-(N-pyrrolidinyl-carbonyl)oxyphenyl |
| S/R | CH$_2$—CH$_2$ | 3,5-diCl-Ph | H | 4-(2-methoxyethoxy)-phenyl |
| S/R | CH$_2$—CH$_2$ | 3,5-diCl-Ph | CH$_3$ | 4-(2-methoxyethoxy)-phenyl |
| S/R | CH$_2$—CH$_2$ | 3,5-diCl-Ph | H | 2'-cyanophenoxy-phenyl |
| S/R | CH$_2$—CH$_2$ | 3,5-diCl-Ph | H | 3-(2'-methoxyphenyl)-phenyl |
| S/R | CH$_2$—CH$_2$ | 3,5-diCl-Ph | CH$_3$ | 4-pyridyl |
| S/S | CH$_2$—CH$_2$ | 3,5-diCl-Ph | CH$_3$ | 4-pyridyl |
| S/R | CH$_2$—CH$_2$ | 3,5-diCl-Ph | CH$_3$ | 3-quinolyl |
| S/R | CH$_2$—CH$_2$ | 3,5-diCl-Ph | H | 4-(2'-pyridyl)phenyl |
| S/R | CH$_2$—CH$_2$ | 3,5-diCl-Ph | CH$_3$ | 4-(2-oxo-3-pyridyl)-phenyl |
| S/R | CH$_2$—CH$_2$ | 3,5-diCl-Ph | H | 4-(2-oxo-3-pyridyl)-phenyl |
| S/R | CH$_2$—CH$_2$ | 3,5-diCl-Ph | CH$_3$ | 4-(2-methoxy-3-pyridyl)phenyl |
| R/R | CH$_2$CH$_2$—NH | 3,5-diCl-Ph | H | 2'-methoxybiphenyl |
| S/R | CH$_2$CH$_2$—NH | 3,5-diCl-Ph | H | 2'-methoxybiphenyl |
| (R,S)/R | CH$_2$CH$_2$—NH | Ph | H | 2'-methoxybiphenyl |
| S/R | CH$_2$CH$_2$—NCH$_3$ | 3,5-diCl-Ph | H | 2'-methoxybiphenyl |
| S/R | CH$_2$—CH$_2$ | 3,5-diCl-Ph | H | 4-(2'-cyclopropoxy)-biphenyl |
| S/R | CH$_2$—CH$_2$ | 3,5-diCl-Ph | CH$_3$ | 4-(2'-cyclopropoxy)-biphenyl |
| S/R | CH$_2$—CH$_2$ | 3,5-diCl-Ph | H | 4-CF$_3$O-phenyl |
| S/R | CH$_2$—CH$_2$ | 3,5-diCl-Ph | H | 2-fluorophenyl |
| S/R | CH$_2$ | 3,5-diCl-Ph | H | 4-methoxyphenyl |
| S/R | CH$_2$ | 3,5-diCl-Ph | H | phenyl |
| S/R | CH$_2$—CH$_2$ | Ph | CH$_3$ | 2',6'-dimethoxybiphenyl |
| S/R | CH$_2$—CH$_2$ | 3,5-diCl-Ph | H | 2',6'-dimethoxybiphenyl |
| S/R | CH$_2$—CH$_2$ | 3,5-diCl-Ph | CH$_3$ | 2',6'-dimethoxybiphenyl |
| S/R | CH$_2$ | 3,5-diCl-Ph | H | 2',6'-dimethoxybiphenyl |
| S/R | CH$_2$ | 3,5-diCl-Ph | H | 2'-methoxybiphenyl |
| S/R | CH$_2$—CH$_2$ | 3,5-diCl-Ph | H | 2',5'-dimethoxybiphenyl |
| S/R | CH$_2$—CH$_2$ | 3,5-diCl-Ph | CH$_3$ | 2',5'-dimethoxybiphenyl |
| S/R | CH$_2$—CH$_2$ | 3,5-diCl-Ph | CH$_3$ | 2'-CF$_3$O-6'-methoxy-biphenyl |
| S/R | CH$_2$ | 3,5-diCl-Ph | CH$_3$ | 2'-CF$_3$O-6'-methoxy-biphenyl |
| S/R | CH$_2$ | 3,5-diCl-Ph | H | 2'-fluoro-4',6'-dimethoxybiphenyl |
| S/R | CH$_2$—CH$_2$ | 3,5-diCl-Ph | CH$_3$ | 2'-fluoro-4',6'-dimethoxybiphenyl |
| S/R | CH$_2$—CH$_2$ | 3,5-diCl-Ph | CH$_3$ | 2',6'-dimethoxy-3'-fluorobiphenyl |
| S/R | CH$_2$—CH$_2$ | 3,5-diCl-Ph | H | 2',6'-dimethoxy-3'-fluorobiphenyl |
| S/R | CH$_2$ | 3,5-diCl-Ph | H | 2',6'-dimethoxy-3'-fluorobiphenyl |
| S/R | CH$_2$—CH$_2$ | 3,5-diCl-Ph | CH$_3$ | 2',6'-dimethoxy-3',5'-difluorobiphenyl |
| S/R | CH$_2$—O | 3,5-diCl-Ph | H | 2'-methoxybiphenyl |
| S/R | CH$_2$—CH$_2$ | 3,5-diCl-Ph | H | 4-(2'-thiazolyl)phenyl |
| S/R | CH$_2$—O | 3,5-diCl-Ph | H | 2',6'-dimethoxy-biphenyl |
| S/R | CH$_2$—O | 3,5-diCl-Ph | H | phenyl |
| S/R | CH$_2$—O | 3,5-diCl-Ph | H | 4-methoxyphenyl |
| S/R | CH$_2$—O | 3,5-diCl-Ph | CH$_3$ | 2',6'-dimethoxy-biphenyl |
| S/R | CH$_2$—O | 3,5-diCl-Ph | CH$_3$ | 2'-methoxybiphenyl |
| S/R | CH$_2$—O | Ph | CH$_3$ | 2',6'-dimethoxy-biphenyl |
| S/R | CH$_2$ | 2-thiophene | H | phenyl |
| R/R | CH$_2$—S | 3,5-diCl-Ph | H | phenyl |
| S/R | CH$_2$—S | 3,5-diCl-Ph | H | phenyl |
| S/R | CH$_2$CH$_2$ (3-Me)** | 3,5-diCl-Ph | H | phenyl |
| S/R | CH$_2$—CH$_2$ | Ph | H | 2'-cyclopropoxy-biphenyl |
| S/R | CH$_2$—CH$_2$ | 3-CF$_3$-Ph | H | 2'-cyclopropoxybiphenyl |
| S/R | CH$_2$ | 3-Cl-Ph | H | 2'-cyclopropoxybiphenyl |
| S/R | CH$_2$—CF$_2$ | Ph | H | 2'-cyclopropoxybiphenyl |
| S/R | CH$_2$ | 3,5-diCl-Ph | H | 2',6'-dicyclopropoxy-biphenyl |
| S/R | CH$_2$ | 3,5-diCl-Ph | H | 2'-cyclopropoxy-6'-fluorobiphenyl |
| S/R | CH$_2$ | 3-Cl-Ph | H | 2'-cyclopropoxy-6'-fluorobiphenyl |
| S/R | CH$_2$ | 2-thiophene | H | 2'-cyclopropoxy-6'-fluorobiphenyl |
| S/R | CH$_2$ | 3-F-Ph | H | 2',6'-dimethoxybiphenyl |
| S/R | CH$_2$ | 2-thiophene | H | 2',6'-dimethoxybiphenyl |
| S/R | CH$_2$ | 3,5-diMe-isoxazole | H | 2',6'-dimethoxy-biphenyl |
| S/R | CH$_2$ | 3,5-diCl-Ph | H | 4-ethoxyphenyl |
| S/R | CH$_2$—CH$_2$ | 3,5-diCl-Ph | H | 4-cyclopentoxyphenyl |
| S/R | CH$_2$ | 3,5-diCl-Ph | H | 4-(2,2,2-trifluoro-ethoxy)phenyl |
| S/R | CH$_2$ | 3,5-diCl-Ph | H | 4-(fluoromethoxy)phenyl |
| S/R | CH$_2$ | 3,5-diCl-Ph | H | 4-(3-tetrahydrofuryl-oxy)phenyl |
| S/R | CH$_2$—CH$_2$ | 3,5-diCl-Ph | H | 4-(cyclopropoxy)phenyl |
| S/R | CH$_2$ | 3,5-diCl-Ph | H | 4-(difluoromethoxy)phenyl |
| S/R | CH$_2$ | 3,5-diCl-Ph | H | 4-methoxyphenyl R⁷ = methyl |
| S/R | CH$_2$—CH$_2$ | 3,5-diCl-Ph | H | 4-methoxyphenyl R⁷ = methyl |
| S/R | CH$_2$—CH$_2$ | 3,5-diCl-Ph | H | R⁷ + R⁸ + C to which they are attached = 1-indanyl |
| S/R | CH$_2$ | 3,5-diCl-Ph | H | 6-methoxy-3-pyridyl |
| S/R | CH$_2$ | 3,5-diCl-Ph | H | 6-diallyamino-3-pyridyl |
| S/R | CH$_2$—CH$_2$ | 3,5-diCl-Ph | H | 3-benzyl-1,2,4-oxadiazol-5-yl |
| S/R | CH$_2$—CH$_2$ | 3,5-diCl-Ph | H | 3-(2'-fluorobenzyl)-1,2,4-oxadiazol-5-yl |
| S/R | CH$_2$—CH$_2$ | 3,5-diCl-Ph | H | 3-(2'-methoxybenzyl) 1,2,4-oxadiazol-5-yl |
| S/R | CH$_2$ | 3,5-diCl-Ph | CH$_3$ | 2',6'-dimethoxybiphenyl |
| R/R | CH$_2$ | 3,5-diCl-Ph | CH$_3$ | 2',6'-dimethoxybiphenyl |
| S/R | CH$_2$ | 3,5-diCl-Ph | CH$_3$ | 4-methoxyphenyl |
| R/R | CH$_2$ | 3,5-diCl-Ph | CH$_3$ | 4-methoxyphenyl |
| S/R | CH$_2$—CH$_2$ | 3,5-diCl-Ph | H | 4-(5'-t-butyl-2-thiazolyl)phenyl |

*Stereo configuration at the indicated positions
**ring is 3-methylpyrrolidine

N-((3,4-dimethoxybenzenesulfonyl)-1,2,3,4-tetrahydroisoquinoline-3 (S)-carbonyl)-3-amino-propionic acid;

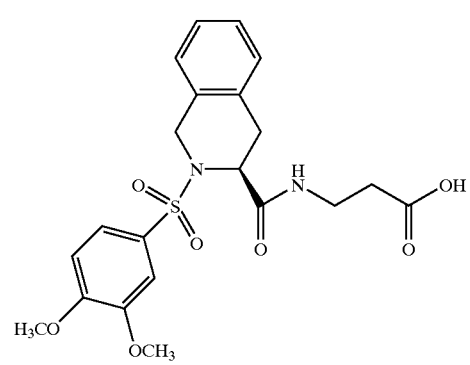

N-(4-(N'-2-chlorophenyl-ureido)phenylacetyl)-(S)-prolyl-3 (S)-(3,4-methylenedioxyphenyl)-3-amino-propionic acid;

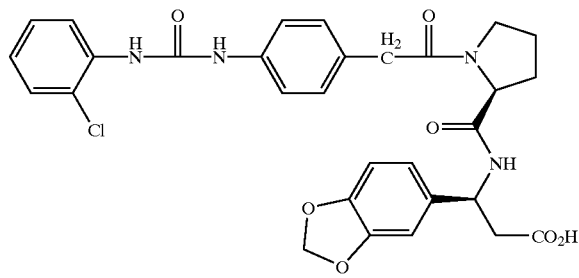

N-(3,4-dimethoxybenzenesulfornyl)-1,2,3,4-tetrahydroisoquinoline-3(S)-carbonyl)-3(S)-(3,4-methylenedioxyphenyl)-3-amino-propionic acid;

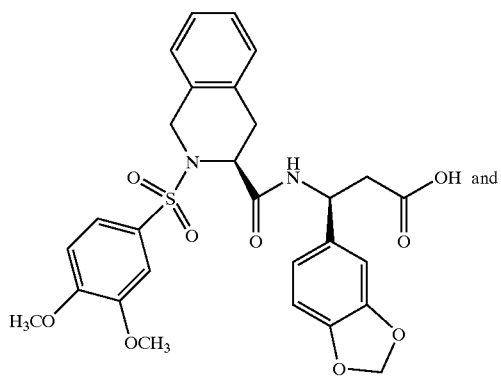

N-(2(R,S)-(4-(benzyloxycarbonyl)-1-(t-butyloxycarbonyl)) piperazoyl)-3(R)-amino-3-(4-(2'-methoxyphenyl)phenyl) propionic acid

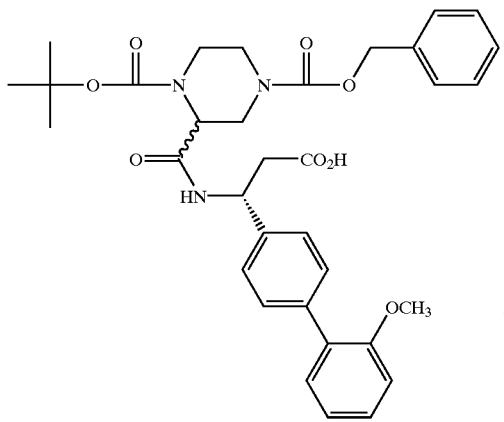

"Alkyl", as well as other groups having the prefix "alk", such as alkoxy, alkanoyl, means carbon chains which may be linear or branched or combinations thereof. Examples of alkyl groups include methyl, ethyl, propyl, isopropyl, butyl, sec- and tert-butyl, pentyl, hexyl, heptyl, octyl, nonyl, and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means mono- or bicyclic saturated carbocyclic rings, each of which having from 3 to 10 carbon atoms. The term also inccludes monocyclic ring fused to an aryl group in which the point of attachment is on the non-aromatic portion. Examples of cycloalkyl include cyclopropyl, cyclopentyl, cyclohexyl, cycloheptyl, tetrahydronaphthyl, decahydronaphthyl, indanyl, and the like.

"Aryl" means mono- or bicyclic aromatic rings containing only carbon atoms. The term also includes aryl group fused to a monocyclic cycloalkyl or monocyclic heterocyclyl group in which the point of attachment is on the aromatic portion. Examples of aryl include phenyl, naphthyl, indanyl, indenyl, tetrahydro-naphthyl, 2,3-dihydrobenzofuranyl, benzopyranyl, 1,4-benzodioxanyl, 1,3-benzo-dioxolyl, and the like.

"Heteroaryl" means a mono- or bicyclic aromatic ring containing at least one heteroatom selected from N, O and S, with each ring containing 5 to 6 atoms. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzo-thiazolyl, benzimidazolyl, benzofuranyl, benzothiophenyl, furo(2,3-b)pyridyl, quinolyl, indolyl, isoquinolyl, and the like.

"Heterocyclyl" means mono- or bicyclic saturated rings containing at least one heteroatom selected from N, S and O, each of said ring having from 3 to 10 atoms. The term also includes monocyclic heterocycle fused to an aryl or heteroaryl group in which the point of attachment is on the non-aromatic portion. Examples of "heterocyclyl" include pyrrolidinyl, piperidinyl, piperazinyl, imidazolidinyl, 2,3-dihydrofuro(2,3-b)pyridyl, benzoxazinyl, tetrahydroquinolinyl, tetrahydroisoquinolinyl, dihydroindolyl, and the like. The term also includes partially unsaturated monocyclic rings that are not aromatic, such as 2- or 4-pyridones or N-substituted-(1H,3H)-pyrimidine-2,4-diones (N-substituted uracils).

"Halogen" includes fluorine, chlorine, bromine and iodine.

Some of the following abbreviations are used in the application:

| | |
|---|---|
| BOC (boc) | t-butyloxycarbonyl |
| Bu | butyl |
| calc. | calculated |
| CBZ (Cbz) | benzyloxycarbonyl |
| DCC | dicyclohexylcarbodiimide |
| DIEA | diisopropylethylamine |
| DMAP | 4-(N,N-dimethylamino)pyridine |
| DMF | dimethylformamide |
| DMSO | dimethylsulfoxide |
| EDC | 1-(3-dimethylaminopropyl)3-ethylcarbodiimide HCl |
| eq. | equivalent(s) |
| EtOAc | ethyl acetate |
| FAB-MS | fast atom bombardment-mass spectroscopy |
| FMOC (Fmoc) | fluororenylmethoxycarbonyl |
| HBTU | 2-(1H-benzotriazol-1-yl)-1,1,3,3-tetramethyluronium hexafluorophosphate |
| HOBt | 1-hydroxybenzotriazole hydrate |
| HPLC | high pressure liquid chromatography |
| K/Li HDMS | potassium/lithium bis(trimethylsilyl)amide |

| | |
|---|---|
| LAH | lithium aluminum hydride |
| LHMDS | lithium bis(trimethylsilyl)amide |
| Me | methyl |
| MF | molecular formula |
| MHz | megahertz |
| Ms | methanesulfonyl |
| NBS | N-bromosuccinimde |
| NMM | N-methylmorpholine |
| NMP | N-methylpyrrolidin-2-one |
| NMR | nuclear magnetic resonance |
| Ph | phenyl |
| Pr | propyl |
| prep. | prepared |
| PyBOP | benzotriazol-1-yloxytripyrrolidino phosphonium hexafluorophosphate |
| TFA | trifluoroacetic acid |
| THF | tetrahydrofuran |
| Tic | 1,2,3,4-tetrahydroisoquinoline-3-carboxylic acid |
| TLC | thin-layer chromatography |

Optical Isomers—Diastereomers—Geometric Isomers—Tautomers

Compounds of Formula I contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of Formula I.

Compounds of the Formula I may be separated into diastereoisomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent.

Alternatively, any enantiomer of a compound of the general Formula I or Ia may be obtained by stereospecific synthesis using optically pure starting materials or reagents of known configuration.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-dibenzylethylenediamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, as used herein, references to the compounds of Formula I are meant to also include the pharmaceutically acceptable salts.

Utilities

The ability of the compounds of Formula I to antagonize the actions of VLA-4 and/or α4β7 integrin makes them useful for preventing or reversing the symptoms, disorders or diseases induced by the binding of VLA-4 and or α4β7 to their various respective ligands. Thus, these antagonists will inhibit cell adhesion processes including cell activation, migration, proliferation and differentiation. Accordingly, another aspect of the present invention provides a method for the treatment (including prevention, alleviation, amelioration or suppression) of diseases or disorders or symptoms mediated by VLA-4 and/or α4β7 binding and cell adhesion and activation, which comprises administering to a mammal an effective amount of a compound of Formula I. Such diseases, disorders, conditions or symptoms are for example (1) multiple sclerosis, (2) asthma, (3) allergic rhinitis, (4) allergic conjunctivitis, (5) inflammatory lung diseases, (6) rheumatoid arthritis, (7) septic arthritis, (8) type I diabetes, (9) organ transplantation rejection, (10) restenosis, (11) autologous bone marrow transplantation, (12) inflammatory sequelae of viral infections, (13) myocarditis, (14) inflammatory bowel disease including ulcerative colitis and Crohn's disease, (15) certain types of toxic and immune-based nephritis, (16) contact dermal hypersensitivity, (17) psoriasis, (18) tumor metastasis, (19) hepatitis, and (20) atherosclerosis.

Dose Ranges

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases.

For use where a composition for intravenous administration is employed, a suitable dosage range is from about 0.001 mg to about 25 mg (preferably from 0.01 mg to about 1 mg) of a compound of Formula I per kg of body weight per day and for cytoprotective use from about 0.1 mg to about 100 mg (preferably from about 1 mg to about 100 mg and more preferably from about 1 mg to about 10 mg) of a compound of Formula I per kg of body weight per day.

In the case where an oral composition is employed, a suitable dosage range is, e.g. from about 0.01 mg to about 100 mg of a compound of Formula I per kg of body weight per day, preferably from about 0.1 mg to about 10 mg per kg and for cytoprotective use from 0.1 mg to about 100 mg (preferably from about 1 mg to about 100 mg and more preferably from about 10 mg to about 100 mg) of a compound of Formula I per kg of body weight per day.

For the treatment of diseases of the eye, ophthalmic preparations for ocular administration comprising 0.001–1% by weight solutions or suspensions of the compounds of Formula I in an acceptable ophthalmic formulation may be used.

Pharmaceutical Compositions

Another aspect of the present invention provides pharmaceutical compositions which comprises a compound of Formula I and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formula I in suitable propellants, such as fluorocarbons or hydrocarbons.

Suitable topical formulations of a compound of formula I include transdermal devices, aerosols, creams, ointments, lotions, dusting powders, and the like.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 1 mg to about 500 mg of the active ingredient and each cachet or capsule contains from about 1 to about 500 mg of the active ingredient.

The following are examples of representative pharmaceutical dosage forms for the compounds of Formula I:

| Injectable Suspension (I.M.) | mg/mL |
|---|---|
| Compound of Formula I | 10 |
| Methylcellulose | 5.0 |
| Tween 80 | 0.5 |
| Benzyl alcohol | 1.0 |
| Benzalkonium chloride | 1.0 |
| Water for injection to a vol. of 1 mL | |

| Tablet | mg/tablet |
|---|---|
| Compound of Formula I | 25 |
| Microcrystalline Cellulose | 415 |
| Povidone | 14.0 |
| Pregelatinized Starch | 43.5 |
| Magnesium Stearate | 2.5 |
| | 500 |

| Capsule | mg/capsule |
|---|---|
| Compound of Formula I | 25 |
| Lactose Powder | 573.5 |
| Magnesium Stearate | 1.5 |
| | 600 |

| Aerosol | Per canister |
|---|---|
| Compound of Formula I | 24 mg |
| Lecithin, NF Liquid Concentrate | 1.2 mg |
| Trichlorofluoromethane, NF | 4.025 g |
| Dichlorodifluoromethane, NF | 12.15 g |

Combination Therapy

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula 1. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula 1, either administered separately or in the same pharmaceutical compositions, include, but are not limited to:

(a) other VLA-4 antagonists such as those described in U.S. Pat. No. 5,510,332, WO97/03094, WO97/02289, WO96/40781, WO96/22966, WO96/20216, WO96/01644, WO96/06108, WO95/15973 and WO96/31206; (b) steroids such as beclomethasone, methylprednisolone, betamethasone, prednisone, dexamethasone, and hydrocortisone;

(c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as β2-agonists (terbutaline, metaproterenol, fenoterol, isoetharine, albuterol, bitolterol, and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); (f) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors such as celecoxib; (h) inhibitors of phosphodiesterase type IV (PDE-IV); (i) antagonists of the chemokine receptors, especially CCR-1, CCR-2, and CCR-3; (j) cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (k) anti-diabetic agents such as insulin, sulfonylureas, biguanides (metformin), α-glucosidase inhibitors (acarbose) and glitazones (troglitazone, pioglitazone, englitazone, MCC-555, BRL49653 and the like); (l) preparations of interferon beta (interferon beta-1a, interferon beta-1b); (m) anticholinergic agents such as muscarinic antagonists (ipratropium bromide); (n) other compounds such as 5-aminosalicylic acid and prodrugs thereof, antimetabolites such as azathioprine and 6-mercaptopurine, and cytotoxic cancer chemotherapeutic agents.

The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

Compounds of the present invention may be prepared by procedures illustrated in the accompanying schemes. In Scheme 1, a resin-based synthetic strategy is outlined where the resin employed is represented by the ball (◯). An N-Fmoc-protected amino acid derivative A (Fmoc=fluorenylmethoxycarbonyl) is loaded on to the appropriate hydroxyl-containing resin using a coupling agent such as dicyclohexylcarbodiimide (DCC) or 1-(3-dimethylaminopropyl)-3-ethylcarbodiimide (EDC) and 1-hydroxybenzotriazole (HOBt) in dimethylformamide (DMF) to give B. The Fmoc protecting group is removed with piperidine in DMF to yield free amine C. The next Fmoc-protected cyclic amino acid derivative D is coupled to C employing standard peptide (in this instance, 2-(1H-benzotriazol-1-yl)-1,1,3,3-tetramethyl-uronium hexafluorophosphate (HBTU), HOBt, and N,N-diisopropylethylamine (DIPEA) in DMF) to yield dipeptide E. The Fmoc group is removed with piperidine in DMF to yield the free amine F. A sulfonyl chloride, acyl chloride or isocyanate derivative is reacted with F in the presence of DIPEA to yield G. The final product is removed from the resin with strong acid (in this instance, trifluoroacetic acid (TFA) in the presence of thio-anisole and dithiane) to yield compounds of the present invention H.

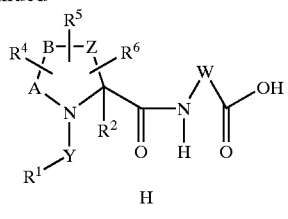

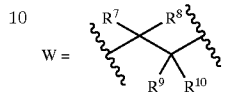

Compounds of the present invention may also be prepared by more traditional solution phase methodology outlined in Scheme 2. A N-tert-butyloxycarbonyl (t-Boc) protected cyclic amino acid derivative A is coupled to a acid-protected amino acid derivative B using a coupling agent such as dicyclohexylcarbodiimide (DCC) or 1-(3-dimethylaminopropyl)-3-ethylcarbodiimide (EDC) and 1-hydroxybenzotriazole (HOBt) and N-methylmorpholine (NMM) in methylene chloride ($CH_2Cl_2$) to give C. The t-Boc group is removed with hydrochloric acid in ethyl acetate to give the amine D. An acyl or sulfonyl chloride or isocyanate derivative is reacted with D in the presence of diethylamine and 4-dimethylaminopyridine (4-DMAP) to give E. The protecting group is removed from E employing an appropriate method to give F. Such methods would include a methyl ester being hydrolyzed with aqueous sodium hydroxide in ethanol (NaOH, EtOH), a benzyl ester being removed by catalytic hydrogenation ($H_2$, $Pt_2O/C$, EtOH), an allyl ester being removed under catalytic conditions in the presence of aqueous diethylamine ($Pd(OAc)_2$, aq. DIEA) or a tert-butyl ester being removed with excess strong acid (trifluoroacetic acid (TFA) or hydrochloric acid (HCl)).

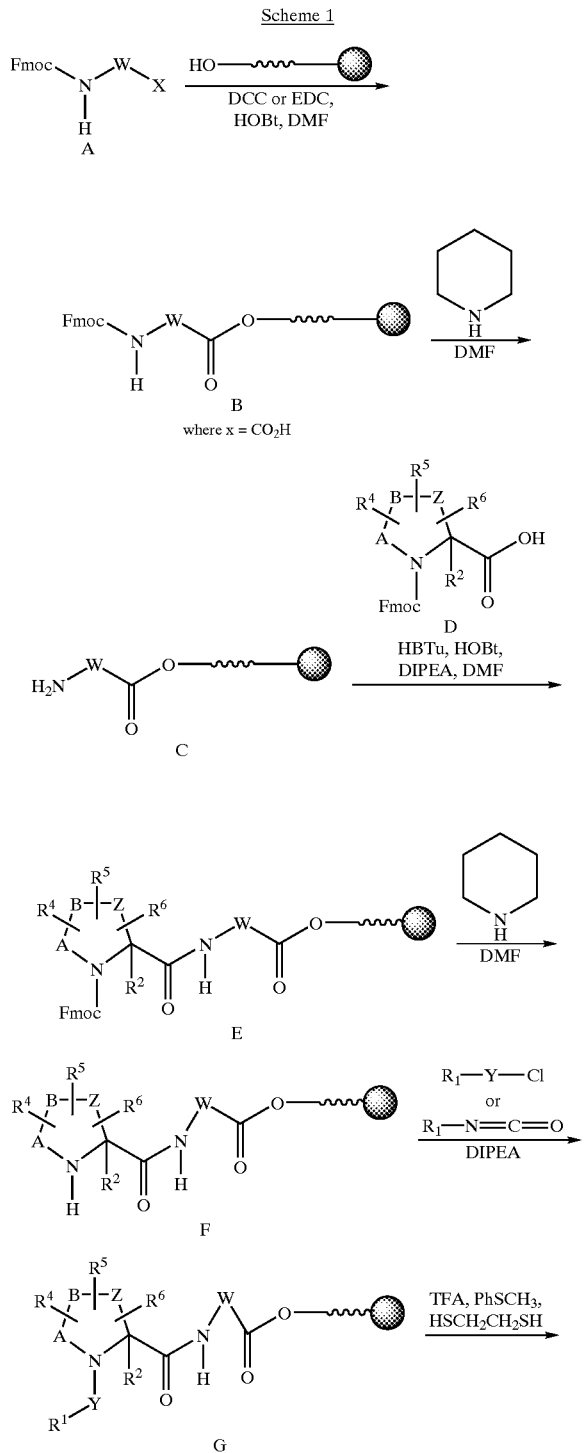

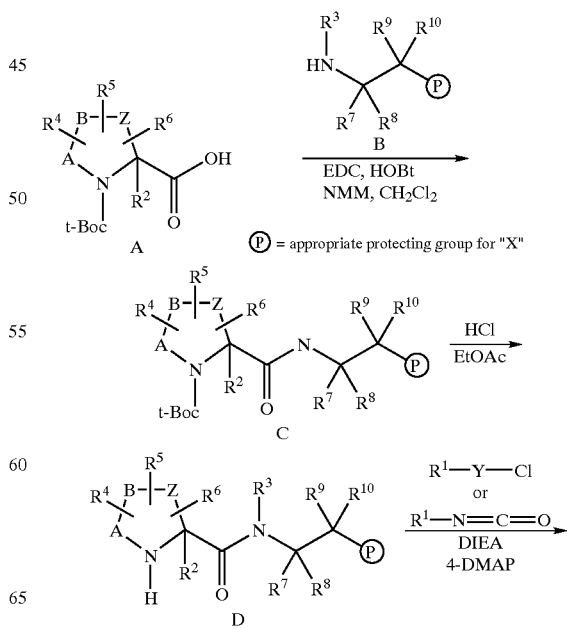

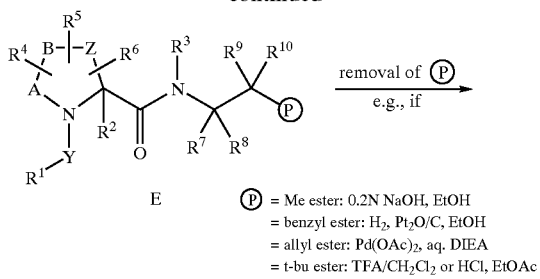

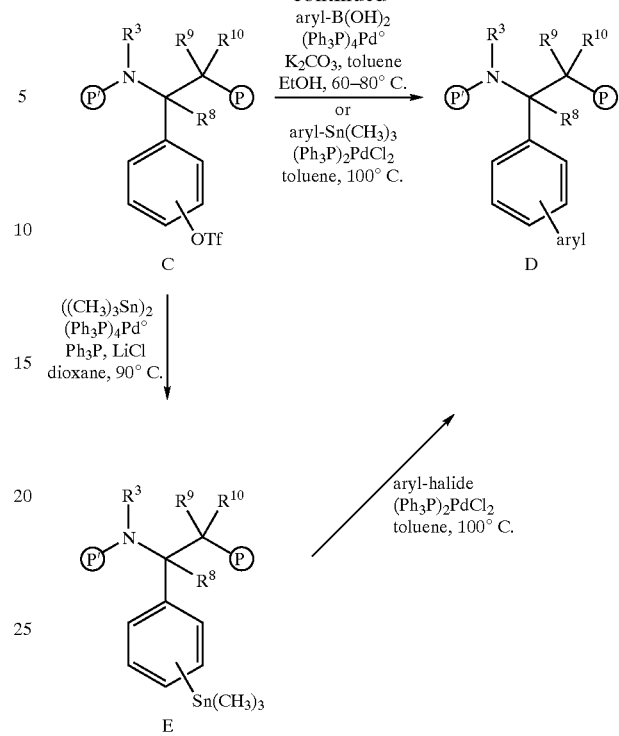

In the case where R7 is hydroxy-substituted aryl, methodology exists for the synthesis of other R7=alkoxy-aryl or biaryl as outlined in Scheme 3. An appropriately protected β-aryl-β-alanine derivative A may be O-alkylated with an electrophile ($R^d$=X where X is halide or sulfonate) to yield B which may be incorporated into the synthetic methodology outlined in Schemes 1 and 2. Alternatively, A may be treated with triflic acid anhydride in the presence of pyridine to yield triflate C. Triflate C may be reacted with an aryl boronic acid under Suzuki reaction conditions or with a aryl-stannane derivative under Stille conditions to yield biaryl D. Triflate C may also be converted to an aryl-stannane derivative by reaction with hexamethylditin, tetrakis(triphenyl)palladium(O), triphenylphoshine, lithium chloride in hot dioxane to afford E. Aryl-stannane E may be reacted with an aryl halide under Stille conditions to afford D. As with B, D may also be incorporated into the chemistry outlined in Schemes 1 and 2.

The following examples are provided to more fully illustrate the invention and are not to be construed as limiting the scope of the invention in any manner.

GENERAL PROCEDURE FOR THE SOLID-PHASE SYNTHESIS OF COMPOUNDS OF FORMULA I

Step A. Loading of N-Fmoc-amino Acid Derivatives Onto Resins.

N-Fmoc-amino acids were loaded on either Wang (Calbiochem-Novabiochem Corp.) or Chloro (2-chlorotrityl) resin. Wang resin, typically 0.3 mmol, was washed with dimethylformamide three times. A solution of N-Fmoc-amino acid (0.3 mmol) in dimethylformamide (3 mL) was transferred to the pre-swollen Wang resin. Dicyclohexylcarbodiimide (0.3 mmol) and 1-N-hydroxybenztriazole (0.3 mmol) was added and the mixture gently swirled for 2 hours. Following filtration, the resin was sequentially washed with dimethylformamide (3 times) and dichloromethane (3 times). The amino acid substitution value obtained after vacuum drying typically ranged between 0.07 to 0.1 mmol.

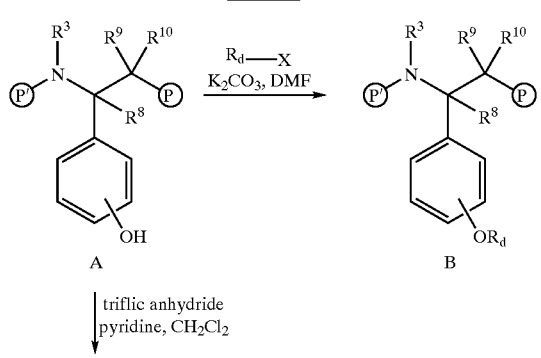

Scheme 3

Alternatively, Chloro (2-chorotrityl) resin, typically 0.2 mmol, was pre-swollen in dimethylformamide. A solution of N-Fmoc-amino acid (0.2 mmol) in dimethylformamide (3 ml) was added to the resin, followed by the addition of N,N-diisopropylethylamine(0.4 mmol). The resin was gently stirred for 2 hours, filtered and washed sequentially with dimethylformamide (3 times) and dichloromethane (3 times). The resin was finally washed with 10% methanol in dichloromethane and vacuum dried. The amino acid substitution value obtained after vacuum drying typically ranged between 0.05 to 0.1 mmol.

Step B. Deprotection of the N-Fmoc Group

The N-Fmoc protecting group was removed from the resin from Step A by treatment with 20% piperidine in dimethylformamide for 30 minutes. Following filtration, the resin was washed sequentially with dimethylformamide (3 times), dichloromethane (1 time) and dimethylformamide (2 times) and used in the subsequent reaction.

Step C. Coupling of the Next N-Fmoc-amino Acid Derivative

A solution of the next desired N-Fmoc-amino acid derivative (0.4 mmol) in dimethylformamide (2 mL) was mixed with 2-(1H-benzotriazol-1-yl)-1,1,3,3-tetramethyluronium hexafluorophosphate (0.4 mmol), 1-N-hydroxy-benztriazole (0.4 mmol) and diisopropylethylamine (0.6 mmol). This solution was transferred to resin from Step B and typically allowed to react for 2 hours. Couplings were monitored by ninhydrin reaction. The coupling mixture was filtered and the resin washed with dimethylformamide (3 times) and used in the subsequent reaction.

Step D. Deprotection of the N-Fmoc Group

The N-Fmoc protecting group was removed from the resin from Step C by the procedure described in Step B and used in the subsequent reaction.

Step E. Acylation (or Sulfonylation) of the Terminal Amino Group

The desired N-terminal capping reagent (sulfonylchloride or acylchloride) (0.4 mol) was dissolved in dimethylformamide (2 ml), mixed with N,N-diisopropylethylamine(0.8 mmol) and added to the resin from Step D. After approximately two hours, the resin was sequentially washed with dimethylformamide (3 times) and dichloromethane (3 times).

Step F. Cleavage of the Desired Products From the Resins

The final desired products were cleaved from the resins from Step E by gently stirring with a solution of trifluoroacetic acid:thioanisole:ethanedithiol (95:2.5:2.5); 3 hours for Wang resin and 30 minutes for the Chloro (2-chorotrityl) resin. Following filtration, the solvents were removed by evaporation and the residue dissolved in acetonitrile (3 mL). Insoluble material was removed by filtration. The final products were purified by reverse phase chromatography with a linear gradient of buffer A (0.1% trifluoroacetic acid in water) and buffer B (0.1% trifluoroacetic acid in acetonitrile) and isolated by lyophilization. Molecular ions were obtained by electrospray ionization mass spectrometry or matrix-assisted laser desorption ionization time-of-flight mass spectrometry to confirm the structure of each peptide.

EXAMPLES 1–10

The following compounds were prepared by the general procedure described above using the appropriate amino acid and sulfonyl chloride derivatives:

| Ex. No. | Name | MS* |
|---|---|---|
| (1) | N-((3,4-dimethoxybenzenesulfonyl)-1,2,3,4-tetrahydro-isoquinoline-3(S)-carbonyl)-3-amino-propionic acid | 449.1 |
| (2) | N-(4-(N'-2-chlorophenyl-ureido)phenylacetyl)-(S)-prolyl-3(S)-(3,4-methylenedioxyphenyl)-3-amino-propionic acid | |
| (3) | N-(3,5-dichlorobenzenesulfonyl)-(S)-prolyl-(L)-aspartic acid | 438.9 |
| (4) | N-(3,5-dichlorobenzenesulfonyl)-(S)-prolyl-3(R)-amino-trans-4-hexenoic acid | 435.0 |
| (5) | N-(3,5-dichlorobenzenesulfonyl)-(S)-prolyl-3(R)-amino-5-methylhexanoic acid | 450.9 |
| (6) | N-(3,5-dichlorobenzenesulfonyl)-(S)-prolyl-3(S)-amino-5-methylhexanoic acid | 451.2 |
| (7) | N-(3,5-dichlorobenzenesulfonyl)-(S)-prolyl-3(R)-amino-4-phenylbutanoic acid | 485.1 |
| (8) | N-(3,5-dichlorobenzenesulfonyl)-(S)-prolyl-3(R)-amino-3-phenylpropionic acid | 471.0 |
| (9) | N-(3,5-dichlorobenzenesulfonyl)-(S)-prolyl-3(S)-amino-3-phenylpropionic acid | |
| (10) | N-(3-chlorobenzenesulfonyl)-(S)-prolyl-3(R)-amino-3-phenylpropionic acid | |

*m/e: $(M + 1 (H^+))^+$ or $(M + 18 (NH_4^+))^+$

EXAMPLE 11

N-((3,4-Dimethoxybenzenesulfonyl)-1,2,3,4-tetrahydroisoguinoline-3(S)-carbonyl)-3(S)-(3,4-methylenedioxyphenyl)-3-amino-propioriic Acid Step A. N-(tert-Butyloxycarbonyl)-1,2,3,4-tetrahydroisoguinoline-3(S)-carbonyl-(S)-(3-amino-3-(3,4-methylenedioxyphenyl)-1-propanoic acid, Methyl Ester)

To a solution of N-(tert-butyloxycarbonyl)-1,2,3,4-tetrahydro-3-isoquinolinecarboxylic acid (254 mg, 0.916 mmol) in N,N-dimethylformamide (DMF) (2.5 mL) were added N-methylmorpholine (100 mL, 0.910 mmol), N-hydroxy-benzotriazole (185 mg, 1.37 mmol), and a solution of methyl (S)-3-amino-3-(3,4-methylenedioxy)phenyl-1-propanoate (prepared according to the procedures set forth in WO 96/22966) (205 mg, 0.918 mmol) in DMF (2.5 mL). After stirring at 0° C. for 10 min., EDC (210 mg, 1.10 mmol) was added. The cooling bath was removed after 5 minutes, and the mixture was stirred overnight at room temperature. It was then diluted with ethyl acetate, washed with water, 2N hydrochloric acid, saturated sodium hydrogencarbonate solution, saturated brine solution, dried (MgSO$_4$), and evaporated. Purification was achieved by means of silica gel chromatography eluting with 25% acetone/hexane; yield 388 mg (88%).

Step B. 1,2,3,4-Tetrahydroisoguinoline-3(S)-carbonyl-(S)-(3-amino-3-(3,4-methylenedioxyphenyl)-1-propanoic Acid, Methyl Ester, HCl Salt N-(tert-Butyloxycarbonyl)-1,2,3,4-tetrahydroisoguinoline-3(S)-carbonyl-(S)-(3-amino-3-(3,4-methylenedioxyphenyl)-1-propanoic acid, methyl ester) (350 mg, 0.725 mmol) was treated with 1M HCl in ethyl acetate (3.6 mL) overnight at room temperature. The mixture was evaporated and coevaporated several times with diethyl ether. The product was dried under high vacuum; yield 295 mg (97%).

Step C. N-(3,4-Dimethoxybenzenesulfonyl)-1,2,3,4-tetrahydroisoguinoline-3(S)-carbonyl-(S)-(3-amino-3-(3,4-methylenedioxyphenyl)-1-propanoic acid, methyl ester)

To a mixture of 1,2,3,4-tettahydroisoquinoline-3(S)-carbonyl-(S)-(3-amino-3-(3,4-methylenedioxyphenyl)-1-propanoic acid, methyl ester), hydrochloride (51 mg, 0.122 mmol) in methylene chloride (1.5 mL) were added N.N-diisopropylethylamine (63 mL, 0.361 mmol), DMAP (2 mg), and 3,4-dimethoxybenzenesulfonyl chloride (37 mg, 0.156 mmol). The reaction mixture was stirred overnight at room temperature. It was then diluted with methylene chloride, washed with water, 2$\underline{N}$ hydrochloric acid, saturated sodium hydrogencarbonate solution, saturated brine solution, dried ($MgSO_4$), and evaporated. Silica gel chromatography eluting with 30% acetone/hexane afforded pure title compound; yield 56.4 mg (80%).

Step D. N-(3,4-Dimethoxybenzenesulfonyl)-1,2,3,4-tetrahydroisoguinoline-3 (S)-carbonyl-3 (S)-amino-3-(3,4-methylenedioxyphenyl)-1-propanoic Acid A solution of N-(3,4-dimethoxybenzenesulfonyl)-1,2,3,4-tetrahydroisoquinoline-3(S)-carbonyl-(S)-(3-amino-3-(3,4-methylenedioxyphenyl)-1-propanoic acid, methyl ester) (50 mg, 0.086 mmol) in ethanol (3.5 mL) was treated with 0.2 $\underline{N}$ NaOH (0.55 mL, 0.110 mmol) for 4 hours at room temperature. The mixture was neutralized with several drops of glacial acetic acid and concentrated under diminished pressure. The residue was partitioned between methylene chloride and water. The organic layer was washed with saturated brine solution, dried ($Na_2SO_4$), and evaporated. The resulting amorphous solid was dried under high vacuum; yield 45 mg (92%).

Mass spectrum: m/e 569 (M+1); 400 MHz NMR ($CD_3OD$): δ 2.50 (dd, 1H), 2.70 (dd, 1H), 2.82 (dd, 1H), 3.01 (dd, 1H), 3.77 (s, 3H), 3.85 (s, 3H), 4.49 (t, 1H), 4.57 (s, 2H), 5.10 (t, 1H), 6.70–7.43 (m, 10H).

The following compound was prepared by the procedure described in Example 11 using the appropriate cyclic amino acid and sulfonyl chloride derivatives:

| Ex. No. | Name | MS* |
|---|---|---|
| (12) | N-(4-nitrobenzenesulfonyl)-(L)-pipecolyl-3(S)-(3,4-methylenedioxyphenyl)-3-amino-propionic acid | 506 |

*m/e: $(M + 1 (H^+))^+$ or $(M + 18 (NH_4^+))^+$

EXAMPLE 13

N-(3,5-Dichlorobenzenesulfonyl)-2(S)-methyl-prolyl-3(R)-amino-3-(4-fluorophenyl)-propionic Acid Step A. 3-(N-tert-Butyloxycarbonyl)amino-1-diazo-3-(4-fluorophenyl)propan-2-one To a solution of N-Boc-4-fluorophenylglycine (3.5 mmol, 0.94 g) in methylene chloride (15 mL) at 0° C. were added $\underline{N}$-methyl-morpholine (1.1 equiv; 3.84 mmol, 0.42 mL) and isobutyl chloroformate (1.05 equiv; 3.68 mmol, 0.48 mL) dropwise. While the reaction mixture was stirred at 0° C. for 1.0 h, precipitation of N-methylmorpholinium salt was observed. After 1 hr, the suspension was transferred via a Pasteur pipette to a solution of diazomethane (prepared by the decomposition of N-methyl-N-nitroso-p-toluenesulfonamide (0.02 mol, 4.3 g in 40 mL of diethyl ether) in a solution of potassium hydroxide (5.0 g) in ethanol (10 mL) and water (8 mL) at 70° C.) in diethyl ether at 0° C. After five minutes a saturated solution of sodium bicarbonate (50 mL) was added and vigorous stirring was continued for 15 min. The mixture was extracted with ethyl acetate (2×) and the combined organic extracts washed with brine. The solution was dried over anhydrous sodium sulfate, filtered and rotoevaporated to provide crude diazoketone (0.92 g, 90% yield) which was purified by flash silica gel chromatography eluting with a gradient of ethyl acetate (5–25%) in hexanes to yield the pure diazoketone (0.66 g, 65%).

$^1$NMR (400 MHz, $CDCl_3$): δ 7.30 (m, 2H), 7.05 (m, 2H ortho to F), 5.89 (brs, 1H 5.22 (brs, 1H), 5.15 (brs, 1H), 1.41 (s, 9H).

Step B. 3-(N-tert-Butyloxycarbonyl)amino-3-(4-fluorophenyl)-propionic Aicd, Methyl Ester To a solution of 3-(N-tert-butyloxycarbonyl)amino-1-diazo-3-(4-fluorophenyl)propan-2-one (1.7 mmol, 0.5 g) in a mixture of methanol (6 mL) and dioxane (6 mL) was added silver benzoate (0.15 equiv; 0.25 mmol, 0.57 mL of a solution made by dissolving 0.1 g in 1.0 mL of triethylamine) dropwise via syringe at ambient temperature. After evolution of nitrogen (bubbling) ceased (5–10 min), 10% ammonium hydroxide solution in saturated ammonium chloride solution (20 mL) was added and stirring was continued for 0.5 h. After this time, the reaction mixture was extracted with ethyl acetate (2×). The combined organic layer was washed with 1$\underline{N}$ hydrochloric acid, saturated bicarbonate solution, and brine. Finally, drying and concentration of the filtrate provided crude methyl ester (0.45 g, 94% yield) which was purified by flash silica gel chromatography eluting with a gradient of ethyl acetate (3 to 20%) in hexanes to yield pure methyl 'ester (0.42 g, 84%).

$^1$NMR (400 MHz, $CDCl_3$): δ 7.16 (m, 2H), 6.91(m, 2H ortho to F), 5.39 (brs, 1H), 4.97 (brs, 1H), 3.51 (s, 3H), 2.73 (m, 2H), 1.32 (s, 9H).

Step C. 3-Amino-3-(4-fluorophenyl)propionic Acid Methyl Ester

To the 3-(N-tert-butyloxycarbonyl)amino-3-(4-fluorophenyl)propionic acid, methyl ester (1.24 mmol, 0.37 g) was added 1N hydrochloric acid in ethyl acetate (5.0 equiv; 6.2 mmol, 6.2 mL) at 0° C. The resulting solution was stirred overnight at ambient temperature. A saturated solution of sodium bicarbonate was added (25 mL) and the quenched reaction mixture was extracted with ethyl acetate (3×). The combined organic layer was washed with brine, dried over anhydrous magnesium sulfate, filtered, and concentrated to provide an oil which was chromatographed on silica gel packed in $CH_2Cl_2$. Initial elution with $CH_2Cl_2$ until solvent front by-products were removed was followed by 2% MeOH in $CH_2Cl_2$ until product started to elute, and finally by 5 to 10% MeOH in $CH_2Cl_2$ to elute product completely. In this manner, the pure aminoester (0.18 g) was obtained in 74% yield.

$^1$NMR (400 MHz, $CDCl_3$): δ 7.33 (m, 2H), 7.01(m, 2H ortho to F), 4.42 (t, 1H, J=7.0 Hz), 3.67 (s, 3H), 2.64 (distorted dd, 2H) 1.99 (brs, 2H).

Step D. N-(tert-Butyloxycarbonyl)-2(S)-methyl-prolyl)-3(R)-amino-3-(4-fluorophenyl)propionic Acid, Methyl Ester To a solution of 3-amino-3-(4-fluorophenyl)propionic acid, methyl ester (0.24 mmol, 48 mg) in methylene chloride (1.0 mL) were added N-Boc-2(S)-methylproline (0.24 mmol, 55 mg) and $\underline{N,N}$-diisopropylethylamine (2.0 equiv; 0.48 mmol, 0.084 mL). After cooling in an ice-bath for 5 minutes, benzotriazol-1-yloxytripyrrolidino phosphonium hexafluorophosphate (PyBOP; 1.1 equiv; 0.26 mmol, 137 mg) was added. The cooling bath was removed and the resulting solution was stirred overnight under a nitrogen atmosphere. The reaction mixture was diluted with methylene chloride, washed with water, 1$\underline{N}$ hydrochloric acid, saturated sodium bicarbonate solution, and brine, dried over anhydrous magnesium sulfate, and rotoevaporated. Silica gel filtration eluting with 25% ethyl acetate in hexanes provided a mixture of two diastereomeric dipeptides (88 mg, 90% yield) which were separated by preparative HPLC (50% tert-butyl methyl ether, 50% hexanes; Waters PrepPak SiO$_2$ two 2×100 mm cartridges; flow rate: 16 mL/min; λ~210 nm). The major isomer (64 mg; 65% yield) was assigned the 3(R)-configuration on the basis of NMR spectra similarities with the corresponding des-fluoro compound prepared from commercial sources. The minor isomer (16 mg, 16% yield) was carried through the same sequence described below for the major isomer (~4: 1 ratio).

$^1$NMR (400 MHz, CDCl$_3$; major): δ 8.25 (brs, 1H of major rotamer), 7.15 (brs, 1H of minor rotamer), 7.22 (m, 2H), 6.96 (m, 2H ortho to F), 5.32 (m, 1H), 3.58 (s, 3H), 3.41 (m, 1H), 2.90 (m, 1H), 2.75. (dd, 1H, J=9.9, 4.0 Hz), 2.55 (brs, 1H of major rotamer), 2.19 (brs, 1H of minor rotamer), 1.75 (brm, 4H), 1.61 (brs, 3H of major rotamer), 1.57 (brs, 3H of minor rotamer), 1.41 (s, 9H).

$^1$NMR (400 MHz, CDCl$_3$; minor): δ 7.98 (brs, 1H of major rotamer), 7.30 (m, 2H), 7.00 (m, 2H ortho to F), 6.89 (brs, 1H of minor rotamer), 5.39 (m, 1H), 3.61 (s, 3H), 3.46 (m, 1H), 2.79 (m, 2H), 2.52 (brs, 1H of major rotamer), 2.28 (brs, 1H of minor rotamer), 1.55 (brm, 16H).

Step E. N-(3,5-Dichlorobenzenesulfonyl)-2(S)-methyl-prolyl-3(R)-amino-3-(4-fluorophenyl)propionic Acid N-(tert-Butyloxycarbonyl)-2(S)-methyl-prolyl)-3(R)-amino-3-(4-fluorophenyl)propionic acid, methyl ester (0.15 mmol, 60 mg) was dissolved in 1N hydrochloric acid in ethyl acetate (5.0 equiv; 0.75 mmol, 0.75 mL) and the resulting solution was stirred at ambient temperature overnight. During this period, a white precipitate formed and no starting material could be detected by TLC (50% ethyl acetate, 50% hexanes). Ethyl acetate was evaporated and the product salt was dried under high vacuum and used in the next step without further purification (52 mg, 100% yield).

To a mixture of the above hydrochloride salt (0.15 mmol, 52 mg) in CH$_2$Cl$_2$ (1.0 mL) at 0° C. were added N,N-diisopropylethylamine (3.0 equiv; 0.45 mmol, 0.08 mL), a solution of 3,5-dichlorobenzenesulfonyl chloride (1.1 equiv; 0.165 mmol, 40.5 mg) in methylene chloride (0.5 mL), and 4-dimethylaminopyridine (1.0 equiv; 0.15 mmol, 18.3 mg). The cooling bath was removed and the reaction mixture was stirred overnight at ambient temperature. It was then diluted with methylene chloride, washed with 1N hydrochloric acid, saturated sodium bicarbonate solution, saturated brine solution, dried over anhydrous magnesium sulfat, and rotoevaporated.

The desired sulfonamide was obtained pure (66 mg, 85% yield) by flash silica gel chromatography eluting with a gradient (5 to 35%) of ethyl acetate in hexanes.

N-(3,5-Dichlorobenzenesulfonyl)-2(S)-methyl-prolyl-3 (R)-amino-3-(4-fluorophenyl)propionic acid, methyl ester (0.12 mmol, 60 mg) was dissolved in methanol (1.5 mL) and treated with 0.25N sodium hydroxide solution (1.5 equiv; 0.18 mmol, 0.72 mL) for 5 h at ambient temperature. After this time, the reaction mixture was acidified with 1N hydrochloric acid and extracted with ethyl acetate (3×). The combined organic extracts were washed with brine, dried over anhydrous magnesium sulfate, filtered, and rotoevaporated to provide an oil which was purified by flash column chromatography on silica gel eluted first with methylene chloride, then with 1% methanol in methylene chloride, and finally with 3% methanol in methylene chloride containing 0.2% acetic acid. Traces of acetic acid were azeotropically removed by rotoevaporation with toluene affording pure N-(3,5-Dichlorobenzenesulfonyl)-2(S)-methyl-prolyl-3(R)-amino-3-(4-fluorophenyl)propionic acid (53 mg) in 88% yield.

MS: m/e 503 (M+H); 520 (M+H+NH$_3$) $^1$NMR (400 MHz, CDCl$_3$): δ 7.65 (d, 2H, J=1 Hz), 7.53 (t, 1H J=1 Hz), 7.30 (m, 2H), 7.00 (m, 2H ortho to F), 5.34 (m, 1H), 3.66 (m, 1H), 3.15 (m, 1H), 3.00 (dd, 1H , J=10.3, 3.5 Hz), 2.91 (dd, 1H, J=10.3, 3.8 Hz), 2.38 (m, 1H), 1.84 (m, 2H), 1.72 (m, 1H), 1.58 (s, 3H).

The following compounds were prepared by the procedure described in Example 13 using the appropriate amino acid and/or diastereomeric product:

| Ex. No. | Name | MS* |
|---|---|---|
| (14) | N-(3,5-dichlorobenzenesulfonyl)-(S)-prolyl-3(R)-amino-4-(2-naphthyl)-butanoic acid | 536 |
| (15) | N-(3,5-dichlorobenzenesulfonyl)-(S)-prolyl-3(R)-amino-3-(4-fluorophenyl)propionic acid | 489 |
| (16) | N-(3,5-dichlorobenzenesulfonyl)-(S)-prolyl-3(S)-amino-3-(4-fluorophenyl)propionic acid | 489 |
| (17) | N-(3,5-dichlorobenzenesulfonyl)-(S)-prolyl-3(R)-amino-4-(4-fluorophenyl)butanoic acid | 503 |
| (18) | N-(3,5-dichlorobenzenesulfonyl)-2(S)-methyl-prolyl-3(R)-amino-4-(4-fluorophenyl)butanoic acid | 517 |
| (19) | N-(3,5-dichlorobenzenesulfonyl)-2(S)-methyl-prolyl-3(S)-amino-3-(4-fluorophenyl)propionic acid | 503 |
| (20) | N-(3,5-dichlorobenzenesulfonyl)-(S)-prolyl-3(S)-amino-3-(2'-methoxy-4-biphenylmethyl)propionic acid | 591 |
| (21) | N-(3,5-dichlorobenzenesulfonyl)-2(S)-methyl-prolyl-3(S)-amino-5-(phenyl)pentanoic acid | 513 |

*m/e: (M + 1 (H$^+$))$^+$ or (M + 18 (NH$_4^+$))$^+$

EXAMPLE 22 and 23

N-(3,5-Dichlorobenzenesulfonyl)-2(S)-prolyl-3(R)-amino-3-(4-biphenyl)propionic Acid and N-(3,5-Dichlorobenzenesulfonyl)-2(S)-prolyl-3(S)-amino-3-(4-biphenyl)propionic Acid Step A. N-tert-Butoxycarbonyl-(S)-4-hydroxyphenylglycine To a solution of (S)-(4-hydroxyphenyl)glycine (Sigma Chemical) ((6.5 g, 39 mmol) in dioxane/water (1:1, 120 mL) was added triethylamine (5,9 g, 8.2 mL, 58 mmol) and [2-(tert-butoxycarbonyloxyimino)-2-phenylacetonitrile] (BOC—ON; 11 g, 45 mmol). After stirring overnight at room temperature, 300 mL of brine was added to the solution and the mixture was extracted with ether. (3×100 mL). The aqueous layer was acidified with HCl (pH=2) and extracted with 3×100 mL of ethyl acetate. The ethyl acetate layer was dried over MgSO$_4$, filtered and the solvent removed under reduced pressure. The residue was chromatographed with 98/2 to 95/5 methylene chloride/methanol. Recovered 12 g of crude product. The impurity was removed following esterification of the product in the next step.

400 MHz $^1$H NMR (CDC$_3$): δ 1.37 (s, 9H), 5.1 (1H, br s), 6.7 (d, 2H, J=8 Hz), 7.15 (d, 2H, J=8 Hz).

Step B. N-tert-Butoxycarbonyl-(S)-4-hydroxyphenylglycine,Methyl Ester

In a 50 mL round bottomed flask was added a 1:1 mixture of benzene:methanol and N-tert-butoxycarbonyl-(S)-4-hydroxyphenylglycine (2.8 g, 11 mmol). The solution was cooled to 0° C. and a 2 M solution of trimethylsilyldiazomethane (Aldrich Chemical Co.) in hexane was added with vigorous stirring until a slight yellow color persisted. Then the reaction mixture solvents were removed under reduced pressure and the crude product was purified by flash chromatography (80/20 hexane/ethyl acetate) to give N-tert-butyloxycarbonyl-(S)-4-hydroxyphenylglycine, methyl ester (2.05 g, 7.3 mmol) (66% yield).

300 MHz ¹H NMR (CDCl₃): δ 1.43 (s, 9H), 3.71 (s, 3H), 5.22 (br d, 1H), 5.57 (1H, br d), 5.80 (br s, 1H), (6.7 (d, 2H, J=8 Hz), 7.17 (d, 2H, J=8 Hz).

Step C. N-tert-Butoxycarbonyl-(S)-4-trifluoromethylsulfonyloxyphenylglycine, Methyl Ester To a 25 mL round bottom flask fitted with a stir bar and septum was added N-tert-butyloxycarbonyl-(S)-4-hydroxyphenylglycine, methyl ester (1.9 g, 6.8 mmol) and pyridine (2.8 mL, 33 mmol) in 12 mL of methylene chloride. The flask was purged with N₂, cooled to 0° and trifluoromethanesulfonic anhydride (1.38 mL, 7.8 mmol) was added dropwise over several minutes, keeping the temperature at or below 4° C. The solution was stirred for 1 h, then at room temperature for 4 h. The mixture was diluted with 20 mL of methylene chloride. The mixture was washed with mL of 0.5 N NaOH, 1×20 mL of water and 2×20 mL of 10% citric acid. Dry the organic layer over MgSO₄, filter, reduce the volume. Flash chromatography (75/25 hexane/methylene chloride) gave 2.3g of desired product (81% yield).

300 MHz ¹H NMR (CDCl₃): δ 1.43 (s, 9H), 3.74 (s, 3H), 5.35 (1H, br d), 5.68 (br s, 1H), 7.27 (d, 2H, J=8 Hz), 7.47 (d, 2H, J=8 Hz).

Step D. N-tert-Butoxycarbonyl-(S)-(4-biphenyl)glycine.

To a 25 mL round bottom flask fitted with a stir bar and septum was added N-tert-butyloxycarbonyl-(S)-4-trifluoromethylsulfonyloxyphenylglycine, methyl ester (690 mg, 1.67 mmol), anhydrous potassium carbonate (348 mg, 2.6 mmol) and benzeneboronic acid (411 mg, 3.4 mmol) in 15 ml of toluene and 3 mL of ethanol. The mixture was degassed under nitrogen with three freeze-thaw cycles and tetrakis(triphenylphosphine) palladium (94 mg, 0.085 mmol) was added to the reaction mixture and the mixture was heated between 75–90° C. for 4 h. The solvent was removed under reduced pressure and the residue flash chromatographed with 85/15 hexane/ethyl acetate. Recovered 600 mg of the methyl ester (quantitative yield).

300 MHz ¹H NMR (CDCl₃): δ 1.44 (s, 9H), 3.75 (s, 3H), 5.37 (1H, br d), 5.62 (br s, 1H), 7.36 (m,. 1H), 7.45 (m, 4H), 7.57 (m, 4H).

The ester was hydrolyzed with 1.2 eq of KOH in 10 mL of 4:1 ethanol: water (2 h). The solution was acidified with 2 N HCl (pH=2). Rᵉmove the solvents in vacuo and extract the free acid with methylene chloride. Recovered 430 mg of free acid (66% yield).

Step E. 3-(N-tert-Butyloxycarbonyl)amino-1-diazo-3-(4-biphenyl)propan-2-one.

To a 25 mL round bottom flask fitted with a stir bar and septum was added N-tert-butoxycarbonyl-(S)-4-biphenylglycine (430 mg, 1.31 mmol) in 10 mL of 2:1 methylene chloride: ether. The mixture was cooled to 0° C. and N-methylmorpholine (159 µl, 1.44 mmol) was added, followed by dropwise addition of isobutylchloroformate (179 µl, 1.38 mmol). The mixture was stirred for 1 h at 0° C., then diazomethane in ether (excess, prepared from Diazald^R by literature procedure) was added dropwise to the reaction mixture. The mixture was stirred for 1 h then quenched with saturated sodium bicarbonate. The mixture was extracted with ethyl acetate. (2×5 mL), washed with brine then dried over MgSO₄. The mixture was filtered, the solvent removed under reduced pressure and the product isolated by flash chromatography (80/20 hexane/ethyl acetate) to give 280 mg (0.78 mmol) of product (58% yield).

300 MHz ¹H NMR (CDCl₃): δ 1.42 (s, 9H), 5.22 (bs, 1H), 5.29 (s, 1H), 5.9 (br s, 1H) 7.35–7.5 (m, 5H), 7.52–7.62 (m, 4H).

Step F. 3(R)-Amino-3-(4-biphenyl)propionic acid, Methyl Ester

To a 25 mL round bottom flask fitted with a stir bar and septum was added (3-diazo-2-oxopropyl-1-(S)-(4-biphenyl))carbamic acid,tert-butyl ester (280 mg, 0.76 mmol),with 5 mL each of methanol and dioxane. The flask was cooled to 0° C. and 0.15 eq (34 mg, 0.038 mmol) of silver benzoate in 500 µl of triethylamine was added dropwise to the reaction mixture and the mixture allowed to stir at 25° C. for 1 h. The reaction was worked up with 10% NH₄OH in saturated NH₄Cl (10 mL). Extract with ether (3×10 mL) and dry the organic layer over MgSO₄. Filter, reduce the volume and flash chromatograph with 85/15 hexane/ethyl acetate. Recovered 260 mg of product (98% yield). Take this material and dissolve it in 10 mL of 1 N HCl in ethyl acetate. After stirring 2 h at room temperature, we obtained 180 mg of 3(R)-amino-(4-biphenyl)propionic acid, methyl ester hydrochloride. 300 MHz ¹H NMR (CD₃OD): δ 6 2.90 (dd, 1H, J=18 Hz, J=6 Hz), 3.02 (dd, 1H, J=18 Hz, J=6 Hz), 3H), 5.9 (br s, 1H), 7.33–7.5 (m, 5H), 7.55–7.6 (m, 4H).

Step G. N-(3,5-Dichlorobenzenesulfonyl)-(L)-proline

To a mixture of (L)-proline methyl ester hydrochloride (838 mg, 5.06 mmol) in methylene chloride (25 mL) at 0° C. were added N,N-diisopropylethylamine (2.64 mL, 15.2 mmol) and a solution of 3,5-dichlorobenzenesulfonyl chloride (1.49 g, 6.07 mmol) in methylene chloride (5 mL). The cooling bath was removed, and the mixture was stirred overnight at room temperature. It was then diluted with methylene chloride, washed with 1N hydrochloric acid, saturated NaHCO₃, saturated brine solution, dried (Na₂SO₄), and evaporated. The methyl ester was obtained pure by silica gel chromatography eluting with 10% acetone in hexane; yield 1.49 g. It was then taken up in ethanol (50 mL) and treated with 0.2 N sodium hydroxide (26.6 mL) for 1.5 hours at room temperature. The mixture was acidified with glacial acetic acid, concentrated, the residue taken up in methylene chloride, washed with water, saturated brine solution, dried (Na₂SO₄), and evaporated to give the title compound; yield 1.4 g.

400 MHz ¹H NMR (CD₃OD): δ 1.80–2.15 (m, 4H); 3.35–4.45 (m, 2H); 4.30 (dd, 1H); 7.76 (m, 1H); 7.83 (m, 2H).

Step H. N-(3,5-Dichlorobenzenesulfonyl)-2(S)-prolyl-3(R)-amino-3-(4-biphenyl)propionic Acid, Methyl Ester and N-(3,5-dichlorobenzenesulfonyl)-2(S)-prolyl-3(S)-amino-3-(4-biphenyl)propionic Acid, Methyl Ester.

To a 10 mL round bottom flask fitted with a stir bar and septum was added 3(R)-amino-3-(4-biphenyl)propionic acid (92 mg, 0.36 mmol), N-methylmorpholine (99 µl, 0.7 mmol), 1-hydroxybenzotriazole hydrate.(75 mg, 0.55 mmol) and N-(3,5-dichlorobenzenesulfonyl)-2(S)-proline (125 mg, 0.43 mmol) in 5 ml of methylene chloride. Then 1-ethyl-3-(3-dimethylaminopropyl)carbodiimide hydrochloride (83 mg, 0.43 mmol) was added and the mixture stirred overnight at 24° C. The reaction mixture was worked up by adding 0.5 N HCl (pH=3) and extracting with methylene chloride. The solvent was removed and the residue flash chromatographed (70/30) to give two products: 60 mg of the higher Rf product N-(3,5-dichlorobenzenesulfonyl)-2(S)-prolyl-3(R)-amino-3-(4-biphenyl)propionic acid, methyl ester.

400 MHz ¹H NMR (CDCl₃): δ 1.7–1.9 (m, 4H), 2.2–2.3 (bs, 1H), 2.9–3.1 (m, 2H), 3.3–3.3 (m, 1H), 3.65 (s, 3H), 4.05–4.15 (m, 2H), 5.4–5:5 (m, 1H), 7.22 (m, 1H), (m, 4H), 7.55 (m, 4H), 7.72 (d, 1H, J=6Hz), 7.8 (m, 1H); and 60 mg of the lower Rf product N-(3,5-dichlorobenzenesulfonyl)-2 (S)-prolyl-3(S)-amino-3-(4-biphenyl)propionic acid, methyl ester.

400 MHz $^1$H NMR (CDCl$_3$): δ 1.7–1.9 (m, 5H), 2.2–2.3 (bs, 1H), 2.9 (d, 2H, J=8 Hz), 3.1–3.3 (m, 1H), 3.65 (s, 3H), 4.08–4.16 (m, 1H), 5.4–5.5 (m, 1H), 7.25–7.35 (m, 1H), 7.4(bd, 4H), 7.55 (bd, 3H), 7.71 (m, 3H).

Step I. N-(3,5-Dichlorobenzenesulfonyl)-2(S)-prolyl-3(R)-amino-3-(4-biphenyl)propionic Acid, and N-(3,5-dichlorobenzenesulfonyl)-2(S)-prolyl-3(S)-amino-3-(4-biphenyl)propionic Acid Each of the components described in Step H was hydrolyzed separately to the free acid by adding to each 2 equivalents of KOH in 3/1 ethanol/water. The solutions were acidified with 2.5 N HCl and each component was extracted with methylene chloride. Forty five mg of the higher Rf product N-(3,5-dichlorobenzenesulfonyl)-2(S)-prolyl-3(R)-amino-3-(4-biphenyl)propionic acid was recovered.

400 MHz $^1$H NMR (CDCl$_3$): δ 1.75 (m, 1H), 2.0 (m, 3H), 2.9–3.1 (m, 2H), 3.2 (m, 1H), 3.60 (m, 1H), 4.2 (m, 1H), 5.4–5.5 (m, 1H), 7.3 (m, 1H), 7.41(m, 2H), 7.46 (d, 1H, J=2 Hz), 7.48 (d, 1H, J=2 Hz), 7.60 (t, 1H, J=2 Hz), 7.60 (t, 1H, J=2 Hz), (d, 1H, J=2 Hz), 7.87, (t, 2H, J=2 Hz). 8.7 (d, 1H, J=9 Hz). MS: m/e 565(M+H+NH$_3$).

Thirty mg of the lower Rf product N-(3,5-dichlorobenzenesulfonyl)-2(S)-prolyl-3(S)-amino-3-(4-biphenyl)propionic acid was recovered.

400 MHz $^1$H NMR (CDCl$_3$): δ 1.75 (m, 1H), 2.0 (m, 3H), 2.87 (d, 2H, J=6Hz), 3.2 (m, 1H), 3.60 (m, 1H), 4.2 (m, 1H), 5.35–5.45 (m, 1H), 7.3 (t, 1H, J=6 Hz), 7.41(t, 2H, J=6 Hz), 7.46 (d, 2H, J=6 Hz), 7.59 (d, 4H, J=8 Hz), 7.79 (d, 1H, J=2 Hz), 997, (d, 2H, J=2 Hz). 8.67 (d, 1H, J=9 Hz). MS: m/e 565(M+H+NH$_3$).

EXAMPLE 24 and 25

N-(3,5-Dichlorobenzenesulfonyl)-2(S)-prolyl-3(R)-amino-3-(4-(2'-methoxyphenyl)phenyl)propionic Acid and N-(3,5-dichlorobenzenesulfonyl)-2(S)-prolyl-3(S)-amino-3-(4-(2'-methoxyphenyl)phenyl) propionic Acid Step A. N-tert-Butoxycarbonyl-(S)-4-(2'-methoxyphenyl) phenylglycine.

The title compound was synthesized by the procedure described in Example 22 and 23, Step D by coupling N-(tert-butoxycarbonyl)-(S)-4-(trifluoromethylsulfonyloxy) phenylglycine, methyl ester (413 mg. 1.0 mmol) with 2-methoxybenzeneboronic acid (304 mg, 2.0 mmol) to provide 310 mg of the methyl ester product (81% yield).

300 MHz $^1$H NMR (CDCl$_3$): δ 1.45 (s, 9H), 3.74 (s, 3H), 3.81 (s, 3H), 5.42 (bd, 1H), 5.55 (bs, 1H), 5.7 (br s, 1H), 6.95–7.05 (m, 1H), 7.25–7.3 (m 3H), 7.4 (d, 1H, J=8Hz), 7.48–7.52 (m, 3H).

This material was hydrolyzed to the free acid and used without further purification in the next step.

Step B. 3(S)-(N-tert-Butyloxycarbonyl)amino-1-diazo-3-(4-(2'-methoxyphenyl)phenyl)-propan-2-one.

The title compound was synthesized by the procedure described in Example 22 and 23, Step E by transforming N-tert-butoxycarbonyl-(S)-4-(2'-methoxyphenyl) phenylglycine (220 mg, 0.62 mmol) to the methyldiazoketone via the Arnt-Eistert reaction to provide 120 mg (51% yield) of the homologated methyl ester.

400 MHz $^1$H NMR (CDCl$_3$): δ 1.41 (bs, 9H), 3.79 (s, 3H), 5.22 (bs, 1H), 5.29 (s, 1H), 5.85 (br s, 1H), 6.95–7.05 (m, 2H), 7.25–7.35 (m 4H), 7.5 (d, 2H, J=9 Hz).

Step C. 3(R)-Amino-3-(4-(2'methoxyphenyl)phenyl) propionic Acid, Methyl Ester Hydrochloride The title compound was synthesized by the procedure described in Example 22 and 23, Step F by effecting a Wolff rearrangement on (3-diazo-2-oxopropyl-1-(S)-(4-(2'methoxyphenyl)phenyl))carbamic acid, tert butyl ester (120 mg, 0.31 mmol) to give homologated Boc-β-aminoacid methyl ester.

400 MHz $^1$H NMR (CDCl$_3$): δ 1.41 (bs, 9H), 2.8–2.9 (m, 2H), 3.62 (s, 3H), 3.79 (s, 3H), 5.10 (bs, 1H), 5.45 (bs, 1H), 5.85 (br s, 1H), 6.95–7.05 (m, 2H), 7.25–7.35 (m 4H), 7.48 (d, 2H, J=9 Hz).

This material was dissolved in 10 mL of 1 N HCl in ethyl acetate. After stirring 2 h at room temperature, 45 mg of 3(R)-amino-3-(4-(2'-methoxy)-biphenyl)propionic acid, methyl ester hydrochloride was obtained. This material was carried on to the next step without further characterization.

Step D: N-(3,5-Dichlorobenzenesulfonyl)-2(S)-prolyl-3(R)-amino-3-(4-(2'-methoxyphenyl)phenyl)propionic Acid, Methyl Ester and N-(3,5-dichlorobenzenesulfonyl)-2(S)-prolyl-3(S)-amino-3-(4-(2'-methoxyphenyl)phenyl) propionic Acid, Methyl ester The title compounds were synthesized by the procedure described in Example 22 and 23, Step H by effecting the coupling reaction of 3(R)-amino-3-(4-(2'-methoxyphenyl) phenyl)propionic acid hydrochloride (48 mg, 0.13 mmol) with N-(3,5-dichlorobenzenesulfonyl)-2(S)-proline (49 mg, 0.15 mmol). Two products were obtained: 33 mg of the higher Rf product N-(3,5-dichlorobenzenesulfonyl)-2(S)-prolyl-3(R)-amino-3-(4-(2'-methoxybiphenyl)propionic acid, methyl ester.

400 MHz $^1$H NMR (CDCl$_3$): δ 1.7–1.9 (m, 3H), 2.2–2.3 (bs, 1H), 2.92 (dd, 1H, J=16 Hz, J=6 Hz), 3.02 (dd, 1H, J=16 Hz, J=6 Hz), 3.1–3.2 (m, 1H), 3.65 (m, 1H), 3.67 3H), 3.80 (s, 3H), 4.05–4.15 (m, 2H), 5.4–5.5 (m, 1H), 6.9–7.0 (m, 2H), 7.3H), 7.50 (d, 2H, J=8 Hz), 7.60 (t, 1H, J=2 Hz), 7.72 (d, 1H, J=1 Hz), 7.8 (m, 1H); and 11 mg of the lower Rf product N-(3,5-dichlorobenzenesulfonyl)-2(S)-prolyl-3(S)-amino-3-(4-(2'-methoxyphenyl)phenyl)propionic acid, methyl ester.

400 MHz $^1$H NMR (CDCl$_3$): δ 1.7–1.9 (m, 3H), 2.2–2.3 (bs, 1H), 2.83 (d, 1H, J=6 Hz), 2.9 (d, 1H, J=8 Hz), 3.1–3.2 (m, 1H), 3.67 (s over m, 4H), 3.79 (s, 3H), 4.08–4.16 (m, 1H), 5.4–5.5 (m, 1H), 6.9–7.0 (m, 2H), 7.15 (d, 1H, J=9 Hz), 7.25–7.3 (m, 2H), 7.35 (m, 2H), 7.50 (d, 2H, J=8 Hz), 7.60 (t, 1 H, J=2 Hz), 7.72 (d, 1H, J=1 Hz).

Step E. N-(3,5-Dichlorobenzenesulfonyl)-2(S)-prolyl-3(R)-amino-3-(4-(2'-methoxyphenyl)phenyl)propionic Acid and N-(3,5-dichloro-benzenesulfonyl)-2(S)-prolyl-3(S)-amino-3-(4-(2'-methoxyphenyl)-phenyl)propionic Acid.

Each of the components described in Step D. was hydrolysed separately to the free acid by adding to each 2 equivalents of KOH in 3/1 ethanol/water. The solutions were acidified with 2.5 N HCl and each component was extracted with methylene chloride. Each component was flash chromatographed using 97/3/0.2 methylene chloride/methanol/acetic acid. Twenty mg of the higher Rf product N-(3,5-dichlorobenzenesulfonyl)-2(S)-prolyl-3(R)-amino-3-(4-(2'-methoxyphenyl)phenyl)propionic acid was recovered.

400 MHz $^1$H NMR (CD$_3$OD): δ 1.7–1.9 (m, 4H), 2.8–2.95 (m, 2H), 3.65 (m, 1H), 3.77 (s, 3H), 4.05–4.15 (m, 2H), 5.4–5.5 (m, 1H), 6.95–7.05 (m, 2H), 7.25–7.30 (m, 21H), 7.4–7.5 (m, 4H), 7.78 (t, 1H, J=1 Hz), 7.86 (d, 1H, J=2 Hz). MS: m/e 594(M+1+NH$_3$).

Six mg of the lower Rf product N-(3,5-dichlorobenzenesulfonyl)-2(S)-prolyl-3(S)-amino-3-(4-(2'-methoxyphenyl)phenyl)propionic acid was recovered.

400 MHz $^1$H NMR (CD$_3$OD): δ 1.7–1.8 (m, 1H), 2.0 (m, 2H), 2.86 (d, 1H, J=3.77 3.3–3.4 (m, 1H), 3.5–3.6 (m, 1H), 3.77 (s, 3H), 4.25 (m, 1H), 5.4–5.5 (m, 2H), 7.25–7.3 (m, 2H), 7.40 (d, 2H, J=8 Hz), 7.48(d, 2H, J=8 Hz), 7.72 J=1 Hz), 7.80 (d, 2H, J=1 Hz). MS: m/e 594(M+1+NH$_3$).

EXAMPLE 26 and 27

N-(3,5-Dichlorobenzenesulfonyl)-2(S)-prolyl-3(R)-amino-3-(4-hydroxy-phenyl)propionic Acid and N-(3,5-Dichlorobenzenesulfonyl)-2(S)-prolyl-3(S)-amino-3-(4-hydroxyphenyl)propionic Acid Step A. N-tert-Butoxycarbonyl-(S)-4-(tert-butyldimethylsilyloxyphenylglycine To a 100 mL round bottom flask fitted with a stir bar and septum was added N-tert-butoxycarbonyl-(S)-4-hydroxyphenylglycine (5.34 g, 20 mmol, prepared in Example 22 and 23, Step A), imidazole (8.17 g, 120 mmol) and dimethylformamide (80 mL). Then tert-butyldimethylsilyl chloride (3.64 g, 24 mmol) was added portionwise, the flask stoppered and the mixture stirred for seven days. The DMF was distilled under vacuum and the residue redissolved in 100 mL of ethyl acetate. The organic layer was washed consecutively with water (3×25 mL) and brine (2×50 mL), dried over $MgSO_4$, filtered and the solvent removed under reduced pressure. The residue was flash chromatographed (97/3/0.2 methylene chloride/methanol/acetic acid ) to afford 2.5 g of product (34% yield).

300 MHz $^1$H NMR (CDCl$_3$): δ 0.18 (s, 6H), 0.96 (s, 9H), 1.4 (s, 9H), 5.2 (1H, br s) 5.4 (bs, 1H), 6.78 (d, 2H, J=8 Hz), 7.21 (d, 2H, J=8 Hz).

Step B. 3(S)-(N-tert-Butyloxycarbonyl)amino-1-diazo-3-(4-(tert-butyldimethylsilyloxy)phenyl)-propan-2-one.

The title compound was synthesized by the procedure described in Example 22, 23, Step E. by converting N-tert-butoxycarbonyl-(S)-4-tert-butyl-dimethylsilyloxyphenylglycine (630 mg, 1.65 mmol) to the diazoketone 3-diazo-2-oxopropyl-1-(S)-(4-hydroxyphenyl)) carbamic acid,tert-butyl ester (250 mg, 35% yield).

300 MHz $^1$H NMR (CDCl$_3$): δ 0.18 (s, 6H), 0.97 (s, 9H), 1.40 (s, 9H), 5.1 (bs, 5.19 (bs, 1H), 5.7 (br s, 1H), 6.78 (d, 2H, J=8 Hz), 7.14 (d, 2H, J=8 Hz).

Step C. 3(R)-Amino-3-(4-tert-butyldimethylsilyloxyphenyl) Propionic Acid, Methyl Ester The title compound was synthesized by the procedure described in Example 22 and 23, Step F. by converting (3-diazo-2-oxopropyl-1-(S)-(4-tert-butyldimethylsilyloxyphenyl))carbamic acid,tert-butyl ester (250 mg, 0.61 mmol) to to give the title homologated Boc-β-aminoacid methyl ester 3(R)-amino-(4-tert-butyl-dimethylsilyloxyphenyl)propionic acid, methyl ester (150 mg, 60% yield).

300 MHz $^1$H NMR (CDCl$_3$): δ 0.19 (s, 6H), 0.97 (s, 9H), 1.40 (s, 9H), 3.59 (s, 2H), 5.0 (bs, 1H), 5.3 (bs, 1H), 6.78 (d, 2H, J=8 Hz), 7.14 (d, 2H, J=8 Hz).

This material was dissolved in 5 mL of 1 N HCl in ethyl acetate. After stirring 2 h at room temperature, we obtained 120 mg of 3(R)-amino-3-(4-tert-butyldimethylsilyl-oxyphenylphenyl)propionic acid, methyl ester hydrochloride (quantitative yield).

This material was carried on to the next step without further characterization.

Step D. N-(3,5-Dichlorobenzenesulfonyl)-2(S)-prolyl-3(R)-amino-3-(4-tert-butyldimethylsilyloxyphenyl)propionic acid, methyl ester and N-(3,5-dichlorobenzenesulfonyl)-2(S)-prolyl-3(S)-amino-3-(4-tert-butyldimethylsilyloxyphenyl)propionic acid, Methyl Ester.

The title compounds were synthesized by the procedure described in Example 22 and 23, Step H by effecting the coupling reaction of 3(R)-amino-3-(4-tert-butyldimethylsilyloxyphenyl)propionic acid hydrochloride (220 mg, 0.64 mmol) with N-(3,5-dichlorobenzenesulfonyl)-2(S)-proline (230 mg, 0.7 mmol). Two products were obtained; 84 mg of the higher Rf product N-(3,5-dichlorobenzene-sulfonyl)-2(S)-prolyl-3(R)-amino-3-(4-tert-butyldimethylsilyloxyphenyl)propionic acid, methyl ester.

400 MHz $^1$H NMR (CDCl$_3$): δ 0.17 (s, 6H,), 0.95 (s, 9H), 1.7–1.8 (m, 3H), 2.15–2.25 (bs, 1H), 2.85 (dd, 1H, J=16 Hz, J=6 Hz), 2.95 (dd, 1H, J=16 Hz, J=6 Hz), 3.1–3.2 (m, 1H), 3.63 (m, 1H), 3.62 (s, 3H), 4.05–4.15 (m, 1H), 5.3–5.4 (m, 1H), 6.78 (d, 2H, J=7 Hz), 7.12 (d, 2H, J=7 Hz), 7.60 (t, 1H, J=2 Hz), 7.67 (m, 1H), 7.71 (d, 1H, J=1 Hz); and 60 mg of the lower Rf product N-(3,5-dichlorobenzenesulfonyl)-2(S)-prolyl-3(S)-amino-3-(4-tert-butyldimethylsilyloxyphenyl) propionic acid, methyl ester.

400 MHz $^1$H NMR (CDCl$_3$): δ 0.16 (s, 6H,), 0.95 (s, 9H), 1.6–1.9 (m, 3H), 2.2–2.3 (bs, 1H), 2.82 (d, 2H, J=8 Hz), 3.1–3.2 (m, 1H), 3.62 (m, 1H), 3.63 (s, 3H, 4.05–4.15 (m, 1H), 5.3–5.4 (m, 1H), 6.80 (d, 2H, J=7 Hz), 7.19 (d, 2H, J=7 Hz), 7.60 (t, 1H, J=2 Hz), 7.62 (m, 1H), 7.72 (d, 1H, J=1 Hz).

Step E. N-(3,5-Dichlorobenzenesulfonyl)-2(S)-prolyl-3(R)-amino-3-(4-hydroxyphenyl)propionic Acid and N-(3,5-dichlorobenzenesulfonyl)-2(S)-prolyl-3(S)-amino-3-(4-hydroxyphenyl) Propionic Acid Each of the components described in Step D. was hydrolysed separately to the free acid by adding to each 2 equivalents of KOH in 3/1 ethanol/water. The solutions were acidified with 2.5 N HCl and each component was extracted with methylene chloride. Each component was purified by flash column chromatography using 97/3/0.2 methylene chloride/methanol/acetic acid as the eluant. Thirty seven mg of the higher Rf N-(3,5-dichlorobenzenesulfonyl)-2(S)-prolyl-3(R)-amino-3-(4-hydroxyphenyl)propionic acid was recovered. The tert-butyldimethylsilyl group was removed under anhydrous acid treatment.

400 MHz $^1$H NMR (CD$_3$OD): δ 1.7–1.8 (m, 1H), 1.9–2.0 (bs, 3H), 2.85 (d, 2H, J=16 Hz) 3.1–3.2 (bm, 1H), 3.50 (bm, 1H), 4.2–4.3 (m, 1H), 5.2–5.3 (m, 1H), 6.74 (d, 2H, J=8 Hz), 7.22 (d, 2H, J=8 Hz), 7.7–7.8 (m, 3H), 8.68 (d, 1H, J=8 Hz) MS: m/e 505 (M+1+NH$_3$).

Thirty two mg of the lower Rf N-(3,5-dichlorobenzenesulfonyl)-2(S)-prolyl-3(S)-amino-3-(4-hydroxyphenyl)propionic acid.

400 MHz $^1$H NMR (CD$_3$OD): 1.65–1.75 (m, 2H), 1.77.1.85 (m, 1H), 2.2–2.3 (bs, 1H), 2.86 (m, 2H), 3.1–3.2 (m, 1H), 3.62 (m, 1H), 4.05–4.15 (m, 1H), 5.25–5.35 (m, 1H), 6.70 (d, 2H, J=8 Hz), 7.17 (d, 2H, J=8 Hz), 7.59 (t, 1H, J=2 Hz), 7.69 (d, 1H, J=2 Hz).MS: m/e 505 (M+1+NH$_3$).

EXAMPLE 28

N-(3,5-Dichlorobenzenesulfonyl)-2(S)-prolyl-3(R)-amino-3-(4-tert-butyloxyphenyl)propionic Acid Step A. 4-Benzyloxyphenyldiazoniumtetrafluoroborate.

In a 250 mL round bottomed flask fitted with a stir bar was added 4-benzyloxyaniline (8.7g, 43.6 mmol), 150 mL of ethanol and 17 mL of 48% fluoroboric acid. Cool to 0° C. Then isoamyl nitrite (6,64 mL, 50 mol) was added dopwise over 15 minutes, keeping the solution temperature below 8° C. Stir 2 h at 0–4° C. The product precipitated out of solution. Diluted the reaction mixture with 100 mL ether and filter the reaction mixture. Wash the precipitate with 2×50 mL of ether. Recovered 10.3 g (79%) of product. Melting point=137° (dec), Lit.=140–142 (dec).

Step B. 4-Benzyloxycinnamic Acid, Methyl Ester

The following reaction was adapted from M. Beller and K. Kuhlein, *Synlett*, p 441 (1995). In a 50 mL round bottomed flask fitted with a stir bar and septum was added 4-benzyloxyphenyldiazoniumtetrafluoroborate (3.0 g, 10.2 mmol) and methyl acrylate (1.72 g, 0 mmol) in 15 mL of methanol. Subsequently, 10% palladium on carbon (250 mg, 0.2 mmol) was added to the mixture and it was heated at 55–60° C. until nitrogen gas evolution ceased (2 h) then overnight at 50° C. The reaction was cooled to room temperature, the catalyst filtered off and washed with methanol. The solvent is removed under reduced pressure and the residue purified by flash chromatography (90/10 hexane/ethyl acetate) Recovered 2.0 g of product (70% yield).

400 MHz $^1$H NMR (CDCl$_3$): δ 3.78 (s, 3H), 5.08 (s, 2H), 6.25 (d, 1H, J=17 Hz), 6.29 (d, 1H, J=9 Hz), 7.3–7.4 (m, 5H,), 7.45 (d, 2H, J=9 Hz), 7.62 (d, 1H, J=14 Hz)

Step C. 3-(4-Benzyloxyphenyl)-3(R)-[benzyl-(1 (S)-phenylethyl)-amino]-propionic Acid, Methyl Ester This procedure was adapted from S. G. Davies and O. Ichihara, *Tetrahedron: Asymmetry*, 2, p 183 (1991). In a 100 mL round bottom flask fitted with a stir bar and rubber septum is added (S)-(-)-N-benzyl-1-phenylethylamine (1.69 g, 8.0 mmol) in 60 mL of anhydrous tetrahydrofuran. Cooled to 0° C. and flushed with nitrogen. n-Butyl lithium (2.5N solution in hexane, 3.2 mL) was added dropwise, keeping the temperature below 4° C. for 15 minutes after final base addition. Then cooled to –78° C. and slowly added 4-benzyloxycinnamic acid, methyl ester (1.07g, 4.0 mmol) in 15 ml of dry tetrahydrofuran at such a rate that the solution temperature remaines below –60° C. Stirred for 15 minutes, then quenched with saturated ammonium chloride (5 mL). Warmed to room temperature and added 10 mL of saturated brine. Extracted with 2×25 mL of ether, dried over MgSO$_4$. Filtration and evaporation gave a mixture of the adduct and excess amineas a pale yellow oil. Flash chromatography (90/10 hexane/ethyl acetate) gave the product (1.25 g, 2.62 mmol) (66% yield) which ran just above the excess amine on TLC).

400 MHz $^1$H NMR (CDCl$_3$): δ 1.19 (d, 2H, J=7 Hz), 2.50 (dd, 1H, J=13 Hz, J=10 Hz), 2.64 (dd, 1H J=13 Hz, J=6 Hz), 3.44 (s, 3H), 3.62 (q, 2H, J=15 Hz), 3.97 (q, 1H, J=6 Hz), 4.36 (dd, 1H, J=9 Hz, J=6 Hz), 5.03 (S, 2H), 6.93 (d, 2H, J=9 Hz), 7.2–7.5 (m, 17H).

Step D. 3(R)-Amino-3-(4-hydroxphenyl)propionic acid, Methyl Ester, Acetic Acid Salt To a 250 mL medium pressure Parr hydrogenation bottle was added 25 mL of methanol, 1 mL of glacial acetic acid, 100 mg of 10% palladium hydroxide on carbon and 3-(4-benzyloxyphenyl)-3(R)-[benzyl-(1(S)-phenylethyl)-amino]propionic acid, methyl ester(1.25 g, 2.6 mmol). The flask was evacuated then pressurized to 50 psi H$_2$. and shaken until no more H$_2$ uptake was observed (4 h). Filter the solution through Celite, wash the pad with methanol (50 mL) and concentrate the filtrate under reduced pressure. Recovered 660 mg of product (theoretical) which was used without further purification.

Step E. N-(3,5-Dichlorobenzenesulfonyl)-(L)-proline, Pentafluorophenol Ester

To a 50 mL round bottomed flask fitted with a stir bar and septum was added N-(3,5-dichlorobenzenesulfonyl)-(L)-proline (from Example 22, Step G) (680 mg, 2.10 mmol) and 10 mL of ethyl acetate. Then dicyclohexylcarbodiimide (563 mg, 2.7 mmol) and pentafluorophenol (1.1 g, 6.0 mmol) were added to the flask and the mixture stirred for 2 h. The urea was filtered off and washed with 2×15 mL of ethyl acetate. The residue was used subsequently without purification. TLC (70/30 hexane/ethyl acetate) indicated that no starting material remained.

Step F. N-(3,5-Dichlorobenzenesulfonyl)-2(S)-prolyl-3(R)-amino-3-(4-hydroxyphenyl)propionic Acid,Methyl Ester To a 50 mL round bottomed flask was added crude N-(3,5-dichlorobenzenesulfonyl)-(L)-proline, pentafluorophenol ester in 2/1 dioxane/methylene chloride (30 mL) and 3(R)-amino-3-(4-hydroxyphenyl)propionic acid, methyl ester (500 mg, 2.56 mmol, from Example 28, Step C). The suspension was heated with stirring over 20 min to 55° C., then overnight at 40° C. The reaction mixture was worked up by dissolving the residue in 50 mL of methylene chloride and extracting it with 4×25 mL of saturated sodium bicarbonate,dried over MgSO$_4$, filtered and the sovent removed under reduced pressure. The residue was flash chromatographed (85/15 hexane/ethyl acetate) and N-(3,5-dichlorobenzenesulfonyl)-2(S)-prolyl-3(R)-amino-3-(4-hydroxyphenyl)propionic acid,methyl ester (800 mg, 1.5 mmol) was recovered (76% yield).

400 MHz $^1$H NMR (CDCl$_3$): δ 1.6–1.75 (m, 3H), 2.15–2.25 (bs, 1H), 2.85 (dd, 1H, J=16 Hz, J=6 Hz), 2.95 (dd, 1H, J=16 Hz, J=6 Hz), 3.15–3.25 (m, 1H), 3.63 (m, 1H) 3.66 (s, 3H), 4.10–4.15 (m, 1H), 5.35–5.45 (m, 1H), 6.73 (d, 2H, J=8 Hz), 7.12 (d, 2H, J=8 Hz), 7.61 (t, 1H, J=2 Hz), 7.71 (d, 1H, J=1 Hz), 7.73 (m, 1H).

Step G. N-(3,5-Dichlorobenzenesulfonyl)-2(S)-prolyl-3(R)-amino-3-(4-tert-butyloxyphenyl)propionic Acid, Methyl Ester In a 500 μl spin vane vial fitted with a magnetic stirrer was added N-(3,5-dichlorobenzenesulfonyl)-2(S)-prolyl-3(R)-amino-3-(4-hydroxyphenyl)propionic acid,methyl ester (25 mg, 0.05 mmol), tert-butyloxytrichoroacetimidate (12 mg, 0.055 mmol) and 300 μl of a 2/1 mixture of cyclohexane/methylene chloride. Then a catalytic amount of boron trifluoride etherate (5 μl) was added and the reaction was stirred at 24° C. for 1 h. No starting material was seen by TLC (70/30 hexane/ethyl acetate). The reaction was worked up with 1 mL of saturated sodium bicarb and 2 mL of methylene choride, dried over MgSO$_4$, filtered and the solvent removed under reduced pressure. Flash chromatography (70/30 hexane/ethyl acetate) afforded 25 mg of product (89% yield).

400 MHz $^1$H NMR (CDCl$_3$): δ 1.33 (s, 9H,), 1.7–1.8 (m, 3H), 2.15–2.25 (bs, 1H), 2.87 (dd, 1H, J=16 Hz, J=6 Hz), 2.97 (dd, 1H, J=16 Hz, J=6 Hz), 3.15–3.25 (m, 1H), 3.63 (m, 1H), 3.62 (s, 3H), 4.10–4.15 (m, 1H), 5.35–5.45 (m, 1H), 6.95 (d, 2H, J=8 Hz), 7.18 (d, 2H, J=8 Hz), 7.61 (t, 1H, J=2 Hz), 7.71 (d, 1H, J=1 Hz), 7.73 (m, 1H).

Step H. N-(3,5-Dichlorobenzenesulfonyl)-2(S)-prolyl-3(R) amino-3-(4-tert-butyloxyphenyl)propionic Acid The product described in Step G. was hydrolysed to the free acid by adding 2 equivalents of KOH in 3/1 ethanol/water. The solution was acidified with 2.5 N HCl and extracted with methylene chloride. The product was flash chromatographed using 97/3/0.2 methylene chloride/methanol/acetic acid. Recovered 16mg of product (66% yield).

400 MHz $^1$H NMR (CD$_3$OD): δ 1.31 (s, 9H,), 1.7–1.8 (m, 1H), 1.9–2.0(m, 3H), 2.81 (m, 2H), 3.2–3.3 (m, 2H), 3.5–3.6 (m, 1H), 4.2 (m, 1H), 5.35–5.45 (m, 1H), 6.95 (d, 2H, J=8 Hz), 7.30 (d, 2H, J=8 Hz), 7.7–7.8 (rm, 3H), 8.75 (m, 1H). MS: m/e 560 (M+1+NH$_3$)

EXAMPLE 29

N-(3,5-Dichlorobenzenesulfonyl)-2(S)-prolyl-3(R)-amino-3-(4-(2'-cyanophenyl)-phenyl)propionic Acid Step A. N-(3,5-Dichlorobenzenesulfonyl)-2(S)-prolyl-3(R)-amino-3-(4-trifluoromethylsulfonyloxyphenyl)propionic Acid)propionic Acid, Methyl Ester The title compound was made according to the procedure described in Example 22 and 23, Step C starting with N-(3,5-dichlorobenzenesulfonyl)-2(S)-prolyl-3(R)-amino-3-(4-hydroxyphenyl)propionic acid,methyl ester (500 mg, 1.0 mmol) (from Example 29, Step F) to provide 400 mg (67% yield) of desired product.

400 MHz $^1$H NMR (CDCl$_3$): δ 1.6–1.8 (m, 3H), 2.15–2.25 (bs, 1H), 2.2 (dd, 1H, J=16 Hz, J=6 Hz), 2.94 (dd, 1H, J=16 Hz, J=6 Hz), 3.15–3.25 (m, 1H), 3.63 (m, 1H), 3.67 (s, 3H), 4.10–4.15 (m, 1H), 5.4–5.5 (m, 1H), 6.95 (d, 2H, J=8 Hz), 7.26 (d, 2H, J=3 Hz), 7.40 (d, 2H, J=9 Hz), 7.61 (t, 1H, J=2 Hz), 7.71 (d, 2H, J=1 Hz), 7.91 (m, 1H).

Step B. N-(3,5-Dichlorobenzenesulfonyl)-2(S)-prolyl-3(R)-amino-3-(4-(2'-cyanophenyl)phenyl)propionic Acid, Methyl Ester The title compound was made according to the procedure described in Example 22 and 23, Step D starting with N-(3,5-dichlorobenzenesulfonyl)-2(S)-prolyl-3(R)-amino-3-(4-trifluoromethylsulfonyloxyphenyl)propionic acid, methyl ester (40 mg, 0.067mmol) and 2-cyanobenzene boronic acid (15 mg, 0.10 mmol) to provide 15 mg (38% yield) of desired product.

400 MHz $^1$H NMR (CDCl$_3$): δ 1.7–1.9 (m, 3H), 2.2–2.3 (bs, 1H), 2.92 (dd, 1H, J=16 Hz, J=6 Hz), 3.02 (dd, 1H, J=16 Hz, J=6 Hz), 3.15–3.25 (m, 1H), 3.65 (m, 1H), 3.69 (s, 3H), 4.05–4.15 (m, 2H), 5.4–5.5 (m, 1H), 6.9–7.0 (m, 2H), 7.4–7.6 (m, 6H), 7.60 (t, 2H, J=2 Hz), 7.72 (d, 2H, J=1 Hz), 7.75 (m, 1H), 7.90 (m, 1H

Step C. N-(3,5-Dichlorobenzenesulfonyl)-2(S)-prolyl-3(R)-amino-3-(4-(2'-cyanophenyl)phenyl)propionic Acid The product described in Step B was hydrolysed to the free acid by adding 2 equivalents of KOH in 3/1 ethanol/water. The solution was acidified with 2.5 N HCl and extracted with methylene chloride. The product was flash chromatographed using 97/3/0.2 methylene chloride/methanol/acetic acid to provide 7 mg of product (50% yield).

400 MHz $^1$H NMR (CD$_3$OD): δ 1.7–1.8 (m, 1H), 1.9–2.05 (m, 3H), 2.8–2.95 (m, 2H), 3.3–3.4 (m, 2H), 3.5–3.6 (m, 1H), 4.25 (m, 1H), 5.4–5.5 (m, 1H), 7.5–7.6 (m, 6H), 7.7–7.8 (m, 5H), 8.80 (m, 1H), MS: m/e 590 (M+1+NH$_3$).

EXAMPLE 30

N-(3,5-Dichlorobenzenesulfonyl)-2(S)-prolyl-3(R)-amino-3-(4-(2'-formyl)biphenyl)-propionic Acid The procedure described in Example 22 and 23, Step D starting with N-(3,5-dichlorobenzenesulfonyl)-2(S)-prolyl-3(R)-amino-3-(4-trifluoromethane-sulfonyloxyphenyl) propionic acid, methyl ester 100 mg, 0.167mmol) and 2-formylbenzene boronic acid (130 mg, 0.20 mmol) was followed to provide 45 mg (47% yield) of the methyl ester of the title compound. The methyl ester was hydrolysed to the free acid by adding 2 equivalents of KOH in 3/1 ethanol/water. The solution was acidified with 2.5 N HCl and extracted with methylene chloride. The product was flash chromatographed using 97/3/0.2 methylene chloride/methanol/acetic acid to provide 7 mg of the title compound (50% yield).

400 MHz $^1$H NMR (CDCl$_3$): δ 1.7–1.9 (m, 3H), 2.2–2.3 (bs, 1H), 3.02 (dd, 1H, J=16 Hz, J=6 Hz), 3.10 (dd, 1H, J=16 Hz, J=6 Hz), 3.15–3.25 (m, 1H), 3.65 (m, 1H), 4.1–4.2 (m, 2H), 5.4–5.5 (m, 1H), 7.3–7.5 (m, 5H), 7.6–7.7 (m, 2H), 7.71 (d, 2H, J=2 Hz), 7.99 (dd, 2H, J=14 Hz, J=8 Hz), 9.85 (m, 1H). MS: m/e 593 (M+1+NH$_3$).

EXAMPLE 31

N-(3,5-Dichlorobenzenesulfonyl)-2(S)-prolyl-3(R)-amino-3-(4-(2'-dimethylamino-methyl)biphenyl) propionic Acid.

N-(3,5-Dichlorobenzenesulfonyl)-2(S)-prolyl-3(R)-amino-3-(4-(2'-formyl)biphenyl)propionic acid, methyl ester (from Example 30 (28 mg, 0.047 mmol) was dissolved in methanol (1 mL). Dimethylamine (118 μl, 0.24 mmol of 2M dimethylamine in methanol) was added to the solution along with sodium cyanoborohydride (4.4 mg, 0.07 mmol). The reaction mixture was stirred overnight at 24° C. No starting aldehyde was seen by TLC. Aqueous workup effected an in situ hydrolysis of the methyl ester. The reaction mixture was acidified with 2.5 N HCl and extracted with methylene chloride. The product was flash chromatographed using 97/3/0.2 methylene chloride/methanol/acetic acid to provide 3.3 mg of the title compound (15% yield).

400 MHz $^1$H NMR (CDCl$_3$): δ 1.7–1.9 (m, 3H), 2.2–2.3 (bs, 1H), 2.45 (bs, 6H) 2.92 (dd, 1H, J=16 Hz, J=6 Hz), 3.08 (dd, 1H, J=16 Hz, J=6 Hz), 3.15–3.25 (m, 3.65 (m, 1H), 4.16 (d, 1H, J=6 Hz), 4.2–4.3 (m, 2H), 5.4–5.5 (m, 1H), 7.20 (d, 2H, J=6 Hz), 7.30 (m, 1H), 7.42 (d, 2H, J=8 Hz), 7.48 (d, 2H, J=8 Hz), 7.59 (t, 1H, J=2 Hz), 7.71 (d, 2H, J=2 Hz), 7.77 (m, 1H), 8.10 (m, 1H). MS: m/e 608 (M+1+NH$_3$).

EXAMPLE 32

N-(3,5-Dichlorobenzenesulfonyl)-2(S)-prolyl-3(R) amino-3-(4-(2'-hydroxymethyl)-biphenyl)propionic Acid N-(3,5-Dichlorobenzenesulfonyl)-2(S)-prolyl-3(R)-amino-3-(4-(2'-formyl)biphenyl)propionic acid, methyl ester (from Example 30 (16 mg, 0.027 mmol)) was dissolved in ethanol (500 μl). Sodium borohydride (2 mg, 0.054 mmol) was added to the reaction mixture and the solution stirred at 24° C. for 1 h. No starting aldehyde was seen by TLC (97/3/0.2 methylene chloride/methanol/acetic acid). The reaction mixture was acidified with 2.5 N HCl and extracted with methylene chloride. The product was flash chromatographed using 97/3/0.2 methylene chloride/methanol/acetic acid to provide 11.5 mg of the title compound (73% yield).

400 MHz $^1$H NMR (CDCl$_3$): δ 1.7–1.9 (m, 3H), 2.15–2.25 (bs, 1H), 2.45 (bs, 6H), 2.94 (dd, 1H, J=16 Hz, J=6 Hz), 3.04 (dd, 1H, J=16 Hz, J=6 Hz), 3.1–3.2 (m, 1H), 3.5–3.6 (m, 1H), 3.5–4.3 (vbs, 1H), 4.14 (d, 1H, J=6 Hz), 4.55 (s, 2H), 5.4–5.5 (m, 1H), 7.1–7.2 (m, 2H), 7.2–7.3 (m, 2H), 7.3–7.4 (m 3H), 7.52 (d, 2H, J=8 Hz), 7.59 (t, 1H), J=2 Hz), 7.71 (d, 2H, J=2 Hz), 7.82 (m, 1H). MS: m/e 595 (M+1+NH$_3$).

The following compounds were prepared by the procedures described in Example 22 and 23 using the appropriate aryl-halide

| Ex. No | Compound Name | MS* |
|---|---|---|
| (33) | N-(3,5-dichlorobenzenesulfonyl)-2(S)-prolyl-3(R)-amino-3-(4-(2-methyl-5-trifluoromethylbenzoxazol-7-yl)-phenyl)-propionic acid | 698 (M + NH$_4$) |
| (34) | N-(3,5-dichlorobenzenesulfonyl)-2(S)-prolyl-3(R)-amino-3-(4-(pyrimidin-5-yl)phenyl)-propionic acid | 567 (M + NH$_4$) |
| (35) | N-(benzenesulfonyl)-2(S)-prolyl-3(R)-amino-3-(4-(2'-methoxyphenyl)phenyl)-propionic acid | 525 (M + NH$_4$) |
| (36) | N-(3-pyridylsulfonyl)-2(S)-prolyl-3(R)-amino-3-(4-(2'-methoxyphenyl)phenyl)-propionic acid | |
| (37) | N-(benzenesulfonyl)-2(S)-methylprolyl-3(R)-amino-3-(4-(2'-methoxyphenyl)phenyl)-propionic acid | 539 (M + NH$_4$) |
| (38) | N-(3-pyridylsulfonyl)-2(S)-methylprolyl-3(R)-amino-3-(4-(2'-methoxyphenyl)phenyl-propionic acid | 526 (M + NH$_4$) |

*m/e: (M + 1 (H$^+$))$^+$ or (M + 18 (NH$_4$$^+$))$^+$

EXAMPLE 39

N-(3,5-Dichlorobenzenesulfonyl)-2-methyl-2(S)-prolyl-3(R)-amino-3-(4-(2'-methoxyphenyl)phenyl) propionic Acid Step A. N-tert-Butoxycarbonyl-3(R)-amino-3-(4-hydroxyphenyl)propionic Acid, Methyl Ester.

To a 100 mL round bottom flask fitted with a magnetic stir bar was added 15 mL of water and 30 mL of dioxane. The flask was cooled to 0° and then 3(R)-amino-3-(4-hydroxphenyl)propionic acid, methyl ester, acetic acid salt (3.8 g, 15 mmol), [from Example 28, Step D] diisopropylethyl amine (DIPEA) (3.5 mL, 30 mmol) and BOC-ON (4.24 g, 17.3 mmole) were added sequentially to the flask. The reaction mixture was stirred for 3 h at 0–5°. The reaction was poured into 100 mL of cold 0.25 N HCl and the mixture was extracted with 5 times 50 mL of ether. Flash chromatography (90/10 hexane/ethyl acetate) removed the forerun by-product and subsequent 70/30 hexane/ethyl acetate eluted the Boc protected amino acid (4.45 g, 80% yield.

400 MHz $^1$H NMR (CDCl$_3$): δ 1.42 (s, 9H), 2.7–2.9 (m, 2H), 3.6 (s, 3H), 5.0 (bs, 1H), 5.4 (bs, 1 H), 5.6 (bs, 1 H), 6.7 (d, 2H, J=9 Hz), 7.17 (d, 2H, J=9 Hz).

Step B. N-tert-Butoxycarbonyl-3(R)-amino-3-(4-trifluoromethylsulfonyl-oxyphenyl)propionic Acid, Methyl Ester.

The procedure described in Examples 22, Step C was followed using 3.50 g of N-tert-butoxycarbonyl-3(R)-amino-3-(4-hydroxyphenyl)propionic acid, methyl ester to provide 4.8 g of desired triflate (90% yield).

400 MHz $^1$H NMR (CDCl$_3$): δ 1.40 (s, 9H), 2.85 (bs, 2H), 3.60 (s, 3H), 5.1 (bs, 1H), 5.60 (bs, 1H), 7.21 (d, 2H, J=8 Hz), 7.36 (d, 2H, J=8 Hz).

Step C. N-tert-Butoxycarbonyl-3(R)-amino-3-(4-(2'-methoxyphenyl)-phenyl)propionic Acid, Methyl Ester.

Coupling of 2-methoxybenzeneboronic acid (91 mg, 0.6 mmol) with N-tert-butoxycarbonyl-3(R)-amino-3-(4-trifluoromethylsulfonyloxyphenyl)propionic acid, methyl ester (214 mg, 0.5 mmol) as described in Example 22 and 23, Step D gave 170 mg of the desired product (quantitative yield).

400 MHz $^1$H NMR (CDCl$_3$): δ 1.41 (s, 9H), 2.8–2.9 (bs, 2H), 3.63 (s, 3H), 3.79 (s, 3H), 5.1 (bs, 1H), 5.40 (bs, 1H), 6.9–7.02 (m, 2H), 7.2–7.4 (m, 4H), 7.30 (d, 2H, J/32 7 Hz), 7.48 (d, 2H, J=7 Hz).

Step D. 3(R)-Amino-3-(4-(2'-methoxyphenyl)phenyl) propionic Acid, Methyl Ester Hydrochloride.

The title compound was synthesized by the procedure described in Example 22 and 23, Step F by deprotecting the Boc protected amino acid of Step C with anhydrous HCl in ethyl acetate to provide 120 mg of the HCl salt from 170 mg of starting material.

Step E. N-(3,5-Dichlorobenzenesulfonyl)-2-methyl-2(S)-prolyl-3(R)-amino-3-(4-(2'-methoxyphenyl)phenyl) propionic Acid, Methyl Ester.

To a 5 mL round bottom flask fitted with a stir bar and septum was added 3(R)-amino-3-(4-(2'-methoxyphenyl) phenyl)propionic acid, methyl ester hydrochloride (32 mg, 0.1 mmol), diisopropylethyl amine (DIPEA) (72 μl, 0.4 mmol), benzotriazol-1-yloxytripyrrolidino phosphonium hexafluorophosphate (PyBOP) (64 mg, 0.12 mmol) and N-(3,5-dichlorobenzenesulfonyl)-2-methyl-2(S)-proline (36 mg, 0.11 mmol) in 1 ml of methylene chloride. The mixture was stirred overnight at 24° C. and worked up by adding 0.5 N HCl (pH=3) and extracting out the product with methylene chloride. The solvent was removed and the residue flash chromatographed (70/30 hexane/ethyl acetate to give the desired product.

400 MHz $^1$H NMR (CDCl$_3$): δ 1.7 (s, 3H), 1.8–1.9 (bs, 1h), 1.92–2.0 (bs, 1H), 2.45–2.55 (bs, 1H), 3.0–3.1 (m, 2H), 3.4–3.5 (m, 1H), 3.73 (s, 3H), 3.78–3.83 (m, 1H), 3.88 (s, 3H), 5.45–5.53 (m, 1H), 7.10–7.2 (m, 2H), 7.3–7.5 (m, 3H), 7.65–7.73 (m, 3H), 7.67 (d, 1H, J=2Hz), 7.70 (d, 2H, J=2 Hz).

Step F. N-(3,5-Dichlorobenzenesulfonyl)-2-methyl-2(S)-prolyl-3(R)-amino-3-(4-(2'-methoxyphenyl)phenyl) propionic acid The ester in Step E was hydrolysed to the free acid by adding to 2 equivalents of NaOH in 3/1 ethanol/water at room temperature. When the hydrolysis was complete, the solvent was removed under reduced pressure and the residuce was acidified with 2.5 N HCl. The product was extracted with methylene chloride and chromatographed with (98/1.8/0.2) CH$_2$ Cl$_2$/MeOH/AcOH) to provide 40 mg of the title compound.

400 MHz $^1$H NMR (CDCl$_3$): δ 1.7 (s, 3H), 1.8–1.9 (bs, 1H), 1.92–2.0 (bs, 1H), 2.45–2.55 (bs, 1H), 3.0–3.1 (m, 2H), 3.4–3.5 (m, 1H), 3.78–3.83 (m, 1H), 3.88 (s, 3H), 5.45–5.53 (m, 1H), 7.10–7.2 (m, 2H), 7.3–7.5 (m, 3H), 7.65–7.73 (m, 3H), 7.65–773 (m, 3H), 7.67 (d, 1H, J=2Hz), 7.70 (d, 2H, J=2 Hz). MS: m/e 608 (M+NH$_4$).

The following compounds were prepared by the procedures described in Example 39 by coupling the appropriate aryl boronic acid to N-tert-butoxycarbonyl-3(R)-amino-3-(4-trifluoromethylsulfonyloxyphenyl)propionic acid, methyl ester Example 39, Step B. The aryl boronic acids were synthesized as taught by Galada et al, *Synthesis-Stuttgart* (5), 614-(1996), from the corresponding aryl bromide or iodide by transmetallation with t-butyllithium in THF at −78°, followed by treatment with a trialkoxyboronate then subsequent hydrolysis with 2.5 N aqueous HCl. After Boc-deprotection (Example 39, Step D), the resultant β-aminoacid hydrochloride was coupled to either N-(3,5-dichlorobenzenesulfonyl))-2-methyl-2(S)-proline or N-(3,5-dichlorobenzenesulfonyl)-2(S)-proline by the method taught in Example 39, Step E.

For the compound of Example 56, the starting material N-(3-chlorobenzenesulfonyl)-2-methyl-2(S)-proline was synthesized by the procedure taught in Example 22, Step G using 3-chlorobenzenesulfonyl chloride instead of 3,5-dichlorobenzenesulfonyl chloride.

For the compound of Example 59, the starting material N-(3,5-dichlorobenzenesulfonyl)-2(S)-pipecolic acid was synthesized by the procedure of Example 22, Step G using (S)-pipecolic acid, methyl ester (Bachem) instead of 2(S)-methyl-proline, followed by ester hydrolysis.

For the compounds of Examples 57 and 58, 3(R)-amino-3-(4-methoxyphenyl)propionic acid was synthesized by alkylating N-tert-butoxycarbonyl-3(R)-amino-3-(4-hydroxyphenyl)propionic acid, methyl ester (Example 39, Step A) with methyl iodide/potassium carbonate in acetone followed by ester hydrolysis.

| Ex. No | Compound Name | MS* |
|---|---|---|
| (40) | N-(benzenesulfonyl)-2-methyl-2(S)-prolyl-3(R)-amino(4-(4'-fluorophenyl)phenyl)-propionic acid | 527 (M + NH$_4$) |
| (41) | N-(3,5-dichlorobenzenesulfonyl)-2(S)-prolyl-3(R)-amino(4-(4'-fluorophenyl)phenyl)-propionic acid | 582 (M + NH$_4$) |

-continued

| Ex. No | Compound Name | MS* |
|---|---|---|
| (42) | N-(3,5-dichlorobenzenesulfonyl)-2(S)-prolyl-3(R)-amino(4-(2'-trifluoromethoxyphenyl)phenyl)propionic acid | 631 (M + 1) |
| (43) | N-(3,5-dichlorobenzenesulfonyl)-2-methyl-2(S)-prolyl-3 (R)-amino(4-(2'-trifluoromethoxyphenyl)-phenyl)propionic acid | 645 (M + 1) |
| (44) | N-(3,5-dichlorobenzenesulfonyl)-2-methyl-2(S)-prolyl-3(R)-amino-3-(4-(3'-methoxyphenyl)phenyl)propionic acid | 608 (M + NH$_4$) |
| (45) | N-(3,5-dichlorobenzenesulfonyl)-2(S)-prolyl-3(R)-amino-3-(4-(3'-methoxyphenyl)phenyl)propionic acid | 594 (M + NH$_4$) |
| (46) | N-(3,5-dichlorobenzenesulfonyl)-2-methyl-2(S)-prolyl-3(R)-amino-3-(4-(2'-methoxy-3'-fluoro-phenyl)phenyl)propionic acid | 626 (M + NH$_4$) |
| (47) | N-(3,5-dichlorobenzenesulfonyl)-2(S)-prolyl-3(R)-amino-3-(4-(2'-methoxy-3'-fluorophenyl)phenyl)propionic acid | 612 (M + NH$_4$) |
| (48) | N-(3,5-dichlorobenzenesulfonyl)-2-methyl-2(S)-prolyl-3(R)-amino-3-(4-(2'-fluoro-3'-methoxyphenyl)-phenyl)propionic acid | 626 (M + NH$_4$) |
| (49) | N-(3,5-dichlorobenzenesulfonyl)-2(S)-prolyl-3(R)-amino-3-(4-(2'-fluoro-3'-methoxyphenyl)phenyl)propionic acid | 612 (M + NH$_4$) |
| (50) | N-(3,5-dichlorobenzenesulfonyl)-2-methyl-2(S)-prolyl-3(R)-amino-3-(4-(2'-methoxy-5'-fluorophenyl)-phenyl)propionic acid | 626 (M + NH$_4$) |
| (51) | N-(3,5-dichlorobenzenesulfonyl)-2(S)-prolyl-3(R)-amino-3-(4-(2'-methoxy-5'-fluorophenyl)phenyl)propionic acid | 612 (M + NH$_4$) |
| (52) | N-(3,5-dichlorobenzenesulfonyl)-2-methyl-2(S)-prolyl-3(R)-amino-3-(4-(3'-methoxy-5'-fluorophenyl)-phenyl)propionic acid | 626 (M + NH$_4$) |
| (53) | N-(3,5-dichlorobenzenesulfonyl)-2(S)-prolyl-3(R)-amino-3-(4-(3'-methoxy-5'-fluorophenyl)phenyl)propionic acid | 612 (M + NH$_4$) |
| (54) | N-(3,5-dichlorobenzenesulfonyl)-2-methyl-2(S)-prolyl-3(R)-amino-3-(4-(2'-methoxy-6'-fluoro-phenyl)phenyl)propionic acid | 626 (M + NH$_4$) |
| (55) | N-(3,5-dichlorobenzenesulfonyl)-2(S)-prolyl-3(R)-amino-3-(4-(2'-methoxy-6'-fluorophenyl)phenyl)propionic acid | 612 (M + NH$_4$) |
| (56) | N-(3-chlorobenzenesulfonyl)-2-methyl-2-(S)-prolyl-3(R)-amino-3-(4-(2'methoxyphenyl)phenyl)propionic acid | 574 (M + NH$_4$) |
| (57) | N-(3,5-dichlorobenzenesulfonyl)-2-methyl-2(S)-prolyl-3(R)-amino-3-(4-methoxyphenyl)propionic acid | 532 (M + NH$_4$) |
| (58) | N-(3,5-dichlorobenzenesulfonyl)-2(S)-prolyl-3(R)-amino-3-(4-methoxyphenyl)propionic acid | 518 (M + NH$_4$) |
| (59) | N-(3,5-dichlorobenzenesulfonyl)-2(S)-pipecolinyl)-3(R)-amino-3-(4-(2'-methoxy-phenyl)phenyl)propionic acid | 608 (M + NH$_4$) |

*m/e: (M + 1 (H$^+$))$^+$ or (M + 18 (NH$_4^+$))$^+$

The following compounds were synthesized by reacting either N-(3,5-dichlorobenzenesulfonyl)-2(S)-prolyl-3(R)-amino-3-(4-hydroxyphenyl)propionic 5 acid,methyl ester or N-(3,5-dichlorobenzenesulfonyl)-2-methyl-2(S)-prolyl-3 (R)-amino-3-(4-hydroxyphenyl)propionic acid,methyl ester (as prepared in Example 28, Step F) with triflic anhydride according to the procedure described in Example 22 and 23, Step C to form N-(3,5-dichlorobenzenesulfonyl)-2(S)-prolyl-3(R)-amino-3-(4-trifluoromethylsulfonyloxyphenyl) propionic acid, methyl ester or N-(3,5-dichloro-benzenesulfonyl)-2-methyl-2(S)-prolyl-3(R)-amino-3-(4-trifluoromethyl-sulfonyloxyphenyl)propionic acid, methyl ester; the triflic derivatives were coupled with the appropriate arylboronic acid according to the procedure in Examples 22 and 23, Step D, and the resultant products subsequently hydrolyzed to the free carboxylic acid as described in Example 39, Step F.

| Ex No | Name | MS* |
|---|---|---|
| (60) | N-(3,5-dichlorobenzenesulfonyl)-2-methyl-2(S)-prolyl-3(R)-amino-3-(4-(2'-trifluoromethoxy-4'-fluorophenyl)-phenyl)propionic acid | 663 (M + 1) |
| (61) | N-(3,5-dichlorobenzenesulfonyl)-2(S)-prolyl-3(R)-amino-3-(4-(2'-trifluoromethoxy-4'-fluorophenyl)phenyl)-propionic acid | 649 (M + 1) |
| (62) | N-(3,5-dichlorobenzenesulfonyl)-2(S)-prolyl-3(R)-amino-3-(4-(2'-methoxy-4'-fluorophenyl)phenyl)propionic acid | 612 (M + NH$_4$) |
| (63) | N-(3,5-dichlorobenzenesulfonyl)-2-methyl-2(S)-prolyl-3(R)-amino-3-(4-(2'-methoxy-4'-fluorophenyl)phenyl)-propionic acid | 626 (M + NH$_4$) |

-continued

| Ex No | Name | MS* |
|---|---|---|
| (64) | N-(3,5-dichlorobenzenesulfonyl)-2-methyl-2(S)-prolyl-3(R)-amino-3-(4-hydroxyphenyl)propionic acid | 518 (M + NH$_4$) |
| (65) | N-(3,5-dichlorobenzenesulfonyl)-2-methyl-2(S)-prolyl-3(R)-amino-3-(4-(3'-pyridyl)phenyl)propionic acid | 565 (M + 1) |

*m/e: (M + 1 (H$^+$))$^+$ or (M + 18 (NH$_4^+$))$^+$

EXAMPLE 66

N-(3,5-Dichlorobenzenesulfonyl)-2(S)-prolyl-3(R)-amino-3-(4-(N-pyrrolidinyl-carbonyloxy)phenyl) propionic Acid N-(3,5-Dichlorobenzenesulfonyl)-2-methyl-2(S)-prolyl-3(R)-amino-3-(4-hydroxyphenyl)propionic acid methyl ester, as prepared in Example 28, Step F (50 mg, 0.11 mmol), was dissolved in 1 mL of methylene chloride and treated sequentially at 0° with DIPEA (56 μl, 0.3 mmol) and chlorocarbonyl-N-pyrrolidine (16 mg, 0.12 mmol). The mixture was stirred for 1 hour, then worked up with saturated sodium bicarbonate, extracted with methylene chloride and dried over magnesium sulphate. The solution was filtered, solvent removed in vacuo and the product chromatographed on flash silica gel (70/30 hexane/ethyl acetate) (R$_f$=0.3). The methyl ester was recovered (42 mg) and subsequently hydrolysed by the procedure described in Example 39, Step F to N-(3,5-dichlorobenzenesulfonyl)-2(S)-prolyl-3(R)-amino-3-(4-(N-pyrrolidinylcarbonyloxy)phenyl)propionic acid (35 mg).

MS: m/e 501 (M+NH$_4$).

EXAMPLE 67

N-(3,5-Dichlorobenzenesulfonyl)-2(S)-prolyl-3(R)-amino-3-(3-(N-pyrrolidinylcarbonyloxy)phenyl) propionic Acid The title compound was prepared by the acylation method described above in Example 66 substituting 3(R)-amino-3-(3-hydroxyphenyl)propionic acid, methyl ester, which was prepared by the procedure shown in Example 28, Steps B–F, except that (3'-benzyloxy)cinnamic acid, methyl ester (Aldrich) was substituted for (4'-benzyloxy)cinnamic acid, methyl ester.

MS: m/e 501 (M+NH$_4$).

EXAMPLE 68

N-(3,5-Dichlorobenzenesulfonyl)-2(S)-prolyl-3(R)-amino-3-(4-(methoxyethyloxy)phenyl)propionic Acid The title compound was obtained from N-(3,5-dichlorobenzene-sulfonyl)-2(S)-prolyl-3(R)-amino-3-(4-hydroxyphenyl)propionic acid methyl ester, as prepared in Example 28, Step F, by alkylating with 1-bromo-2-methoxyethane and potassium carbonate in acetone, followed by ester hydrolysis.

MS: m/e 562 (M+NH$_4$).

EXAMPLE 69

N-(3,5-Dichlorobenzenesulfonyl)-2-methyl-2(S)-prolyl-3(R)-amino-3-(4-(methoxyethyloxy)phenyl) propionic Acid The title compound was obtained from N-(3,5-dichlorobenzenesulfonyl)-2-methyl-2(S)-prolyl-3(R)-amino-3-(4-hydroxyphenyl)propionic acid methyl ester, as prepared in Example 39 by alkylating with 1-bromo-2-methoxyethane and potassium carbonate in acetone, followed by ester hydrolysis.

MS: m/e 576 (M+NH$_4$).

EXAMPLE 70

N-(3,5-Dichlorobenzenesulfonyl)-2(S)-prolyl-3(R)-amino-3-(4-(2'-cyanophenyloxy)phenyl)propionic Acid N-(3,5-Dichlorobenzenesulfonyl)-2-methyl-2(S)-prolyl-3(R)-amino-3-(4-hydroxyphenyl)propionic acid methyl ester (51 mg. 0.1 mmol), as prepared in Example 28, Step F, was reacted with 2-fluorobenzonitrile (15 mg, 0.12 mmol) in acetonitrile using potassium fluoride on alumina as the solid state catalyst as described by J. Scott Sawer et al *J. Org. Chem.* (58) p3229 (1993), to provide 31 mg of the methyl ester of the title compound, which was purified by flash chromatography (80/20 methylene chloride/ethyl acetate). The title compound was obtained by ester hydrolysis and isolation of the free acid (7 mg) as described in Example 39, Step F.

MS: m/e 619 (M+NH$_4$).

EXAMPLE 71

N-(3,5-Dichlorobenzenesulfonyl)-2(S)-prolyl-3(R)-amino-3-(3-(2'-methoxyphenyl)phenyl)propionic Acid The title compound was prepared by the methods described in Example 24 and 25 except 3(R)-amino-3-(3-hydroxyphenyl)propionic acid, methyl ester was substituted for the 4-hydroxyphenyl derivative.

MS: m/e 594 (M+NH$_4$).

The following compounds containing β-heteroaryl and fused β-heteroaryl β-aminoacids were obtained by the procedures taught in the PCT International Application Publication Nos. WO97/327100 and WO95/17397 and in Example 39.

| Ex No | Name | MS* |
|---|---|---|
| (72) | N-(3,5-dichlorobenzenesulfonyl)-2-methyl-2(S)-prolyl-3(R)-amino-3-(4-pyridyl)propionic acid | 504 (M + 1) |
| (73) | N-(3,5-dichlorobenzenesulfonyl)-2-methyl-2(S)-prolyl-3(S)-amino-3-(4-pyridyl)propionic acid | 504 (M + 1) |
| (74) | N-(3,5-dichlorobenzenesulfonyl)-2-methyl-2(S)-prolyl-3(R)-amino-3-(3-quinolyl)propionic acid | 553 (M + 1) |

*m/e: (M + 1 (H$^+$))$^+$ or (M + 18 (NH$_4^+$))$^+$

EXAMPLE 75

N-(3,5-Dichlorobenzenesulfonyl)-2(S)-prolyl-3(R)-amino-3-(4-(2'-pyridinyl)phenyl)propionic Acid The title compound was prepared according to the procedure described in Example 28 using as starting material 3-amino-3-(4-(2'-pyridyl)phenyl)propionic acid, which was synthesized by procedures as taught by J. G. Rico et al., *J. Org. Chem.*, (1993) 58, 7948.

MS: m/e 579 (M+1).

The following compounds were prepared by peracid oxidation of N-(3,5-dichlorobenzenesulfonyl)-2-methyl-2(S)-prolyl-3(R)-amino-3-(4-(3'-pyridyl)phenyl)propionic acid (Example 65) and the des-methyl analog N-(3,5-dichlorobenzenesulfonyl)-2(S)-prolyl-3(R)-amino-3-(4-(3'-pyridyl)phenyl)propionic acid (which had been prepared by the procedures described in Example 39); followed by thermally induced rearrangement of the N-oxide as taught by M. P. Cava et al *J. Org. Chem.* (23), p1616 (1958).

| Ex No | Name | MS* |
|---|---|---|
| (76) | N-(3,5-dichlorobenzenesulfonyl)-2-methyl-2(S)-prolyl-3(R)-amino-3-(4-(3'-pyridyl-2'-one)phenyl)propionic acid | 595 (M + NH$_4$) |
| (77) | N-(3,5-dichlorobenzenesulfonyl)-2(S)-prolyl-3(R)-amino-3-(4-(3'-pyridyl-2'-one)phenyl)propionic acid | 581 (M + NH$_4$) |

*m/e: (M + 1 (H$^+$))$^+$ or (M + 18 (NH$_4^+$))$^+$

EXAMPLE 78

N-(3,5-dichlorobenzenesulfonyl)-2-methyl-2(S)-prolyl-3(R)-amino-3-(4-(2'-methoxy-3'-pyridyl)phenyl)propionic Acid The pyridone from Example 76 was converted to the methoxy ether using silver oxide and iodomethane as taught by Bouammali, B. et al. *Arch Pharm.* 326 (1993) 9, 547–550.

MS: m/e592(M+1).

EXAMPLE 79

N-(2(R,S)-(4-(Benzyloxycarbonyl)-1-(t-butyloxycarbonyl))piperazoyl)-3(R)-amino-3-(4-(2'-methoxyphenyl)phenyl)propionic Acid Step A. 4-(Benzyloxycarbonyl)-1-(t-butyloxycarbonyl)piperazine-2(R,S)-carboxylic Acid.

This compound was prepared by the method of Dale J. Kempf et al. U.S. Pat. No. 5,455,351. Starting with (R,S)-piperazic acid (5.0 g, 25 mmol), 4-(benzyloxycarbonyl)-1-(t-butyloxycarbonyl)piperazine-2(R,S)-carboxylic acid was obtained (2.9 g, 35% yield).

400 MHz $^1$H NMR (CDCl$_3$): δ 1.4–1.5 (m, 9H), 2.85–3.0 (bm, 1H), 3.1–3.3 (bm, 2H), 3.8–4.0 (bm, 1H), 4.0–4.15 (m, 1H), 4.6–4.7 (m, 1H), 5.05–5.2 (b-dd, 2H), 7.25–7.35 (m, 5H).

Step B. N-(2(R,S)-(4-(Benzyloxycarbonyl)-1-(t-butyloxycarbonyl))piperazoyl)-3(R)-amino-3-(4-(2'-methoxyphenyl)phenyl)propionic Acid.

This compound was made by the procedures taught in Example 39, Step E and Step F by coupling 4-(benzyloxycarbonyl)-1-(t-butyloxycarbonyl)piperazine-2(R,S)-carboxylic acid (111 mg, 0.33 mmol) with 3(R)-amino-3-(4-(2'-methoxyphenyl)phenyl)propionic acid, methyl ester hydrochloride (96 mg, 0.30 mmol). Ester hydrolysis and product isolation proceeded as described in Example 39, Step F to provide 6 mg (0.01 mmol) of the title compound.

400 MHz $^1$H NMR (CDCl$_3$): δ 1.42 (s), 1.45 (s), 1.5–1.7 (m), 2.8–3.3 (m), 3.5–4.2 (m), 4.5–4.75 (m), 5.0–5.2 (m), 7.25–7.35 (m), 7.4–7.5 (m), 7.77 (d, J=2 Hz). MS: m/e 635: (M+8 (NH$_4^+$))$^+$.

EXAMPLE 80 and 81

N-(2(R)-(4-(3,5-Dichlorobenzenesulfonyl))piperazoyl)-3(R)-amino-3-(4-(2'-methoxyphenyl)phenyl)propionic Acid and N-2(S)-(4-(3,5-Dichlorobenzenesulfonyl))piperazoyl)-3(R)-amino-3-(4-(2'-methoxyphenyl)phenyl)propionic Acid Step A. N-(2(R,S)-piperazoyl)-3(R)-amino-3-(4-(2'-methoxyphenyl)phenyl)-propionic Acid.

The title compound was prepared by sequential deprotection of 2(R,S)-4-(benzyloxycarbonyl)-1-(t-butyloxycarbonyl)piperazoyl-3(R)-amino-3-(4-(2'-methoxyphenyl)phenyl)propionic acid, methyl ester (intermediate in Example 79, Step B) by hydrogenolysis of the Cbz group in methanol with 10% palladium on carbon, followed by removal of the Boc group wtih trifluoroacetic acid in methylene chloride. Hydrolysis of the resulting methyl ester as described in Example 39, Step F, gave the title compound.

400 MHz $^1$H NMR (CD$_3$OD): δ 2.85–3.20 (m, 7H), 3.76 (s, 3H), 5.40 (m), 6.95–7.0 (t, 1H, J=8 Hz), 7.04 (d, 1H, J=8 Hz), 7.2–7.24 (d, 1H, J=8 Hz), 7.31 (t, 1H, J=8 Hz), 7.38 (m, 2H), 7.4–7.5 (m, 2H). MS: m/e 399 (M+NH$_4$ $^+$).

Step B. N-(2(R)-(4-(3,5-Dichlorobenzenesulfonyl))piperazoyl)-3(R)-amino-3-(4-(2'-methoxyphenyl)phenyl) propionic Acid and N-2(S)-(4-(3,5-Dichlorobenzenesulfonyl))piperazoyl)-3(R)-amino-3-(4-(2'-methoxyphenyl)phenyl)propionic Acid.

The title compounds were made by sulfonylating 2(R,S)-piperazyl-3(R)-amino-3-(4-(2'-methoxyphenyl)phenyl) propionic acid, methyl ester with 3,5-dichlorbenzenesulfonyl chloride as described in Example 23, Step G. The diastereomeric product mixture of esters was separated by flash chromatographyon silica gel eluted with ethyl acetate. The respective esters were hydrolyzed and reacidified as described in Example 39, Step F.

Each diastereomer: MS: m/e 621 (M+NH$_4^+$).

EXAMPLE 82

N-(2-(R,S)-1-N-(Benzenesulfonyl)piperazoyl)-3(R)-amino-3-(4-(2'-methoxyphenyl)phenyl)propionic Acid Step A. 2-(R,S)-4-(Benzyloxycarbonyl)piperazic Acid, Methyl Ester.

The title compound was prepared by treating 4-(benzyloxycarbonyl)-1-(t-butyloxycarbonyl)piperazine-2(R,S)-carboxylic acid, (760 mg, 2.0 mmol) from Example 79, Step A with 1 eq of trimethylsilyldiazomethane (2.0 N, Aldrich) in 1:2 methanol:benzene. The solvents were removed under reduced pressure and the crude product treated with 10 eq of trifluoroacetic acid (5 g) in methylene chloride (20 mL) overnight. The TFA was removed under reduced pressure and the residual TFA azeotroped with toluene under reduced pressure. The TFA salt was neutralized with saturated sodium bicarbonate solution and extracted with methyene chloride. The solution was dried over anhydrous MgSO$_4$, filtered and the solvent removed under reduced pressure. Flash chromatography on silica gel eluted with ethyl acetate gave 280 mg (50%) of title compound.

MS: m/e 436: (M+NH$_4^+$).

Step B. 2(R,S)-1-(Benzenesulfonyl)-4-(benzyloxycarbonyl) piperazic Acid.

2-(R,S)-4-(Benzyloxycarbonyl)piperazic acid, methyl ester (278 mg, 1.0 mmol) was reacted with benzenesulfonyl chloride (237 mg, 1.2 mmol) as taught in Example 23, Step G to provide 390 mg of the methyl ester of the title compound, which was subsequently hydrolyzed by the method in Example 39, Step F to provide the title compound.

400 MHz $^1$H NMR (CDCl$_3$): δ 2.85–3.50 (m, 3H), 3.70 (m, 1H), 4.0–4.2 (m, 1H), 4.5–4.7 (m, 2H), 5.02 (d, 1H, J=13 Hz), 5.06 (d, 1H, J=13 Hz), 7.25–7.34 (m, 5H), 7.45–7.6 (m, 3H), 7.75 (m, 2H),

Step C. N-(2(R,S)-1-N-(Benzenesulfonyl)-4-(benzyloxycarbonyl)piperazoyl)-3(R)-amino-3-(4-(2'-methoxyphenyl)phenyl)propionic Acid, Methl Ester.

The title compound was prepared by treating 2(R,S)-1-benzenesulfonyl-4-(benzyloxycarbonyl)piperazic acid (95 mg, 0.35 mmol) with 3(R)-amino-3-(4-(2'methoxyphenyl)phenyl)propionic acid,methyl ester hydrochloride (87 mg, 0.28 mmol), (synthesized in Example 39, Step D) and coupled as taught in Example 39, Step E to provide 56 mg (0.08 mmol) of the title compound after flash chromatography on silica gel eluted with 60:40 hexane:ethyl acetate.

MS: m/e 689: (M+NH$_4^+$).

Step D. N-(2(R,S)-1-(Benzenesulfonyl)piperazoyl)-3(R)-amino-3-(4-(2'-methoxyphenyl)phenyl)propionic Acid N-(2(R,S)-(1-(Benzenesulfonyl)-4-(benzyloxycarbonyl)) piperazoyl)-3(R)-amino-3-(4-(2'-methoxyphenyl)phenyl) propionic acid (56 mg, 0.08 mmol) was hydrogenolyzed (1 atm) over 10% Pd/C in methanol. The methyl ester was hydrolyzed with NaOH solution and acidified as previously taught in Example 39, Step F to yield the title compound (13 mg).

MS: m/e 541: (M+NH$_4^+$).

EXAMPLE 83

N-(2(S)-1-(3,5-Dichlorobenzenesulfonyl)-4-methylpiperazoyl)-3(R)-amino-3-(4-(2'-methoxyphenyl)phenyl)propionic Acid Step A. 4-(Benzyloxycarbonyl)piperazine-2(S)-carboxylic Acid, Methyl Ester The title compound was made from 2-(S)-4-(benzyloxycarbonyl)-piperazine-2-carboxylic acid by the method shown in Example 82, Step A. The chiral piperazic acid was obtained by the method of Felder et al., *Helv. chem. Acta.* (43), p 888 (1960).

400 MHz $^1$H NMR (CD$_3$OD): 2.6–2.7 (m, 1H), 2.9–3.0 (m, 1H), 3.15–3.25 (m, 1H), 3.46 (d, 1H, J=4 Hz), 3.48 (d, 1H, J=4 Hz), 3.7 (m, 5H), 5.1 (m, 2H), 7.3–7.5 (m, 5H).

Step B. (1-(3,5-dichlorobenzenesulfonyl)-4-(benzyloxycarbonyl))piperazine-2(S)-carboxylic Acid, Methyl Ester The title compound was prepared by reacting 2(S)-4-(benzyloxycarbonyl)piperazine-2-carboxylic acid, methyl ester with 3,5-dichlorobenzenenesulfonyl chloride as taught in Example 28, Step D.

400 MHz $^1$H NMR (CDCl$_3$): 2.9–3.0 (m, 1H), 3.15–3.25 (m, 1H), 3.3–3.4 (m, 2H), 3.5–3.6 (m, 1H), 4.1–4.3 (bd, 1H), 5.0 (d, 1H, J=12 Hz), 7.2–7.35 (m, 5H), 7.53 (t, 1H, J=2 Hz), 7.59 (t, 2H; J=2 Hz).

Step C. 1-(3,5-Dichlorobenzenesulfonyl)piperazine-2(S)-carboxylic Acid, Methyl Ester (1-(3,5-Dichlorobenzenesulfonyl)-4-(benzyloxycarbonyl))piperazine-2(S)-carboxylic acid, methyl ester (56 mg, 0.08 mmol) was hydrogenolyzed by the method shown in Example 81, Step D to yield the title compound.

400 MHz $^1$H NMR (CDCl$_3$): 2.82 (dt, 1H, J=14 Hz, J=3 Hz), 3.0 (dd, 2H, J=14 Hz, J=3 Hz), ): 3.26 (dt, 1H, J=14 Hz, J=3 Hz), 3.3–3.4 (m, 1H), 3.5–3.6 (m, 3H), 4.55 (m, 1H), 7.52 (t, 1H, J=2 Hz), 7.61 (t, 2H, J=2 Hz).

Step D. 1-(3,5-Dichlorobenzenesulfonyl)-4-methyl-piperazine-2(S)-carboxylic Acid, Hydrochloride 1-(3,5-Dichlorobenzenesulfonyl)piperazine-2(S)-carboxylic acid, methyl ester (55 mg, 0.16 mmol) was added to a 5 mL round bottom flask containing 2 mL of acetonitrile and 37% formaldehyde (63 mg, 0.78 mmol) at 0°. Sodium cyanoborohydride (30 mg, 3 equivalents) was added portionwise over 10 minutes. The mixture was stirred at 25° for 2 hours. The solvent was removed under reduced pressure and the residue partitioned between methylene chloride and 1N HCl. The aqueous layer was neutralized with saturated sodium bicarbonate and extracted with methylene chloride. The organic layer was dried over anhydrous magnesium sulfate, filtered, and the solvent removed under reduced pressure. Flash chromatography on silica gel eluted with (98/2/0.1 methylene chloride/methanol/acetic acid) gave 38 mg of 1-(3,5-dichlorobenzenesulfonyl)-4-methyl-piperazine-2(S)-carboxylic acid, methyl ester. The methyl ester was hydrolysed and isolated as described in Example 39, Step F.

MS: m/e 370: (M+NH$_4^+$).

Step F. N-(2(S)-1-(3,5-Dichlorobenzenesulfonyl)-4-methylpiperazoyl)-3(R)-amino-3-(4-(2'-methoxyphenyl) phenyl)propionic Acid 1-(3,5-Dichlorobenzenesulfonyl)-4-methyl-piperazine-2 (S)-carboxylic acid, hydrochloride (25 mg, 0.071 mmol) was coupled with 3(R)-amino-(4-(2'-methoxyphenyl) phenyl)propionic acid,methyl ester hydrochloride (25 mg, 0.078 mmol) according to the procedure in Example 39, Step E to provided 14 mg of the methyl ester of the title compound after flash chromatography on silica gel eluting with 75/25 hexane/ethyl acetate. The ester was hydrolysed as previously taught (Example 39, Step F) and the product isolated as the hydrochloride salt.

MS: m/e 648: (M+NH$_4^+$).

EXAMPLE 84

N-(3,5-Dichlorobenzenesulfonyl)-2(S)-prolyl-3(R)-amino-3-(4-(2'-cyclopropyloxy)biphenyl)propionic Acid The title compound was prepared by the method described for Example 28. The 2-cyclopropyloxyphenylboronic acid was prepared by the method of V. Snieckus et al. (*J. Org. Chem.* 1991, 56, 3763) from 1-bromo-2-cyclopropyloxybenzene (Petinskii, A. A. et al. Bull. Acad. Sci. USSR Div. Chem. Sci. (Engl. Transl.) 1972, 21 1720) via lithium halogen. The final product (34 mg) was obtained after NaOH hydrolysis of the ester.

500 MHz $^1$H NMR (CD$_3$OD): δ 0.60–0.66 (m, 2H), 0.70–0.76 (m, 2H), 1.7–1.8 (m, 1H), 1.95–2.05 (m, 3H), 2.90–2.95 (m, 2H), 3.3–3.4 (m, 1H), 3.5–3.6 (m, 1H), 3.76 (tt, J=6.0, 3.0 Hz, 1H), 4.22–4.30 (m, 1H), 5.36 (dd, J=7.0, 7.0 Hz, 1H), 7.00 (td, J=7.5, 1.0 Hz, 1H), 7.26 (dd, J=7.5, 1.5 Hz, 1H), 7.29 (ddd, J=7.5, 7.5. 1.5 Hz, 1H), 7.36–7.46 (m, 5H), 7.73 (t, J=1.5 Hz, 1H), 7.78 (d, J=1.5 Hz. 2H). MS: m/e 620 (M+NH$_4$).

EXAMPLE 85

N-(3,5-Dichlorobenzenesulfonyl)-2-methyl-2(S)-prolyl-3(R)-amino-3-(4-(2'-cyclopropyloxy) biphenyl)propionic Acid The title compound was prepared by the methods described in Examples 39 and 84 substituting N-(3,5- dichlorobenzenesulfonyl)-2-methyl-2(S)-proline for N-(3,5-dichlorobenzenesulfonyl)-2(S)-proline in the coupling reaction. The final product (82 mg) was obtained after NaOH hydrolysis of the ester.

500 MHz $^1$H NMR (CD$_3$OD): δ 0.58–0.64 (m, 2H), 0.70–0.76 (m, 2H), 1.67 (s, 1H), 1.86–2.00 (m, 3H), 2.22–2.28 (m, 1H), 2.88–3.00 (m, 2H), 3.44–3.52 (m, 1H), 3.54–3.60 (m, 1H), 3.75 (tt, J=6.0, 3.0 Hz, 1H), 5.34–5.40 (m, 1H), 6.99 (td, J=7.0, 1.5 Hz, 1H), 7.25 (dd, J=7.5, 2.0 Hz, 1H), 7.29 (ddd, J=7.5, 7.0. 1.5 Hz, 1H), 7.37 (dd, J=7.5, 1.5 Hz, 1H), 7.39–7.44 (m, 4H), 7.68–7.72 (m, 3H). MS: m/e 634 (M+NH$_4$).

EXAMPLE 86

N-(3,5-Dichlorobenzenesulfonyl)-2(S)-prolyl-3(R)-amino-3-(4-(trifluoromethoxy)phenyl)propionic Acid Step A. 3-(4-Trifluoromethoxyphenyl)acrylic Acid, Ethyl Ester In a 100 mL round bottomed flask fitted with a magnetic stirrer bar and rubber septum was added trichlorooxybis(triphenylphosphine)rhenium(V) (250 mg, 0.3 mmol) in 75 mL of dry THF and 5 mL of triethylphosphite. To this mixture was added 4-trifluoromethoxybenzaldehyde (5.7 g, 30 mmol) (Acros Chemical Co.) at 240. Then ethyl diazoacetate (3.54 g, 31 mmol) was added dropwise over 15 minutes. Gas evolution started within 10 min and ceased after 40 min. Stirred an additional 2 hr, then poured into 250 mL of cold water. The solution was extracted with ether (2×100 mL). The organic layer was back extracted with cold brine (1×100 ml) and dried over magnesium sulfate. Flash chomatography (90/10 hexane/ethyl acetate) gave 7.8 g (7 mmol) of the title compound.

300 MHz $^1$H NMR (CDCl$_3$): δ 1.34 (t, J=7 Hz, 3H), 4.27(q, J=7 Hz, 2H), 6.40 (d, J=16 Hz, 1H), 7.23 (d, J=8 Hz, 2H), 7.54 (d, J=7 Hz, 2H), 7.65 (d, J=16 Hz, 1H).

Step B. 3-(4-Trifluoromethoxyphenyl)-3(R)-[benzyl-(1(S)-phenylethyl)-amino]propionic Acid, Ethyl Ester This intermediate was synthesized by the procedure taught in Step C of Example 28 by addition of 3-(4-trifluoromethoxyphenyl)-acrylic acid, ethyl ester (1.5 g, 5.8 mmol) to the lithium salt of (S)-(-)-N-benzyl-1-phenylethylamine (2.43 g, 11.5 mmol) at −78° C. Workup and flash chromatography (80/20 hexane/ethyl acetate) as described therein gave 1.6 g (58%) of desired product.

400 MHz $^1$H NMR (CDCl$_3$): δ 1.21 (d, 2H, J=7 Hz), 1.34 (t, J=7 Hz, 3H), 2.62 (dd, 1H, J=13 Hz, J=10 Hz), 2.72 (dd, 1H J=13 Hz, J=6 Hz), 3.62 (s, 2H), 3.97 (q, J=6 Hz, 1H), 4.30(q, J=7 Hz, 2H), 4.36 (dd, 1H, J=9 Hz, J=6 Hz), 6.93 (d, 2H, J=9 Hz), 7.2–7.5 (m, 12 H).

Step C. 3(R)-Amino-3-(4-trifluoromethoxphenyl)propionic Acid, Ethyl Ester, Acetic Acid Salt This intermediate was synthesized by the procedure taught in Step D of Example 28 by hydrogenolysis of 3-(4-trifluoromethoxyphenyl)-3(R)-[benzyl-(1(S)-phenylethyl)-amino]propionic acid, ethyl ester in a Parr shaker bottle in ethanol at 60 psi of hydrogen. Recovered 1.1 g of the product as the acetate salt which was used without further purification.

Step D. N-(3,5-Dichlorobenzenesulfonyl)-2(S)-prolyl-3(R)-amino-3-(4-trifluoromethoxphenyl)propionic Acid, Methyl Ester.

This intermediate was synthesized by the procedure taught in Example 39, Step E wherein 3(R)-amino-3-(4-trifluoromethoxyphenyl)propionic acid, ethyl ester, acetic acid salt (220 mg, 0.65 mmol) was coupled with N-(3,5-dichlorobenzenesulfonyl)-(L)-proline, synthesized in Example 22, Step G, (200 mg, 0.62 mmol) using PyBOP (484 mg, 0.93 mmol) and DIPEA (0.5 mL, 2.5 mmol). Workup and chromatography (80/20 hexanes/ethyl acetate) gave 100 mg of coupled product, which was hydrolysed as described below Step E. N-(3,5-Dichlorobenzenesulfonyl)-2(S)-prolyl-3(R)-amino-3-(4-trifluoromethoxphenyl)propionic Acid.

The ester in Step D was hydrolysed to the free acid by adding to 2 equivalents of NaOH in 3/1 ethanol/water at room temperature. When the hydrolysis was complete, the solvent was removed under reduced pressure and the residuce was acidified with 2.5 N HCl. The product was extracted with methylene chloride and chromatographed with (98/1.8/0.2) CH$_2$Cl$_2$/MeOH/AcOH) to provide 50 mg of the title compound.

400 MHz $^1$H NMR (CDCl$_3$): δ 1.6–1.8 (m, 4H), 2.81 (m, 2H), 3.0–3.1 (m, 2H), 3.6–3.7 (m, 1H), 4.18 (m, 1H), 5.3–5.4 (m, 1H), 7.11 (d, 2H, J=8 Hz), 7.30 (d, 2H, J=8 Hz), 7.65–7.80 (t, J=2 Hz, 1H), 7.69 (d, J=2 Hz, 2H). MS: m/e 555 (M$^+$).

EXAMPLE 87

N-(3,5-Dichlorobenzenesulfonyl)-2(S)-prolyl-3(R)-amino-3-(2-(fluorophenyl)propionic Acid This compound was synthesized by coupling 3(R,S)-amino-3-(2-fluorophenyl)propionic acid (Aldrich Chemical Co) with N-(3,5-dichlorobenzene-sulfonyl)-2-methyl-2(S)-proline using the procedure described in Example 39, Step E. The higher R$_f$ diastereoisomer product was separated by flash chomatography and the ester was hydrolyzed as described in Example 39, Step F.

MS: m/e 503 (M$^+$).

EXAMPLE 88

N-(3,5-Dichlorobenzenesulfonyl)-2(S)-azetidinecarbonyl-3(R)-amino-3-(4-methoxyphenyl) propionic Acid Step A. N-(3,5-Dichlorobenzenesulfonyl)-2(S)-azetidinecarboxylic Acid To a magnetically stirred mixture of azetidine-2(S)-carboxylic acid (1 g, 10.5 mmol) and Na$_2$CO$_3$ (2.76 g, 20 mmol) in 15 mL of water at 0° C. was added 3.5-dichlorobenzenesulfonyl chloride (2.94 g, 12 mmol), and the reaction was allowed to slowly warm up to room temperature overnight. The reaction was quenched by careful addition of concentrated HCl at 0° C. (pH=ca. 2), and the product was extracted with EtOAc (3×15 mL). The extracts were dried over Na$_2$SO$_4$, and concentrated to dryness to provide the final product as a white solid, which is >90% pure by $^1$H NMR and was used directly.

500 MHz $^1$H NMR (CD$_3$OD): δ 2.3–2.4 (m, 2H), 3.39 (m, 1H), 3.95 (q, J=9 Hz, 1H), 4.68 (t, 1H, J=8.5 Hz), 7.62 (t, 1H, J=8 Hz), 7.73–7.70 (m, 1H), 7.79 (t, J=2 Hz, 1H), 7.84 (d, J=2 Hz, 1H).

Step B. N-(3,5-Dichlorobenzenesulfonyl)-2(S)-azetidinecarbonyl-3(R)-amino-3-(4-methoxyphenyl) propionic Acid, Methyl Ester.

This material was obtained by coupling N-(3,5-dichlorobenzene-sulfonyl)-2(S)-azetidinecarboxylic acid with 3(R)-arnino-3-(4-methoxyphenyl)propionic acid, methyl ester (prepared in Example 57). Recovered 29 mg.

400 MHz $^1$H NMR (CDCl$_3$): δ 2.2–2.4 (m, 2H), 2.90 (dd, 1H, J=16 Hz, J=6 Hz), 3.02 (dd, 1H, J=16 Hz, J=6 Hz), 3.68 (s, 3H), 3.70 (m, 1H), 3.80 (m, 1H), 3.82 (s, 3H), 4.40 (t, 1H,

J=8 Hz), 5.40 (q, 1H, J=8 Hz), 7.90 (d, 2H. J=7 Hz), 7.31 (d, 2H, J=7 Hz), 7.69 (d, J=2 Hz, 1H), 7.72 (d, J=2 Hz, 2H).
Step C. N-(3,5-Dichlorobenzenesulfonyl)-2(S)-azetidinecarbonyl-3(R)-amino-3-(4-methoxyphenyl) propionic Acid.

This material was obtained by ester hydrolysis of the material described above in Step B using 2 equivalents of LiOH in 5:1 ethanol:water, and stirring at 25° for 2–4 hr. The solvent was stripped under reduced pressure and reacidified with 0.5 N aqueous HCl. Recovered 22 mg of product.

400 MHz $^1$H NMR (CDCl$_3$): δ 2.2–2.4 (m, 2H), 2.90 (dd, 1H, J=16 Hz, J=6 Hz), 3.02 (dd, 1H, J=16 Hz, J=6 Hz), 3.70 (m, 1H), 3.83 (m, 1H), 3.82 (s, 3H), 4.40 (t, 1H, J=8 Hz), 5.40 (q, 1H, J=8 Hz), 7.94 (d, 2H, J=7 Hz), 7.31 (d, 2H, J=7 Hz), 7.665 (d, J=2 Hz, 1H), 7.70 (d, J=2 Hz, 2H). MS: m/e 488 (M$^+$1).

EXAMPLE 89

N-(3,5-Dichlorobenzenesulfonyl)-2(S)-azetidinecarbonyl-3(R)-amino-3-phenylpropionic Acid This compound was synthesized by coupling 3(R)-amino-3-(phenyl)-propionic (Oxford Asymmetry Co) with N-(3,5-dichlorobenzenesulfonyl)-2(S)-azetidinecarboxylic acid using the procedure described in Example 39, Step E. The coupled product was separated by flash chomatography and the ester was hydrolyzed as described in Example 39, Step F. MS: m/e 457 (M$^+$).

The following compounds were prepared by the procedures described in Example 39, Step C by coupling the appropriate aryl boronic acid to N-tert-butoxycarbonyl-3(R)-amino-3-(4-trifluoromethylsulfonyloxyphenyl) propionic acid, methyl ester. Three of the aryl boronic acids used herein are commercially available: 2-methoxybenzeneboronic acid (Lancaster Chemical Co), 2,5-dimethoxybenzene boronic acid and 2,6-dimethoxybenzene boronic acid (Frontier Chemical Co). Both 2-trifluoromethoxy-6-methoxybenzene boronic acid and 2-fluoro-4,6-dimethoxybenzene boronic acid were synthesized as taught by M. Schlosser et al in *Synlett—Stuttgart*, 731(1991), from the corresponding aromatic hydrocarbon by transmetallation with n-butyl or t-butyllithium for 8 hours in THF at −78°, followed by treatment with a trialkoxyboronate then subsequent hydrolysis with 2.5 N aqueous HCl. The 2,6-dimethoxy 3-fluorobenzene boronic acid and 2,6-dimethoxy 3,4-difluorobenzene boronic acid was synthesized from 2,6-dimethoxybenzene boronic acid as taught by A. J. Poss et al in *Chemica Oggi: Chemistri Today* (13) p47 (1995) using one and two equivalents of 1-fluoro-4-chloromethyl-1,4-diazoniabicyclo[2.2.2]octane bis(tetrafluoroborate), respectively.

After Boc-deprotection (Example 39, Step D), the resultant β-aminoacid hydrochloride was coupled to either N-(3, 5-dichlorobenzenesulfonyl)-2-methyl-2(S)-proline, N-(3,5-dichlorobenzenesulfonyl)-2(S)-proline or N-(3,5-dichlorobenzenesulfonyl)-2(S)-azetidinecarboxylic acid by the method taught in Example 39, Step E and hydrolysed to the free acid as described in Example 88, Step C For the compound of Example 90, the starting material N-(benzenesulfonyl)-2-methyl-2(S)-proline was synthesized by the procedure taught in Example 22, Step G using benzenesulfonyl chloride instead of 3,5-dichlorobenzenesulfonyl chloride.

| Ex. No | Compound Name | MS* |
|---|---|---|
| (90) | N-(benzenesulfonyl)-2-methyl-2(S)-prolyl-3(R)-amino-3-(4-(2',6'-dimethoxyphenyl)phenyl)-propionic acid | 552 (M$^+$) |
| (91) | N-(3,5-dichlorobenzenesulfonyl)-2(S)-prolyl-3(R)-amino-3-(4-(2',6'-dimethoxyphenyl)phenyl)propionic acid | 607 (M$^+$) |
| (92) | N-(3,5-dichlorobenzenesulfonyl)-2-methyl-2(S)-prolyl-3(R)-amino-3-(4-(2',6'dimethoxyphenyl)phenyl)propionic acid | 621 (M$^+$) |
| (93) | N-(3,5-dichlorobenzenesulfonyl)-2(S)-azetidinecarbonyl-3(R)-amino-3-(4-(2',6'-dimethoxyphenyl)phenyl)propionic acid | 645 (M + 1) |
| (94) | N-(3,5-dichlorobenzenesulfonyl)-2(S)-azetidinecarbonyl-3(R)-amino-3-(4-(2'-methoxyphenyl)phenyl)propionic acid | 564 (M + 1) |
| (95) | N-(3,5-dichlorobenzenesulfonyl)-2(S)-prolyl-3(R)-amino-3-(4-(2',5'-dimethoxyphenyl)phenyl)propionic acid | 607 (M$^+$) |
| (96) | N-(3,5-dichlorobenzenesulfonyl)-2-methyl-2(S)-prolyl-3(R)-amino-3-(4-(2',5'-dimethoxyphenyl)phenyl)propionic acid | 621 (M$^+$) |
| (97) | N-(3,5-dichlorobenzenesulfonyl)-2-methyl-2(S)-prolyl-3(R)-amino-3-(4-(2'-trifluoromethoxy-6'-methoxyphenyl)phenyl)-propionic acid | 675 (M$^+$) |
| (98) | N-(3,5-dichlorobenzenesulfonyl)-2-methyl-2(S)-azetidine-carbonyl-3(R)-amino-3-(4-(2'-trifluoromethoxy-6'-methoxy-phenyl)phenyl)propionic acid | 647 (M$^+$) |
| (99) | N-(3,5-dichlorobenzenesulfonyl)-2(S)-azetidinecarbonyl-3(R)-amino-3-(4-(2'-fluoro-4', 6'-dimethoxyphenyl)phenyl)-propionic acid | 612 (M + 1) |
| (100) | N-(3,5-dichlorobenzenesulfonyl)-2-methyl-2(S)-prolyl-3(R)-amino-3-(4-(2'-fluoro-4', 6'-dimethoxyphenyl)phenyl)-propionic acid | 639 (M$^+$) |
| (101) | N-(3,5-dichlorobenzenesulfonyl)-2-methyl-2(S)-prolyl-3(R)-amino-3-(4-(2',6'-dimethoxy-3'-fluorophenyl)phenyl)-propionic acid | 639 (M$^+$) |
| (102) | N-(3,5-dichlorobenzenesulfonyl)-2(S)-prolyl-3(R)-amino-3-(4-(2',6'-dimethoxy-3'-fluorophenyl)phenyl)propionic acid | 625 (M$^+$) |

-continued

| Ex. No | Compound Name | MS* |
|---|---|---|
| (103) | N-(3,5-dichlorobenzenesulfonyl)-2(S)-azetidinecarbonyl-3(R)-amino-3-(4-(2',6'-dimethoxy-3'-fluorophenyl)phenyl)-propionic acid | 611 (M+) |
| (104) | N-(3,5-dichlorobenzenesulfonyl)-2-methyl-2(S)-prolyl-3(R)-amino-3-(4-(2',6'dimethoxy-3',5'-difluorophenyl)phenyl)-propionic acid | 657 (M+) |

*m/e: (M + 1 (H+))+ or (M + 18 (NH$_4$+))+

EXAMPLE 105

N-(3-(3,5-Dichlorobenzenesulfonyl)oxazolidine-4 (S)-carbonyl)-3(R)-amino-3-(4-(2'-methoxyphenyl) phenyl)propionic Acid Step A. 3-(tert-butyloxycarbonyl)oxazolidine-4(S)-carboxylic Acid.

To 100 mL round bottom flask fitted with a magnetic stir bar was added L-serine (3.15 g, 30 mmol), 2 N NaOH (15 mL) and 37% aqueous formaldehyde. The mixture was stirred at 4° C. overnight and then acetone (30 mL), hydroxylamine hydrochloride (200 mg, 3 mmol) and 5 N NaOH (6 mL, 30 mmol) was added with cooling. After 10 minutes, di-tert-butyl-dicarbonate (7.2 g, 33 mmol) was added in one portion. The mixture was stirred at 0° C. for 1 hr, warmed to room temperature and stirred for another 4 hours. The solution was worked up by adding 200 mL of water, then extracted with 3×100 mL of ether. The ether layer was discarded and the aqueous layer acidified to pH=5 with 10% citric acid. The aqueous layer was extracted with ethyl acetate (3×100 mL), dried over anhydrous MgSO$_4$, filtered and the solvent removed under reduced pressure. Recovered 5.0 g (23 mmol of product (73%).

400 MHz $^1$H NMR (CDCl$_3$): δ 1.34 1.50 (s, 9H), 4.20 (bs, 2H), 5.50 (bs, 1H), 4.8–5.05 (m, 2H)

Step B. 3-(tert-Butyloxycarbonyl)oxazolidine-4(S)-carboxylic Acid, Methyl Ester.

The material from Step A was dissolved in 10 mL of methanol and 20 mL of benzene. The mixture was cooled to 0° C. and trimethylsilyldiazomethane (13 mL, 2N in hexane (Aldrich)) was added dropwise until the solution's color persisted. Then a few drops of acetic acid was added and the solvent stripped off under reduced pressure.

400 MHz $^1$H NMR (CDCl$_3$): δ 1.47(s, 9H), 3.78 (s, 3H), 4.2–4.3(bs, 2H), 4.9–5.1 (bs, 3H).

Step C. 3-(3,5-Dichlorobenzenesulfonyl)oxazolidine-4(S)-carboxylic Acid, Methyl Ester.

The Boc group of the material from Step B was deprotected by stirring it in 50 mL of 1N HCl in ethyl acetate (1 hr). The solvent was stripped and 910 mg (5.4 mmol) of this material was dissolved in 10 mL of a 1:1 mixture of methylene chloride and THF. Then 2.78 mL (16.2 mmol) of DIPEA was added to the cooled (0° C.) reaction mixture and 3,5-dichlorobenzenesulfonyl chloride (1.45 g, 5.9 mmol) was added portionwise. The mixture was warmed to room temperature and stirred overnight. The reaction mixture was poured into 30 mL of 1 N HCl and the product extracted with dichloromethane. The solution was dried over MgSO$_4$, filtered and the solvent stripped under reduced pressure. The product was purified by flash chromatography (80/20 hexane/ethyl acetate). Recovered 460 mg of product.

400 MHz $^1$H NMR (CDCl$_3$): δ 3.89 (s, 3H), 3.97 (dd, J=9 Hz, J=5 Hz, 1H), 4.15 (t, J=7 Hz, 1H), 4.50 (dd, J=9 Hz, J=5 Hz, 1H), 4.73 (d, J=5 Hz), 5.21 (d, J=6Hz, 1H), 7.62 (t, J=2 Hz, 1H), 7.78 (d, J=2 Hz, 1H).

Step D. 3-(3,5-Dichlorobenzenesulfonyl)oxazolidine-4(S)-carboxylic Acid.

The methyl ester of the intermediate in Step C was removed by the procedure described in Example 88, Step C. Recovered 300 mg of product.

400 MHz $^1$H NMR (CD$_2$OD): 5.18 (m, 1H), 5.40 (m, 1H), 5.97 (m, 2H), 6.58 (m, 1H), 9.1 (t, J=2 Hz, 1H), 9.2 (d, J=2 Hz, 1H).

Step E. N-(3-(3,5-Dichlorobenzenesulfonyl)oxazolidine-4 (S)-carbonyl)-3(R)-amino-3-(4-(2'-methoxyphenyl)phenyl) propionic Acid, Methyl Ester.

The material in Step D above (33 mg, 0.1 mmol) was coupled with 3(R)-amino-3-(4-(2'-methoxyphenyl)phenyl) propionic acid, methyl ester hydrochloride (36 mg, 0.11 mmol), (prepared in Example 39, Step D) and coupled as taught in the procedure of Example39, Step E. Recovered 30 mg after purification (70/30 hexane/ethyl acetate).

400 MHz $^1$H NMR (CDCl$_3$): δ 2.9–3.1 (m, 2H), 3.7 (s, 3H), 3.83 (s, 3H), 3.97 (dd, J=9 Hz, J=5 Hz, 1H), 4.23 (t, J=7 Hz, 1H), 4.69 (dd, J=9 Hz, J=5 Hz, 1H), 5.21 (d, J=6 Hz, 1H), 5.4–5.5 (m, 1H), 7.03 (m, 2H), 7.3–7.4 (m, 4H), 7.58 (d, J=9 Hz, 1Hz, 1H), 7.64 (t, J=2 Hz, 1H), 7.78 (d, J=2 Hz, 1H), 7.84 (d J=8 Hz, 1H).

Step F. N-(3-(3,5-Dichlorobenzenesulfonyl)oxazolidine-4 (S)-carbonyl)-3(R)-amino-3-(4-(2'-methoxyphenyl)phenyl) propionic Acid.

The methyl ester of the intermediate in Step E above was removed by the procedure described in Example 88, Step C.

400 MHz $^1$H NMR (CDCl$_3$): δ 2.9–3.1 (m, 2H), 3.83 (s, 3H), 3.97 (dd, J=9 Hz, J=9 Hz, 1H), 4.23 (t, J=7 Hz, 1H), 4.69 (dd, J=9 Hz, J=5 Hz, 1H), 5.21 (d, J=6 Hz, 1H), 5.4–5.5 (m, 1H), 7.03 (m, 2H), 7.3–7.4 (m, 4H), 7.58 (d, J=9 Hz, 1H), 7.64 (t, J=2 Hz, 1H), 7.78 (d, J=2 Hz, 1H), 7.84 (d J=8 Hz, 1H). MS: m/e 579 (M+).

EXAMPLE 106

N-(3,5-Dichlorobenzenesulfonyl)-(S)-prolyl-3(R)-amino-3-(4-(2 '-thiazolyl)phenyl)propionic Acid Step A. N-(tert-butoxycarbonyl)-3(R)-amino-3-(4-(2'-thiazolyl)phenyl)-propionic Acid, Methyl Ester N-(tert-Butoxycarbonyl)-3(R)-amino-3-(4-trifluoromethylsulfonyl-oxyphenyl)-propionic acid, methyl ester (0.175 mrnmol, 75 mg; Examples 22 and 23, Step A) and 2-trimethylstannyl thiazole (1.5 equiv; 0.263 mmol, 63.5 mg; J. Organomet. Chem. 1983, 246, 163) were dissolved in anhydrous dimethylformamide (1.0 mL) in a screw-cap vial equipped with a teflon seal and the resulting solution was flushed with nitrogen. Tetrakis (triphenylphosphine)palladium (0) (0.1 equiv; 0.0175 mmol, 20 mg) was added and the reaction mixture was flushed once more with nitrogen and heated at 100° C. for 0.5 h. After this time, an additional portion of stannane and catalyst (1.5 equiv and 10 mol % respectively) was added and heating was continued for 0.5 h. The reaction mixture was diluted with ethyl acetate and washed with saturated potassium fluoride (2×), water, and brine. Drying (MgSO$_4$), filtration, evaporation, and purification by preparative TLC (35% ethyl acetate, 65% hexanes) gave the title compound (35 mg, 55% yield) as an off-white solid.

$^1$H NMR (500 MHz, CDCl$_3$): δ 7.95 (d, 2H, J=8.5 Hz), 7.87 (d, 1H, J=3.5), 7.40 (d, 2H, J=8.5Hz), 7.34(d, 1H, J=3.5Hz), 5.60(brs, 1H), 5.15(brs, 1H), 3.64 (s, 3H), 2.88 (m, 2H), 1.47 (s, 9H).

Step B. N-(3,5-Dichlorobenzenesulfonyl)-(S)-prolyl-3(R)-amino-3-(4-(2'-thiazolyl)phenyl)-propionic Acid, Methyl Ester Deprotection of N-tert-Butoxycarbonyl-3(R)-amino-3-(4-(2'-thiazolyl)phenyl)-propionic acid, methyl ester (0.03 mmol, 11 mg) was carried out as described previously (Example 13, Step E) with anhydrous HCl in ethyl acetate to furnish the corresponding hydrochloride salt (10 mg, 100% yield). The latter (0.033 mmol, 10 mg) was coupled with N-(3,5-Dichlorobenzenesulfonyl)-(S)-proline (1.2 equiv; 0.04 mmol, 13 mg) in dichloromethane/tetrahydrofuran (1:1) as described in Example 13, Step D to provide the title compound (17 mg, 75% yield) after purification by preparative TLC (55% ethyl acetate, 45% hexanes).

$^1$H NMR (500 MHz, CDCl$_3$): δ 7.96 (m, 2H), 7.88 (d, 1H, J=8.5 Hz), 7.87 (d, 1H, J=3.5 Hz), 7.76 (d, 2H, J=1.5 Hz), 7.64 (t, 1H, J=1.5 Hz), 7.40 (m, 2H), 7.35 (d, 1H, J=3.5 Hz), 5.47 (m, 1H), 4.17 (m, 1H), 3.69 (s, 3H), 3.66 (m, 1H), 3.23 (m, 1H), 3.02 (dd, 1H, J=16.0, 5.5 Hz), 2.95 (dd, 1H, J=16.0, 6.0 Hz), 2.24 (m, 1H), 1.81 (m, 3H).

Step C. N-(3,5-Dichlorobenzenesulfonyl)-(S)-prolyl-3(R)-amino-3-(4-(2'-thiazolyl)phenyl)-propionic Acid Hydrolysis of N-(3,5-Dichlorobenzenesulfonyl)-(S)-prolyl-3(R)-amino-3-(4-(2'-thiazolyl)phenyl)-propionic acid, methyl ester obtained in Step B was accomplished as described in Example 13, Step E to give the title compound in quantitative yield.

MS: m/e 554 (M+H), 576 (M+Na); $^1$H NMR (500 MHz, CDCl$_3$): δ 7.99 (d, 1H, J=8.5 Hz), 7.92 (d, 2H, J=8.0 Hz), 7.89 (d, 1H, J=3.0 Hz), 7.73 (brs, 2H), 7.64 (brs, 1H), 7.44 (d, 2H, J=8.0 Hz), 7.34 (d, 1H, J=3.0 Hz), 5.48 (m, 1H), 4.18 (m, 1H), 3.62 (m, 1H), 3.20 (m, 1H), 3.08 (dd, 1H, J=16.0, 5.0Hz), 2.98 (dd, 1H, J=16.0, 5.5Hz), 2.20 (m, 1H), 1.79 (m, 3H).

EXAMPLE 107

N-(3-(3,5-Dichlorobenzenesulfonyl)oxazolidine-4(S)-carbonyl)-3(R)-amino-3-(4-(2',6'-dimethoxyphenyl)phenyl)propionic Acid The title compound was prepared by the methods described in Example 105 substituting amino-3-(4-(2',6'-dimethoxyphenyl)phenyl)propionic acid, methyl ester in the coupling reaction. The final product was obtained after NaOH hydrolysis of the ester.

400 MHz $^1$H NMR (CD$_3$OD): δ 7.9 (d, 1H), 7.65 (d, 1H), 7.18–7.35 (m, 6H), 6.70 (m, 2H), 5.40 (d, 1H), 5.35 (d, 2H), 4.70 (d, 1H), 4.38 (t, 1H), 4.02 (t, 1H), 3.8 (t, 1H), 3.25 (s, 3H), 3.30 (s, 3H), 2.90 (d, 2H).

MS: m/e 609 (M+H).

EXAMPLE 108

N-(3-(3,5-Dichlorobenzenesufonyl)oxazolidine-4(S)-carbonyl)-3(R)-amino-3-phenylpropionic Acid The title compound was prepared by the methods described in Example 105 substituting 3(R)-amino-3-phenyl propionic acid, t-butyl ester in the coupling reaction. The final product was obtained after deprotection of the ester with TFA.

400 MHz $^1$H NMR (CD$_3$OD): δ 7.95 (s, 2H), 7.80 (m, 1H), 7.30–7.40 (m, 5H), 5.35 (m, 1H), 5.25 (d, 1H), 4.65 (d, 1H), 4.36 (t, 1H), 4.00 (t, 1H), 3.75 (t, 1H), 2.83 (m, 2H). MS: m/e 473 (M$^+$+H).

EXAMPLE 109

N-(3-(3,5-Dichlorobenzenesulfonyl)oxazolidine-4(S)-carbonyl)-3(R)-amino-3-(4-methoxyphenyl)propionic Acid The title compound was prepared by the methods described in Example 105 substituting 3(R)-amino-3-(4-methoxyphenyl)propionic acid, methyl ester in the coupling reaction. The final product was obtained after NaOH hydrolysis of the ester.

400 MHz $^1$H NMR (CD$_3$OD): δ 7.9–7.6 (m, 3H), 7.30 (m, 2H), 6.85 (m, 2H), 5.30 (m, 2H), 3.8 (d, 2H), 3.70 (d, 3H), 2.90 (m, 2H), 2.80 (m, 2H). MS: m/e 503 (M$^+$+H).

EXAMPLE 110

N-(3-(3,5-Dichlorobenzenesulfonyl)-4(R,S)-methyl-oxazolidine-4-carbonyl)-3(R)-amino-3-(4-(2',6'-dimethoxyphenyl)phenyl)propionic Acid Step A. 2(R,S)-Methyl-serine, Methyl Ester.

To a 100 mL round bottom flask fitted with a stir bar and septum was added DL-alpha-methyl-serine (3.00 g, 25 mmol) in 25 ml of methanol. Thionyl chloride was added dropwisely at $_0$° C. The reaction mixture was stirred at room temperature for overnight. The solvent removed under reduced pressure. Recovered 3.01 g desired product.

Step B. N-(3,5-Dichlorobenzenesulfonyl)-2(R,S)-methyl-serine, Methyl Ester.

To a 25 mL round bottom flask fitted with a stir bar and septum was added 2(R,S)-methyl-serine, methyl ester (0.5 g, 3.76 mmol) and 3.5-dichlorobenzenesolfonyl chloride (1.01 g, 4.13 mmol) in 6 ml of 1:1 CH$_2$Cl$_2$/THF. Then DIEA was added. The reaction mixture was stirred at room temperature for overnight. The reaction mixture was work up by diluting with ethyl acetate, wash with saturated sodium bicarbonate, saturated sodium chloride and dry with MgSO$_4$. Filtration and evaporation gave the residue purified by flash chromatography (25/75 hexane/ethyl acetate). Recovered 560 mg of product (43.8% yield).

400 MHz $^1$H NMR (CDCl$_3$): δ 7.80 (s, 2H), 7.57 (d, 1H), 6.00 (s, 1H), 3.83 (d 2H), 3.75 (s, 3H), 2.63 (t, 1H), 1.40 (s, 3H).

Step C. 3-(3,5-Dichlorobenzenesulfonyl)-4(R,S)-methyl-oxazolidine-4-carboxylic Acid, Methyl Ester.

To a 15 mL round bottom flask fitted with a stir bar and septum was added N-(3,5-dichlorobenzenesulfonyl)-2(R,S)-methyl-serine, methyl ester (0.1 g, 0.29 mmol) p-toluenesulfonic acid (0.061 g, 0.321 mmol) and paraformaldehyde (0.3 g) in 2 ml of toluene. The reaction mixture was refluxed for two hours. The reaction mixture was work up by diluting with ethyl acetate, wash with saturated sodium bicarbonate, saturated sodium chloride and dru with MgSO$_4$. Filtration and evaporation gave the residue purified by flash chromatography (15/85 hexane/ethyl acetate). Recovered 158 mg of product (50.8% yield). 400 MHz $^1$H NMR (CDCl$_3$): δ 7.78 (s, 2H), 7.58 (d, 1H), 5.01 (m, 2H), 4.25 (d, 1H), 3.90 (d, 1H), 3.75 (s, 3H), 170 (s, 3H).

Step D. 3-(3,5-Dichlorobenzenesulfonyl)-4(R,S)-methyl-oxazolidine-4-carboxylic Acid.

The methyl ester of the intermediate in Step C was removed by the procedure described in Example 88, Step C. Recovered 132 mg of product.

400 MHz $^1$H NMR (CDCl$_3$): δ 7.78 (s, 2H), 7.58 (d, 1H), 5.05 (d, 1H), 5.00 (d, 1H), 4.38 (d, 1H), 3.90 (d, 1H), 1.75 (s, 3H).

Step E. N-(3-(3,5-Dichlorobenzenesulfonyl)-4(R or S)-methyl-oxazolidine-4-carbonyl)-3(R)-amino-3-(4-(2',6'-dimethoxyphenyl)phenyl)propionic Acid, Methyl Ester.

The material in Step D above (30 mg, 0.1 mmol) was coupled with 3(R)-amino-3-(4-(2',6'-dimethoxyphenyl)phenyl)propionic acid, methyl ester hydrochloride (38 mg, 0.1 mmol), and coupled as taught in the procedure of Example 39, Step E. Recovered two isomer, Higher Rf. isomer, 22 mg after purification (65/25 hexane/ethyl acetate). 400 MHz $^1$H NMR (CDCl$_3$): δ 7.9 (d, 1H), 7.8 (s, 2H), 7.60 (s, 1H), 7.25–7.4 (m, 6H), 6.65 (d, 2H), 5.45 (m, 1H), 5.15 (d, 1H), 5.05 (d, 1H), 4.4 (d, 1H), 3.75 (m, 2H), 3.70 (s, 3H), 2.95 (m, 2H), 1.62 (s, 3H).

Step F. N-(3-(3,5-Dichlorobenzenesulfonyl)-4(R or S)-methyl-oxazolidinecarbonyl)-3(R)-amino-3-(4-(2',6'-dimethoxyphenyl)phenyl)propionic Acid.

The less polar isomer from Step E was hydrolyzed with LiOH by the procedure described in Example 88, Step C to yield the title compound.

400 MHz $^1$H NMR (CDCl$_3$): δ 7.90 (d, 1H), 7.80 (s, 2H), 7.60 (s, 1H), 7.25 (m, 5H), 6.65 (d, 2H), 5.50 (m, 1H), 5.15 (d, 1H), 5.05 (d, 1H), 4.4 (d, 1H), 3.71 (s, 6H), 3.65 (d, 1H), 3.20 (m, 2H), 3.00 (m, 2H), 1.60 (s, 3H). MS: m/e 579 (M++23) 645.

EXAMPLE 111

N-(3-(3,5-Dichlorobenzenesulfonyl)-4(R or S)-methyl-oxazolidine-4-carbonyl)-3(R)-amino-3-(4-(2'-methoxyphenyl)phenyl)propionic Acid The title compound was prepared by the methods described in Example 110 substituting 3(R)-amino-3-(4-methoxyphenyl)propionic acid, methyl ester in the coupling reaction. The two isomers were separated after the coupling reaction. The less polar isomer was hydrolyzed with LiOH to yield the title compound.

400 MHz $^1$H NMR (CDCl$_3$): δ 7.82 (d, 1H), 7.75 (s, 2H), 7.60 (s, 1H), 7.25 (d, 2H), 6.85 (d, 2H), 5.35 (m, 1H), 5.05 (d, 1H), 5.00 (d, 1H), 4.38 (d, 1H), 3.80 (s, 3H), 3.65 (d, 1H), 2.90 (m, 2H), 1.55 (s, 3H). MS: m/e 579(M$^+$+23) 539

EXAMPLE 112

N-(3-(Benzenesulfonyl)-4(R or S)-methyl-oxazolidine-4-carbonyl)-3(R)-amino-3-(4-(2',6'-dimethoxyphenyl)phenyl)propionic Acid The title compound was prepared by the methods described in Example 110 substituting benzenesulfonyl chloride in step B. The two isomers were separated after the coupling reaction. The title compound was obtained after LiOH hydrolysis of the less polar ester.

400 MHz $^1$H NMR (CDCl$_3$): δ 7.95 (d, 1H), 7.85 (s, 2H), 7.60 (t, 1H), 7.55 (t, 2H), 7.3–7.4 (m, 4H), 6.65 (d, 2H), 5.50 (m, 1H), 5.07 (m, 2H), 4.4 (d, 1H), 3.75 (s, 6H), 3.65 (d, 1H), 3.00 (m, 2H), 1.55 (s, 3H). MS: m/e 579 (M$^+$+1) 555.

EXAMPLE 113

N-(N-Thiophene-2-sulfonyl-azetidine-2(S)-carbonyl)-3(R)-amino-3-phenylpropionic Acid Step A. N-(2-Thiophene-sulfonyl)-azetidine-2(S)-carboxylic Acid To a magnetically stirred mixture of azetidine-2(S)-carboxylic acid (1.0 g, 10 mmol) and Na$_2$CO$_3$ (2.1 g, 20 mmol) in 30 mL of water at 0° C. was added thiophene-2-sulfonyl chloride (1.8 g, 10 mmol), and the reaction was allowed to slowly warm up to room temperature overnight. The reaction was quenched by careful addition of concentrated HCl at 0° C. to pH above 2, and the product was extracted with EtOAc (3×15 mL). The extracts were dried over Na$_2$SO$_4$, and concentrated to dryness to provide the title compound as a white solid, which is >90% pure by $^1$HNMR and used without further purification.

400 MHz $^1$H NMR (CD$_3$OD): δ 2.2–2.4 (m, 2H), 3.7–3.9 (m, 2H), 4.42 (dd, 1H), 7.30 (dd, 1H), 7.75 (dd, 1H), 7.95 (dd, 1H).

The following compounds were prepared using the same procedure unless otherwise stated:

N-(3-Chlorobenzenesulfonyl)-azetidine-2(S)-carboxylic Acid

500 MHz $^1$H NMR (CD$_3$OD): δ 2.3–2.4 (m, 2H), 3.7–3.9 (m, 2H), 4.58 (t, 1H, J=8.5 Hz), 7.62 (t, 1H, J=8 Hz), 7.73–7.70 (m, 1H), 7.80–7.83 (m, 1H), 7.88–7.90 (m, 1H).

N-(3-Trifluoromethylbenzenesulfonyl)-azetidine-2(S)-carboxylic Acid

400 MHz $^1$H NMR (CD$_3$OD): δ 2.2–2.4 (m, 2H), 3.7–3.9 (m, 2H), 4.59 (dd, 1H), 7.40–7.40 (m, 1H), 7.60–7.78 (m, 3H).

N-(3,5-Dimethylisooxazole-4-sulfonyl)-azetidine-2(S)-carboxylic Acid

400 MHz $^1$H NMR (CD$_3$OD): δ 2.40 (s, 3H), 2.40–2.45 (m, 2H), 2.60 (s, 3H), 3.62–3.76 (m, 1H), 3.95–4.08 (m, 1H), 4.68 (dd, 1H).

N-Benzenesulfonyl-(S)-proline

Ether was used as a cosolvent in this case, which gave similar results.

500 MHz $^1$H NMR (CD$_3$OD): δ 1.62–1.72 (m 1H), 1.88–2.04 (m, 3H), 3.24–3.30 (m, 1H), 3.44–3.50 (m, 1H), 4.2 (dd, 1H), 7.5–8.0 (m, 5H).

N-(3,5-Dichlorobenzenesulfonyl)-3(S)-methyl-(S)-proline

500 MHz $^1$H NMR (CD$_3$OD): δ 0.98 (d, 3H, J=6.5 Hz), 1.4–1.5 (m, 1H), 2.04–2.12 (m, 1H), 2.34–2.44 (m, 1H), 3.38–3.52 (m, 2H), 3.82 (d, 1H, J=5.5 Hz), 7.75–7.80 (m, 1H), 7.82–7.84 (m, 2H).

3-(3,5-Dichlorobenzenesulfonyl)-thiazolidine-4(R)-carboxylic Acid

400 MHz $^1$H NMR (CD$_3$OD): δ 3.18 (ABq d, 2H), 4.40 (d, 1H), 4.80 (d, 1H), 4.96 (dd, 1H), 7.76–7.82 (m, 1H), 7.86–7.92 (m, 2H).

N-(3,5-Dichlorobenzenesulfonyl)-thiazolidine-4(S)-carboxylic Acid

400 MHz $^1$H NMR (CD$_3$OD): δ 3.18 (ABq d, 2H), 4.40 (d, 1H), 4.80 (d, 1H), 4.96 (dd, 1H), 7.76–7.82 (m, 1H), 7.86–7.92 (m, 2H).

Step B. N-(N-(Thiophene-2-sulfonyl)-azetidine-2(S)-carbonyl)-3(R)-amino-3-phenylpropionic Acid, tert-Butyl Ester.

To a solution of 3(R)-amino-3-phenylpropionic acid, tert-butyl ester (89 mg, 0.40 mmol), diisopropylethylamine (DIPEA) (0.14 mL, 0.80 mmol) in 5.0 mL of methylene chloride at 0° C. was added benzotriazol-1-yloxytripyrrolidino phosphonium hexafluorophosphate (PyBOP) (0.22 g, 0.42 mmol). After stirring at room temperature for 3 h, the reaction mixture was directly loaded onto a silica gel column. Eluting with acetone/hexane (4:1) afforded the product as a white foam (165 mg, 91%)

400 MHz $^1$H NMR (CD$_3$OD): δδ 1.35 (s, 9H), 2.15–2.28 (m, 2H), 2.84 (ABq d, 2H), 3.7–3.9 (m, 2H), 4.35 (dd, 1H), 5.35 (dd, 1H), 7.22–7.42 (m, 6H), 7.76 (dd, 1H), 7.89 (dd, 1H); MS: calculated for C$_{21}$H$_{26}$N$_2$O$_5$S$_2$ 450, observed m/e= 395 (M—C$_4$H$_8$+H$^+$)

Step C. N-(N-(Thiophene-2-sulfonyl)-azetidine-2(S)-carbonyl)-3(R)-amino-3-phenylpropionic Acid.

The ester obtained above (0.16 g, 0.36 mmol) was dissolved in methylene chloride (5 mL) and was treated with trifluoroacetic acid (1.4 mL, 18 mmol). After stirring at room temperature for 3 h, the reaction mixture was concentrated to dryness to give the title compound as a foam (0.14 g, 100%).

400 MHz $^1$H NMR (CD$_3$OD): 2.1–2.3 (m, 2H), 2.78–2.96 (m, 2H), 3.7–3.9 (m, 2H), 4.36 (dd, 1H), 5.32–5.40(m, 1H), 7.22–7.42 (m, 6H), 7.76 (dd, 1H), 7.88 (dd, 1H), 8.56 (br d, 1H); MS: calculated for C$_{17}$H$_{18}$N$_2$O$_5$S$_2$ 394, observed m/e= 395 (M+H$^+$).

The following compounds were synthesized in the same manner as described in Example 113.

| Ex No | Name | MS* |
|---|---|---|
| (114) | N-(3-(3,5-dichlorobenzenesulfonyl)-thiazolidine-4(R)-carbonyl)-3(R)-amino-3-phenylpropionic acid | 489 (M + 1) |
| (115) | N-(3-(3,5-dichlorobenzenesulfonyl)-thiazolidine-4(S)-carbonyl)-3(R)-amino-3-phenylpropionic acid | 489 (M + 1) |
| (116) | N-(3-(3,5-dichlorobenzenesulfonyl)-3(S)-methyl-2(S)-prolyl)-3(R)-amino-3-phenylpropionic acid | 485 (M + 1) |

Examples 117 to 119 were synthesized following the procedure described for Example 84 substituting the appropriate carboxylic acid (Example 115, Step A) for N-(3,5-dichlorobenzenesulfonyl)-2(S)—

| Ex No | Name | MS* |
|---|---|---|
| (117) | N-(N-Benzenesulfonyl-2(S)-prolyl)-3(R)-amino-3-(4-(2'-cyclopropyloxyphenyl)phenyl)propionic acid | 535 (M + 1) |
| (118) | N-(N-(3-Trifluoromethylbenzenesulfonyl)-2(S)-prolyl)-3(R)-amino-3-(4-(2'-cyclopropyloxyphenyl)phenyl)-propionic acid | 603 (M + 1) |
| (119) | N-(N-(3-Chlorobenzenesulfonyl)azetidine-2(S)-carboxyl)-3(R)-amino-3-(4-(2'-cyclopropyloxyphenyl)-phenyl)propionic acid | 555 (M + 1) |

*m/e: (M + 1 (H$^+$))$^+$ or (M + 18 (NH$_4^+$))$^+$

EXAMPLE 120

N-(N-Benzenesulfonyl-4,4-difluoro-(S)-prolyl)-3 (R)-amino-3-(4-(2'-cyclopropyloxyphenyl)phenyl) propionic Acid Step A. 4,4-Difluoro-(S)-proline, Methyl Ester, Hydrochloride Salt.

A mixture of N-tert-butyloxycarbonyl-4(S)-hydroxy-(S)-proline methyl ester (2.0 g, 8.2 mmol), N-methylmorpholine oxide (2.6 g, 22 mmol) and molecular sieves was stirred at room temperature for 10 min, after which tetrabutylammonium peruthenate (0.2 g, 0.12 mmol) was added. After stirring at room temperature overnight, the reaction mixture was concentrated with 10 g of silica gel. The residue was purified on silica gel column eluting with hexane/EtOAc (4:1) to give 1.5 g of the corresponding ketone, which was dissolved in 10 mL of methylene chloride, and was treated with diethylaminosulfur trifluoride (1.6 mL, 12 mmol) at −78° C. The reaction was allowed to slowly warm up to room temperature overnight, and was then quenched with 1.0 mL of triethylamine. The resulting mixture was concentrated, and the residue was purified by silica gel chromatography to give the corresponding difluoro derivative, which was dissolved in 5 mL of ethyl acetate and was treated with 10 mL of concentrated HCl in ethyl acetate at room temperature. After 30 min, the reaction mixture was concentrated to give the title compound (1.1 g).

500 MHz $^1$H NMR (CD$_3$OD): δ 4.85–4.95 (m, 1H), 3.89 (s, 3H), 3.78–3.92 (m, 2 H), 2.94–3.04 (m, 1H), 2.74–2.85 (m, 1H).

Step B. N-Benzenesulfonyl-4,4-difluodro-(S)-proline.

The compound obtained from Step A was converted to N-benzenesulfonyl-4,4-difluoro-(S)-proline methyl ester following the procedure of Step G of Examples 22 and 23. The methyl ester (0.7 g) was then hydrolyzed by treatment with lithium hydroxide (0.3 g) in acetonitrile/water (2:1, 10 mL). The product was obtained as an oil after an extractive workup.

500 MHz $^1$H NMR (CD$_3$OD): δ 7.88–7.94 (m, 2H), 7.66–7.72 (m, 1H), 7.58–7.64 (m, 2H), 4.50 (dd, 1H, J=5.5, 4.5 Hz), 3.7–3.8 (m. 2H), 2.5–2.7 (m, 2H).

Step C. N-(N-Benzenesulfonyl-4,4-difluoro-(S)-prolyl)-3 (R)-amino-3-(4-(2'-cyclopropyloxyphenyl)phenyl) propionic Acid.

The title compound was prepared by the method described for Example 28 by coupling methyl 4-(2'-cyclopropyloxyphenyl)phenyl)propionate and N-benzenesulfonyl-4,4-difluoro-(L)-proline followed by alkaline hydrolysis.

500 MHz $^1$H NMR (CD$_3$OD): δ 0.2–0.8 (m, 4H), 2.4–2.6 (m, 2H), 2.90–2.95 (m, 2H), 3.7–3.9 (m, 3H), 4.42 (dd, 1H), 5.36 (dd, 1H), 7.0–7.8 (m, 13H). MS: m/e 571 (M+NH$_4$).

EXAMPLE 121

N-(N-(3.5-Dichlorobenzenesulfonyl)-azetidine-2(S)-carbonyl)-3(R)-amino-3-(4-(2',6'-dicyclopropyloxyphenyl)phenyl)propionic Acid Step A. 1,3-Dicyclopropyloxybenzene.

A mixture of 1,3-dihydroxybenzene (6.0 g, 54 mmol), cesium carbonate (52 g, 162 mmol), potassium iodide (0.45 g, 2.7 mmol) and cyclopropyl bromide (17 mL, 220 mmol) in 100 mL of dimethylformamide was heated up to 150° C. for 3 days. The reaction mixture was cooled to room temperature and was poured to slurries of ice and ether. The product was extracted with ether (3×10 mL), and was purified on silica gel eluting with hexane/ether (10:1) to give the title compound (3.4 g, 33%) along with a small amount of monocyclopropyl ether (0.18 g).

500 MHz $^1$H NMR (CD$_3$OD): δ 0.5–0.6 (m, 4H), 0.7–0.8 (m, 4H), 3.72 (m, 2H) 6.63 (dd, 2H), 6.70 (t, 1H), 7.13 (t, 1H).

Step B. 1,3-Dicyclopropyloxyphenylboronic Acid.

To a solution of tetramethylethylenediamine (2.7 mL, 18 mmol) in THF (50 mL) at −78° C. was added sec-BuLi (1.3M, 20 mL, 27 mmol). After 10 min, the cyclopropyl ether (3.4 g, 18 mmol) obtained from Step A was added, and the reaction was stirred at −78° C. for 2 h. Trimethyl borate (8.1 mL, 72 mmol) was added in one portion at −78° C., and the reaction was allowed to warm up to room temperature overnight. The reaction mixture was poured to slurries of ice, ether and concentrated HCl. The product was extracted with ether, and was purified on silica gel eluting with hexane/ethyl acetate (3:1) to give the title boronic acid (0.66 g, 16%).

500 MHz $^1$H NMR (CD$_3$OD): δ 0.60–0.66 (m, 4H), 0.72–0.76 (m, 4H), 3.75-(m, 2H), 6.89 (d, 2H, J=8.5 Hz), 7.28 (t, 1H, J=8.5 Hz).

Step C. Methyl N-(tert-Butoxycarbonyl)-3(R)-amino-3-(4-(2',6'-dicyclopropyloxyphenyl)phenyl)propionate.

A degassed mixture of the boronic acid obtained from Step B (0.58 g, 2.4 mmol), potassium carbonate (0.50 g, 3.6 mmol), N-tert-butoxycarbonyl-3(R)-amino-3-(4-trifluoromethylsulfonyloxyphenyl)propionic acid, methyl ester (Example 39, Step B) (1.0 g, 2.4 mmol) and tetrakis(triphenylphosphine)palladium (0.14 g, 0.12 mmol) in toluene (10 mL) and methanol (0.5 mL) was heated up to 90° C. for 3 h. The reaction mixture was cooled to room temperature, and was concentrated with 10 g of silica gel. The product was purified on silica gel eluting with hexane/ethyl acetate (4:1) to give the title compound (0.85 g, 61%).

500 MHz $^1$H NMR (CD$_3$OD): δ 0.50–0.56 (m, 4H), 0.64–0.70 (m, 4H), 1.43 (br s, 9H), 2.80 (br d, 2H), 3.65 (s, 3H), 3.68 (m, 2H), 5.07 (m, 1H), 7.05 (d, 2H), 7.09–7.13; (m, 2H), 7.22–7.27 (m, 3H). MS: m/e 490 (M+Na).

Step D. Methyl 3(R)-amino-3-(4-(2',6'-dicyclopropyloxyphenyl)phenyl)-propionate, Hydrochloride Salt.

The title compound (0.64 g, 88%) was obtained by reaction of methyl N-(tert-butoxycarbonyl)-3(R)-amino-3-(4-(2',6'-dicyclopropyloxyphenyl)phenyl)propionate with hydrogen chloride in ethyl acetate as described in Example 22, Step F.

500 MHz $^1$H NMR (CD$_3$OD): δ 0.46–0.52 (m, 4H), 0.66–0.72 (m, 4H), 3.09 (ABq d, 2H), 3.69 (m, 2H), 3.73 (s, 3H), 4.71 (dd, 1H), 7.04 (d, 2H), 7.25 (br d, 2H), (t, 1H), 7.40 (br d, 2H).

Step E. Methyl N-(N-(3,5-dichlorobenzenesulfonyl)-azetidine-2(S)-carbonyl)-3(R)-amino-3-(4-(2',6'-dicyclopropyloxyphenyl)phenyl)propionate The title compound (81 mg, 61%) was obtained by coupling methyl 3(R)-amino-3-(4-(2',6'-dicyclopropyloxyphenyl)phenyl)propionate hydrochloride salt (Step D) and N-(3,5-dichlorobenzenesulfonyl)-azetidine-2(S)-carboxylic acid (Example 88, Step A) following the procedure described in Example 113, Step B.

500 MHz $^1$H NMR (CD$_3$OD): δ 0.50–0.56 (m, 4H), 0.64–0.68 (m, 4H), 2.26–2.34 (m, 2H), 2.88–2.96 (m, 2H), 3.67 (s, 3H), 3.68 (m, 2H), 3.80–3.86 (m, 2H), 4.49 (t, 1H), 5.40 (br dd, 1H), 7.02 (d, 2H), 7.16 (br d, 2H), 7.26 (t, 1H), 7.31 (br d, 2H), 7.82–7.86 (m, 3H); MS: m/e 659 (M+H)

Step F. N-(N-(3,5-Dichlorobenzenesulfonyl)-azetidine-2(S)-carbonyl)-3(R)-amino-3-(4-(2',6'-dicyclopropyloxyphenyl)phenyl)propionic Acid.

The title compound (77 mg, 97%) was obtained by treatment of N-(N-(3,5-dichlorobenzenesulfonyl)azetidine-2(S)-carbonyl)-3(R)-amino-3-(4-(2',6'-dicyclopropyloxyphenyl)phenyl)propionic acid, methyl ester (Step E) with lithium hydroxide (ca 10 eq) in a 1:1:1 mixture of tetrahydrofuran, methanol and water at room temperature for 3 h, followed by an extractive workup.

500 MHz $^1$H NMR (CD$_3$OD): δ 0.50–0.56 (m, 4H), 0.64–0.68 (m, 4H), 2.26–2.34 (m, 2H), 2.80–2.94 (m, 2H), 3.68 (m, 2H), 3.83 (br t, 2H), 4.53 (t, 1H), 5.38–5.42 (m, 1Y), 7.02 (d, 2H), 7.16 (br d, 2H), 7.24 (t, 1H), 7.33 (br d, 2H), 7.80–7.86 (m, 3H); MS: m/e 645 (M+H)

EXAMPLE 122

N-(N-(3,5-Dichlorobenzenesulfonyl)-azetidine-2(S)-carbonyl)-3(R)-amino-3-(4-(2'-cyclopropyloxy-6'-fluorophenyl)phenyl)propionic Acid Step A. Cyclopropyl 3-fluorophenyl Ether A mixture of 3-fluorophenol (5.4 mL, 60 mmol), cesium carbonate (29 g, 90 mmol), potassium iodide (1.6 g, 9.6 mmol)) and cyclopropyl bromide (7.2 mL, 89 mmol) in 100 mL of dimethylfor1mnamide was heated up to 150° C. for 6 days. The reaction mixture was cooled to room temperature and was poured to a slurry of ice and ether. The product was extracted with ether (3×10 mL), and concentration to dryness provide the product as an oil (6.2 g, 70%).

500 MHz $^1$H NMR (CD$_3$OD): δ 0.66–0.70 (m, 2H), 0.76–0.82 (m, 2H), 3.76-(m, 1H) 6.62–6.68 (m, 1H), 6.76–6.84 (m, 2 H), 7.20–7.26 (m, 1H).

Step B. Methyl 3(R)-Amino-3-(4-(2'-cyclopropyloxy-6'-fluorophenyl)phenyl)-propionate, hydrochloride salt The compound (0.81 g) was obtained by following procedures described in Example 121, Steps B, C and D starting from the cyclopropyl ether obtained at Step A. The material contains some unreacted triflate based on $^1$H NMR, and can be separated at Step C.

400 MHz $^1$H NMR (CD$_3$OD): δ 0.5–0.8 (m, 4H), 3.0–3.2 (m, 2H), 3.70 (s, 3H), 3.76 (m, 1H), 4.75 (m, 1H), 6.58–7.68 (m, 7H).

Step C. N-(N-(3,5-Dichlorobenzenesulfonyl)-azetidine-2(S)-carbonyl)-3(R)-amino-3-(4-(2'-cyclopropyloxy-6'-fluorophenyl)phenyl)propionic acid.

The compound (0.11 g, 38%) was obtained by coupling methyl 3(R)-amino-3-(4-(2'-cyclopropyloxy-6'-fluorophenyl)phenyl)-propionate hydrochloride salt (Step B) and N-(3,5-dichlorobenzenesulfonyl)-azetidine-2(S)-carboxylic acid (Example 88, Step A) followed by alkaline hydrolysis following the procedures described in Example 121, Steps E and F.

400 MHz $^1$H NMR (CD$_3$OD): δ 0.55–0.75 (m, 4H), 2.2–2.4 (m, 2H), 2.8–3.0 (m, 2H), 3.7–3.9 (m, 3H), 4.5–4.6 (m, 1H), 5.3–5.5 (m, 1H), 6.7–7.9 (m, 10H); MS: m/e 607 (M+H)

The following examples were prepared by the procedures described in Example 88 using the appropriate azetidine carboxylic acid (Example 113, Step A).

| Ex No | Name | MS* |
|---|---|---|
| (123) | N-(N-(3-Chlorobenzenesulfonyl)-azetidine-2(S)-carbonyl)-3(R)-amino-3-(4-(2'-cyclopropyloxy-6'-fluororophenyl)phenyl)propionic acid | 573 (M + 1) |
| (124) | N-(N-(Thiophene-2-sulfonyl)-azetidine-2(S)-carbonyl)-3(R)-amino-3-(4-(2'cyclopropyloxy-6'-fluororophenyl)phenyl)propionic acid | 545 (M + 1) |

*m/e: (M + 1 (H$^+$))$^+$ or (M + 18 (NH$_4$$^+$))$^+$

The following examples were prepared by the procedures described in Example 122. The requisite 2,6-dimethoxyphenylboronic acid is commercially available, and the appropriate azetidine carboxylic acid was synthesized in Example 113, Step A.

| Ex No | Name | MS* |
|---|---|---|
| (125) | N-(N-(3-Fluorobenzenesulfonyl)-azetidine-2(S)-carbonyl)-3(R)-amino-3-(4-(2',6'-dimethyoxy-phenyl)phenyl)propionic acid | 543 (M + 1) |
| (126) | N-(N-(Thiophene-2-sulfonyl)-azetidine-2(S)-carbonyl)-3(R)-amino-3-(4-(2',6'-dimethoxyphenyl)phenyl) propionic acid | 531 (M + 1) |

-continued

| Ex No | Name | MS* |
|---|---|---|
| (127) | N-(N-(3,5-Dimethylisooxazole-4-sulfonyl)-azetidine-2(S)-carbonyl)-3(R)-amino-3-(4-(2',6'-dimethyoxy-phenyl)phenyl)propionic acid | 544 (M + 1) |

*m/e: (M + 1 (H+))+ or (M + 18 (NH4+))+

EXAMPLE 128

N-(N-(3,5-Dichlorobenzenesulfonyl)-azetidine-2(S)-carboxyl)-3(R)-amino-3-(4-ethoxyphenyl)propionic Acid.
Step A. Methyl N-tert-Butoxycarbonyl-3(R)-amino-3-(4-ethyoxyphenyl)-propionate.

A mixture of methyl N-tert-butoxycarbonyl-3(R)-amino-3-(4-hydroxy-phenyl)propionate (Example 39, Step A) (0.70 g, 2.4 mmol), cesium carbonate (1.5 g, 4.8 mmol) and iodoethane (0.40 mL, 4.8 mmol) in 4 mL of dimethylformamide was stirred at 60° C. for 30 min. The reaction mixture was cooled to room temperature, and was partitioned between ether and 0.5M potassium hydrogen sulfate. The product was extracted with ether and purified on silica gel eluting with hexane/ethyl acetate (4:1) to give the title compound (0.61 g, 79%).

500 MHz $^1$H NMR (CD$_3$OD): δ 1.36 (t, 3H), 1.40 (br s, 9H), 2.73 (ABq d, 2H), 3.61 (s, 3H), 4.00 (q, 2H), 4.98 (br, 1H), 6.84 (br d, 2H), 7.20 (br d, 2H).

Step B. N-(N-(3,5-Dichlorobenzenesulfonyl)-azetidine-2(S)-carbonyl)-3(R)-amino-3-(4-ethoxyphenyl)propionic Acid.

Methyl N-tert-butoxycarbonyl-3(R)-amino-3-(4-ethyoxyphenyl)-propionate obtained from Step A was treated with hydrogen chloride in ethyl acetate, coupled to N-(3,5-dichlorobenzenesulfonyl)-azetidine-2(S)-carboxylic acid and was hydrolyzed following the procedures of Example 121, Steps D, E and F to give the title compound (136 mg).

500 MHz $^1$H NMR (CD$_3$OD): δ 1.37 (t, 3H), 2.28 (dt, 2H), 2.81 (ABq d, 2H), 3.78–3.85 (m, 2H), 4.01 (q, 2H), 4.98 (br, 1H), 6.84 (br d, 2H), 7.20 (br d, 2H). MS: m/e 501 (M+1)

The following examples were prepared by the procedures described in Example 122. Cyclopentyl bromide and trifluoroethyl methanesulfonate were used respectively at Step A, and the alkyaltion reaction required 3 h at 50° C. and 5 h at 90° C., respectively.

| Ex No | Name | MS* |
|---|---|---|
| (129) | N-(N-(3,5-Dichlorobenzenesulfonyl)-(S)-prolyl-3(R)-amino-3-(4-cyclopentyloxyphenyl)propionic acid | 555 (M + 1) |
| (130) | N-(N-(3,5-Dichlorobenzenesulfonyl)-azetidine-2(S)-carbonyl)-3(R)-amino-3-(4-(2,2,2-trifluoroethoxy) phenyl)propionic acid | 555 (M + 1) |

*m/e: (M + 1 (H+))+ or (M + 18 (NH4+))+

EXAMPLE 131

N-(N-(3,5-Dichlorobenzenesulfonyl)-azetidine-2(S)-carbonyl)-3(R)-amino-3-(4-fluoromethoxyphenyl)propionic Acid
Step A. Methyl N-tert-Butoxycarbonyl-3(R)-amino-3-(4-methylthiomethyoxy-phenyl)propionate.

A mixture of methyl N-tert-butoxycarbonyl-3(R)-amino-3-(4-hydroxy-phenyl)propionate (Example 39, Step A) (0.70 g, 2.4 mmol), cesium carbonate (1.5 g, 4.8 mmol) and chloromethyl methyl thioether (0.40 mL, 4.7 mmol) in 5 mL of dimethylformamide was stirred at room temperature for 2.5 h. Similar workup as in Example 128, Step A provided the title compound (0.62 g, 73%).

500 MHz $^1$H NMR (CD$_3$OD): δ 1.41 (br s, 9H), 2.20 (s, 3H), 2.76 (ABq d, 2H), 3.62 (s, 3H), 4.98 (br, 1H), 5.18 (s, 2H), 6.92 (br d, 2H), 7.23 (br d, 2H).

Step B. Methyl N-tert-Butoxycarbonyl-3(R)-amino-3-(4-fluoromethyoxy-phenyl)propionate.

To a solution of xenon difluoride (0.30 g, 1.8 mmol) in 4 mL of 1,2-dichloroethene at 0° C. (plastic reactor) was added methyl N-tert-butoxycarbonyl-3(R)-amino-3-(4-methylthiomethyoxyphenyl)propionate (Step A) (0.62 g, 1.8 mmol) in 5 mL of 1,2-dichloroethene. After stirring at 0° C. for 30 min and room temperature for 2 h, the reaction was quenched with 0.5 mL of triethylamine, and the mixture was loaded onto a silica gel column. Eluting with hexane/ethyl acetate (4:1) gave the product (225 mg).

500 MHz $_1$H NMR (CD$_3$OD): δ 1.40 (br s, 9H), 2.76 (ABq d, 2H), 3.62 (s, 3H), 5.00 (br, 1H), 5.71 (d, 2H, J=55 Hz), 7.03 (br d, 2H), 7.28 (br d, 2H).

Step C. N-(N-(3,5-Dichlorobenzenesulfonyl)-azetidine-2(S)-carbonyl)-3(R)-arnino-$^3$-(4-fluoromethoxyphenyl) propionic Acid.

Methyl N-tert-butoxycarbonyl-3(R)-amino-3-(4-fluoromethyoxy-phenyl)propionate was converted to N-(N-(3,5-dichlorobenzenesulfonyl)-azetidine-2(S)-carbonyl)-3(R)-amino-3-($^4$-fluoromethoxyphenyl)propionic acid (68 mg) following the procedures described in Example 121, Steps D, E and F.

500 MHz $^1$H NMR (CD$_3$OD): δ 2.28 (dt, 2H), 2.83 (ABq d, 2H), 3.81 (t, 2H), 4.51 (t, 1H), 5.32 (t, 1H), 6.84 (br d, 2H), 7.20 (br d, 2H). 50–0.56 (m, 4H), 0.64–0.68 (m, 4H), 4.50 (t, 1H), 5.73 (d, 2H. J=55 Hz), 7.06 (br d, 2H), 7.36 (br d, 2H), 7.80–7.84 (m, 3H); MS: m/e 505 (M+H)

EXAMPLE 132

N-(N-(3,5-Dichlorobenzenesulfonyl)-azetidine-2(S)-carbonyl)-3(R)-amino-3-(4-(tetrahydrofuryl-3(S)-oxy)phenyl)propionic Acid
Step A. Methyl N-tert-Butoxycarbonyl-3(R)-amino-3-(4-(tetrahydrofuryl-3(S)-oxy)phenyl)propionate.

To a solution of methyl N-tert-butoxycarbonyl-3(R)-amino-3-(4-hydroxyphenyl)propionate ester (Example 39, Step A) (0.13 g, 0.43 mmol), triphenylphosphine (0.22 g, 0.85 mmol) and 4(R)-hydroxytetrahydrofuran (75 mg, 0.85 mmol) in 1 mL of tetrahydrofuran at 0° C. was added diethyl azodicarboxylate (0.14 mL, 0.85 mmol). After stirring at 0° C. for 2 h and at room temperature for 16 h, the reaction mixture was concentrated to dryness, and the residue was purified on silica gel eluting with hexane/ethyl acetate (2:1) to give the product along with some co-eluting side-product.

500 MHz $^1$H NMR (CD$_3$OD): δ 1.40 (br s, 9H), 2.04–2.28 (m, 2H), 2.74 (ABq d, 2H), 3.62 (s, 3H), 3.82–3.96 (m, 4H), 4.94–5.02 (m, 2H), 6.85 (br d, 2H), 7.22 (br d, 2H),

Step B. N-(N-(3,5-Dichlorobenzenesulfonyl)-azetidine-2(S)-carbonyl)-3(R)-amino-3-(4-(tetrahydrofuryl-3(S)-oxy) phenyl)propionic Acid.

The title compound was prepared from methyl N-tert-butoxycarbonyl-3(R)-amino-3-(4-(3(S)-tetrahydrofuryloxy) phenyl)propionate obtained from Step A byazetidine-2(S)-carbonylfollowing the procedures described in Example 121, Steps D, E and F.

500 MHz $^1$H NMR (CD$_3$OD): δ 2.0–2,3 (m, 4H), 2.83 (ABq d, 2H), 3.78–4.00 (m, 5H), 4.51 (t, 1H), 5.00 (br t, 1H), 5.25 (br t, 1H), 6.84 (br d, 2H), 7.30 (br d, 2H), 7.80–7.84 (m, 3H). MS: m/e 543 (M+H)

EXAMPLE 133

N-(N-(3,5-Dichlorobenzenesulfonyl)-(S)-prolyl)-3 (R)-amino-3-(4-cyclopropyloxy-phenyl)propionic Acid Step A. Methyl N-tert-Butoxycarbonyl-3(R)-amino-3-(4-cyclopropyloxy-phenyl)propionate.

The title compound was obtained by cyclopropylation of methyl N-tert-butoxycarbonyl-3(R)-amino-3-(4-hydroxyphenyl)propionate (Example 39, Step A) following the procedure described in Tetrahedron Lett, 1999, 40, 2633. The product thus obtained was only ca 50% pure by NMR and was carried on to Step B.

MS: m/e 336 (M+H)

Step B. N-(N-(3,5-Dichlorobenzenesulfonyl)-(S)-prolyl)-3 (R)-amino-3-(4-cyclopropyloxyphenyl)propionic Acid.

The material containing methyl N-tert-butoxycarbonyl-3 (R)-amino-3-(4-cyclopropyloxyphenyl)propionate obtained at Step A was converted to methyl N-(N-(3,5-dichlorobenzenesulfonyl)-(S)-prolyl)-3(R)-amino-3-(4-cyclopropyloxy-phenyl)propionate following the procedure described in Example 123, Step D and E. The product was purified to >90% by silica gel chromatography and was hydrolyzed to the title compound following the procedure of Example 121, Step F.

500 MHz $^1$H NMR (CD$_3$OD): δ 0.6–0.8 (m, 4H), 1.8–2.0 (m, 2H), 2.90 (d, 2H), 3.45–3.55 (m, 2H), 3.68 (m, 1H), 4.22 (m, 1H), 5.26 (td, 1H), 7.02 (br d, 2H), 7.30 (br d, 2H), 7.75–7.80 (m, 3H). MS: m/e 527 (M+H)

The following examples were prepared by the procedures described in Example 121, Steps E and F. The requisite aminopropionate hydrochloride salts were synthesized by the procedure of Tang and Ellman (J. Org. Chem. 1999, 64, 12). The aldehyde or ketone starting materials were purchased from commercial sources except in Example 138, in which 6-methoxypyridine-3-carboxaldehyde was prepared following literature procedure (Comins, D L et al. J. Org. Chem. 1990, 55, 69).

| Ex No | Name | MS* |
|---|---|---|
| (134) | N-(N-(3,5-Dichlorobenzenesulfonyl)-azetidine-2(S)-carbonyl)-3(R)-amino-3-(4-difluoromethoxyphenyl)-propionic acid | 523 (M + 1) |
| (135) | N-(N-(3,5-Dichlorobenzenesulfonyl)-azetidine-2(S)-carbonyl)-3(R)-amino-3-(4-methoxyphenyl)-3-methyl-propionic acid | 501 (M + 1) |
| (136) | N-(N-(3,5-Dichlorobenzenesulfonyl)-(S)-prolyl)-3(R)-amino-3-(4-methoxyphenyl)-3-methylpropionic acid | 515 (M + 1) |
| (137) | N-(N-(3,5-dichlorobenzenesulfonyl)-2(S)-prolyl)-amino-6-methoxyindane-1(R)-acetic acid | 513 (M + 1) |
| (138) | N-(N-(3,5-Dichlorobenzenesulfonyl)-azetidine-2(S)-carbonyl)-3(R)-amino-3-(6-methoxypyridin-3-yl)-propionic acid | 488 (M + 1) |

*m/e: (M + 1 (H$^+$))$^+$ or (M + 18 (NH$_4^+$))$^+$

EXAMPLE 139

N-(N-(3,5-Dichlorobenzenesulfonyl)-azetidine-2(S)-carbonyl)-3(R)-amino-3-(6-diallylaminopyridin-3-yl) propionic Acid Step A. 3-Bromo-6-diallylaminopyridine.

To a mixture of 2-amino-5-bromopyridine (5.0 g, 29 mmol), and diisopropylethylamine (12 mL, 70 mmol) in 50 mL of acetonitrile at room temperature was added allyl bromide (6.3 mL, 72 mmol), and the mixture was heated to 50° C. for 2 h. After addition of another 2.5 mL of allyl bromide and another 5 h at 50° C., the reaction mixture was concentrated to dryness with silica gel. The solid residue was purified on silica gel to give 1.6 g of the title compound (22%).

Step B. N-(N-(3,5-Dichlorobenzenesulfonyl)-azetidine-2 (S)-carbonyl)-3(R)-amino-3-(6-diallylaminopyridin-3-yl) propionic Acid.

The bromopyridine obtained from Step A was converted to the corresponding aldehyde and subsequently to the title compound following the procedures of Tang and Ellman (J. Org. Chem. 1999, 64, 12) and Example 121.

500 MHz $^1$H NMR (CD$_3$OD): δ 2.29 (td, 2H), 2.78 (ABq d, 2H), 3.80 (t, 2H), 4.09 (d, 4H), 4.50 (t, 1H), 5.10–5.16 (m, 4H), 5.20 (br t, 1H), 5.80–5.90 (m, 2H), 6.59 '(d, 1H), 7.54 (d d, H), 7.80–7.84 (m, 3H), 8.05 (d, 1H). MS: m/e 553 (M+H)

EXAMPLE 140

N-(N-(3,5-Dichlorobenzenesulfonyl)-(S)-prolyl)-3 (R)-amino-3-(3-benzyl-1,2,4-oxadiazol-5-yl) propionic Acid Step A. tert-Butyl N-(N-(3,5-Dichlorobenzenesulfonyl)-(S)-prolyl)-3(R)-amino-3-methoxycarbonylpropionate.

(D)-Aspartic acid, α-methyl ester, β-tert-butyl ester (Gazz. Chim. Ital. 1964, 94, 695) was condensed with N-(3,5-dichlorobenzenesulfonyl)-(L)-proline following the procedure of Example 121, Step E to give the title compound (1.1 g, 90%).

300 MHz $^1$H NMR (CD$_3$OD): δ 1.45 (s, 9H), 1.7–2.0 (m, 4H), 2.81 (ABq d, 2H), 3.25–3.35 (m, 1H), 3.5–3.6 (m, 1H), 3.74 (t, 3H), 4.15–4.25 (m, 1H), 4.89 (br t, 1H), 7.80–7.85 (m, 3H).

Step B. tert-Butyl N-(N-(3,5-Dichlorobenzenesulfonyl)-(S)-prolyl)-3(R)-amino-3-hydroxycarbonylpropioniate.

tert-Butyl N-(N-(3,5-dichlorobenzenesulfonyl)-(S)-prolyl)-3(R)-amino-3-methoxycarbonylpropionate obtained at Step A was hydrolyzed with lithium hydroxide in acetonitrile and water (2:1) (Example 120, Step B) to give the title compound (2.0 g, 100%).

300 MHz $^1$H NMR (CD$_3$OD): δ 1.47 (s, 9H), 1.7–2.1 (m, 4H), 2.81 (ABq d, 2H), 3.25–3.35 (m, 1H), 3.55–3.65 (m, 1H), 4.15–4.25 (m, 1H), 4.75 (br t, 1H), 7.78–7.86 (m, 3H).

Step C. tert-Butyl N-(N-(3,5-Dichlorobenzenesulfonyl)-(S)-prolyl)-3(R)-amino-3-(3-benzyl-1,2,4-oxadiazol-5-yl) propionate.

To a solution of tert-butyl N-(N-(3,5-dichlorobenzenesulfonyl)-(S)-prolyl)-3(R)-amino-3-hydroxycarbonylpropionate (0.5 g, 1.0 mmol) and benzylamidoxime (0.15 g, 1.1 mmol) in methylene chloride (5 mL) was added 1-[3-(dimethylamino)propyl]-3-ethylcarbodiimide hydrochloride (EDC, 0.19 g, 1.0 mmol), and the reaction was stirred at room temperature for 3 h. After additions of two more portions of EDC (total, 0.3 g) and another 9 h at room temperature, the reaction mixture was concentrated to dryness. The residue was dissolved in 5 mL of dioxane was treated with 0.2 g of EDC. The mixture was heated at 100° C. for 2 h, and was concentrated to dryness. The residue was purified on silica gel to give 23 mg of the title compound.

300 MHz $^1$H NMR (CD$_3$OD): δ 1.47 (s, 9H), 1.7–2.1 (m, 4H), 2.98 (ABq d, 2H), 3.25–3.35 (m, 1H), 3.48–3.62 (m, 1H), 4.05 (s, 2H), 4.12–4.22 (m, 1H), 5.02 (br t, 1H), 7.15–7.32 (m, 4H), 7.75–7.85 (m, 4H). MS: m/e 553 (M+1−56)

The following examples were prepared by the procedures described in Example 140 with the following modification: in Step C, dioxane and EDC was replaced with acetic acid, and the reaction was heated at 125° C. for 2 h. Under these conditions, the chiral center next to oxadiazole was racemized.

| Ex No | Name | MS* |
|---|---|---|
| (141) | N-(N-(3,5-Dichlorobenzenesulfonyl)-(S)-prolyl)-3(R)-amino-3-(3-(2'-fluorobenzyl)-1,2,4-oxadiazol-5-yl)-propionic acid | 571 (M + 1) |
| (142) | N-(N-(3,5-Dichlorobenzenesulfonyl)-(S)-prolyl)-3(R)-amino-3-(3-(2'-methoxybenzyl)-1,2,4-oxadiazol-5-yl)-propionic acid | 583 (M + 1) |

EXAMPLE 143 AND EXAMPLE 144

N-(3,5-Dichlorobenzenesulfonyl)-2(R) or 2(S)-methylazetidine-2-carbonyl-(3R)-amino-3-(4-(2',6'-dimethoxyphenyl)phenyl)-propionic Acid and N-(3, 5-dichloro-benzenesulfonyl)-2(S) or 2(R)-methylazetidine-2-carbonyl-(3R)-amino-3-(4-(2', 6'-dimethoxyphenyl)phenyl)-propionic Acid Step A. N-(tert-butyloxycarbonyl)-2(R,S)-methylazetidine-2-carboxylic Acid To a suspension of azetidine-2(S)-carboxylic acid (19.8 mmol, 2.0 g) in methanol (120 mL) at 0° C. was added thionyl chloride (4.0 equiv; 79.2 mmol, 9.43 g, 5.8 mL) dropwise. Dissolution was observed during the addition and the reaction mixture was stirred at ambient temperature overnight (20 h). After this time, solvent was evaporated and the oily residue was azeotroped with toluene and placed under high vacuum to give rise to azetidine-2(S)-carboxylic acid, methyl ester hydrochloride salt as an off-white solid (2.9 g, 96% yield).

$^1$H NMR (400 MHz, CDCl$_3$): δ 9.65 (brs, 1H), 5.20 (br, 1H), 4.20 (m, 2H), 3.85 (s, 3H), 2.75 (m, 2H)

To a solution of azetidine-2(S)-carboxylic acid, methyl ester hydrochloride salt (6.6 mmol, 1.0 g) in anhydrous dichloromethane (14 mL) was added di-tert-butyl dicarbonate (1.05 equiv; 6.9 mmol, 1.51 g), triethylamine (3.0 equiv; 19.8 mmol, 2.0 g, 2.76 mL), and 4-dimethyl-aminopyridine in that order at 25° C. Evolution of gas was observed almost immediately and the reaction mixture became cloudy. After stirring overnight (15 h) it was diluted with ethyl acetate and washed with 1N hydrochloric acid, saturated bicarbonate solution, and brine. Drying (MgSO$_4$), filtration, and concentration afforded N-(tert-butyloxycarbonyl)-azetidine-2(S)-carboxylic acid, methyl ester as a pale yellow oil (1.24 g, 87% yield) of satisfactory purity.

$^1$H NMR (400 MHz, CDCl$_3$): δ 4.63 (dd, 1H, J=9.2, 5.2 Hz), 4.05 (m, 1H), 3.89 (m, 1H), 3.79 (s, 3H), 2.51 (m, 1H), 2.18 (m, 1H), 1.43 (s, 9H).

To a solution of diisopropylamine (1.05 equiv; 5.9 mmol, 0.6 g, 0.83 mL) in anhydrous tetrahydrofuran (15 mL) was added n-butyl lithium (1.05 equiv; 5.9 mmol, 2.36 mL of a 2.5M solution in hexanes) and the resulting light yellow solution was warmed to 0° C. for 10 min. It was then cooled back to −78° C. and N-(tert-butoxycarbonyl)-azetidine-2(S)-carboxylic acid, methyl ester (5.63 mmol, 1.21 g) in dry tetrahydrofuran (3.0 mL) was added dropwise and stirring was continued for 45 min. After this time, hexamethylphosphoramide (2.0 equiv; 11.3 mmol, 2.02 g, 1.96 mL) was added and the reaction mixture was stirred for 0.5 h. At this point, iodomethane (5.0 equiv; 28.2 mmol, 3.99 g, 1.75 mL) was added (−78° C.), the cooling bath was removed, and stirring was continued overnight (16 h) at ambient temperature. Addition of saturated ammonium chloride solution, extraction with ethyl acetate, washing of the combined organic layer with water (2×) and brine, drying (MgSO$_4$), and concentration yielded crude material which was purified by Biotage flash-coloumn chromatography (15% ethyl acetate, 85% hexanes) to provide N-(tert-butyloxycarbonyl)-2(R,S)-methylazetidine-2-carboxylic acid, methyl ester (0.9 g, 70% yield).

$^1$H NMR (400 MHz, CDCl$_3$): δ 4.95 (m, 1H), 3.80 (m, 1H), 3.78 (s, 3H), 2.35 (m, 1H), 2.18 (m, 1H), 1.69 (s, 3H; one rotamer), 1.63 (s, 3H; other rotamer), 1.46 (s, 9H; one rotamer), 1.42 (s, 9H; other rotamer)

Step B. N-(3,5-Dichlorobenzenesulfonyl)-2(R,S)-methylazetidine-2-carboxylic Acid N-(tert-butoxycarbonyl)-2(R,S)-methylazetidine-2-carboxylic acid, methyl ester (3.7 mmol, 0.85 g) was dissolved in 1M hydrochloric acid in ethyl acetate (5.0 equiv; 18.6 mmol, 18.6 mL) and the reaction mixture was stirred overnight at ambient temperature. After this time (16 h), the solvent was evaporated carefully to furnish an off-white solid (0.61 g, 100% yield) part of which (2.42 mmol, 0.4 g) was taken in a mixture of dichloromethane (5 mL) and tetrahydrofuran (5 mL) and treated with diisopropylethylamine (3.0 equiv; 7.25 mmol, 0.94 g, 1.26 mL), 3,5-dichlorobenzenesulfonyl chloride (1.05 equiv; 2.54 mmol, 0.63 g), and 4-dimethylaminopyridine in that order at ambient temperature. The resulting solution was stirred overnight (17 h), solvents were removed under reduced pressure, and the residue was purified by Biotage flash-coloumn chromatography (15% ethyl acetate, 85% hexanes) to afford N-(3, 5-dichlorobenzenesulfonyl)-2(R,S)-methylazetidine-2-carboxylic acid (0.71 g, 87% yield).

$^1$H NMR (500 MHz, CDCl$_3$): δ 7.74 (d, 2H, J=1.5 Hz), 7.56 (t, 1H, J=1.5 Hz), 4.01 (m, 1H), 3.94 (m, 1H), 3.73 (s, 3H), 2.52 (m, 1H), 2.21 (m, 1H), 1.82 (s, 3H).

To a solution of N-(3,5-dichlorobenzenesulfonyl)-(2RS)-methyl-azetidine-2-carboxylic acid, methyl ester (2.07 mmol, 0.7 g) in methanol (12 mL) was added 1M sodium hydroxide (3.0 equiv; 6.2 mmol, 6.2 mL) and the resulting solution was stirred at ambient temperature overnight (14 h). Acidification with 1N hydrochloric acid (pH~1), extraction with ethyl acetate (2×), washing of the combined organic layer with brine, drying (MgSO$_4$), filtration, and evaporation yielded the title compound (0.65 g, 97%) as an off-white solid upon exposure to high vacuum.

$^1$H NMR (500 MHz, CD$_3$OD): δ 7.76 (d, 2H, J=2.0 Hz), 7.72 (t, 1H, J=2.0 Hz), 3.97 (m, 1H), 3.90 (m, 1H), 2.48 (m, 1H), 2.22 (m, 1H), 1.73 (s, 3H).

Step C. N-(tert-Butoxycarbonyl)-3(R)-amino-3-(4-trifluoromethylsulfonyl-oxyphenyl)-propionic Acid, Methyl Ester (3R)-amino-3-(4-hydroxphenyl)propionic acid, methyl ester, acetic cid salt (Example 28, Step D) was converted to N-tert-butoxycarbonyl-3(R)-amino-3-(4-hydroxyphenyl) propionic acid, methyl ester employing di-tert-butyl dicarbonate and triethylamine (CAUTION: 4-dimethylaminopyridine proved detrimental to this conversion) in dichloromethane/dimethylformamide (4:1). In turn, N-tert-butoxy-carbonyl-3(R)-amino-3-(4-hydroxyphenyl)propionic acid, methyl ester was transformed to the title compound using N-phenyltrifluoromethanesulfonimide and triethylamine in dichloromethane.

Step D. N-(tert-Butoxycarbonyl)-3(R)-amino-3-(4-(2',6'-dimethoxyphenyl)phenyl)-propionic Acid, Methyl Ester Coupling of N-(tert-Butoxycarbonyl)-3(R)-amino-3-(4-trifluoro-methylsulfonyloxyphenyl)propionic acid, methyl ester (1.81 mmol, 775 mg) with 2,6-dimethoxyphenylboronic acid (1.3 equiv; 2.36 mmol, 429 mg) was conducted as described in Examples 22 and 23, Step D with the exception of using 2M potassium carbonate solution (3.0 equiv; 5.44 mmol, 2.7 mL) instead of solid material. This way, the title compound was obtained (691 mg) in 92% yield after purification (Biotage flash-coloumn chromatography; 20% ethyl acetate, 80% hexanes).

$^{1}$H NMR (500 MHz, CDCl$_{3}$): δ 7.34 (s, 4H), 7.28 (t, 1H, J=8.5 Hz), 6.66 (d, 1H, J=8.5 Hz), 5.38 (brs, 1H), 5.21 (brs, 1H), 3.74 (s, 6H), 3.68 (s, 3H), 2.91 (m, 2H), 1.4 (s, 9H).

Step E. N-(3,5-Dichlorobenzenesulfonyl)-2(R) or 2(S)-methylazetidine-2-carbonyl-3(R)-amino-3-(4-(2',6'-dimethoxyphenyl)phenyl)-propionic Acid, Methyl Ester and N-(3,5-Dichlorobenzenesulfonyl)-2(S) or 2-(R)-methyl-azetidine-2-carbonyl-(3R)-amino-3-(4-(2',6'-dimethoxyphenyl)phenyl)-propionic Acid, Methyl Ester Deprotection of N-(tert-Butoxycarbonyl)-3(R)-amino-3-(4-(2',6'-dimethoxyphenyl)phenyl)propionic acid, methyl ester (1.66 mmol, 0.69 g) was carried out as described previously (Examples 13, Step E) with anhydrous HCl in ethyl acetate to furnish the corresponding hydrochloride salt (0.51 g, 88% yield). The latter was coupled with N-(3,5-dichlorobenzenesulfonyl)-2(R,S)-methylazetidine-2-carboxylic acid (1.05 equiv; 1.51 mmol, 0.49 g) in dichloromethane/tetrahydrofuran (1:1) as described in Example 13, Step D to provide a mixture of the title diastereomeric compounds (0.85 g, 91% yield) which were separated by Biotage flash-coloumn chromatography (35% ethyl acetate, 65% hexanes): less polar diastereomer (0.39 g).

$^{1}$H NMR (400 MHz, CDCl$_{3}$): δ 8.05 (d, 1H, J=8.4 Hz), 7.81 (d, 2H, J=2.0 Hz), 7.61 (t, 1H, J=2.0 Hz), 7.39 (s, 4H), 7.29 (t, 1H, J=8.5 Hz), 6.67 (d, 2H, J=8.5 Hz), 5.52 (m, 1H), 3.92 (m, 1H), 3.75 (s, 6H), 3.71 (s, 3H), 3.66 (m, 1H), 2.97 (m, 2H), 2.66 (m, 1H), 2.10 (m, 1H), 1.78 (s, 3H). more polar diastereomer (0.46 g).

$^{1}$H NMR (400 MHz, CDCl$_{3}$): δ 8.23 (d, 1H, J=8.4 Hz), 7.89 (d, 2H, J=2.0 Hz), 7.62 (t, 1H, J=2.0 Hz), 7.40 (d, 2H, J=8.4 Hz), 7.37 (d, 2H, J=8.4 Hz), 7.28 (t, 1H, J=8.5 Hz), 6.66 (d, 2H, J=8.5 Hz), 5.55 (m, 1H), 3.94 (m, 1H), 3.74 (s, 6H), 3.71 (s, 3H), 3.65 (m, 1H), 2.98 (d, 2H, J=6.0 Hz), 2.72 (m, 1H), 2.14 (m, 1H), 1.80 (s, 3H).

Step F. N-(3,5-Dichlorobenzenesulfonyl)-2(R) or 2(S)-methylazetidine-2-carbonyl-3(R)-amino-3-(4-(2',6'-dimethoxyphenyl)phenyl)-propionic Acid and N-(3,5-Dichlorobenzenesulfonyl)-2(S) or 2(R)-methyl-azetidine-2-carbonyl-3(R)-amino-3-(4-(2',6'-dimethoxyphenyl)phenyl)-propionic Acid.

Hydrolysis of the two diastereomers obtained in Step E was accomplished as described in Example 13, Step E to give the title compounds in quantitative yield: less polar diastereomer:

MS: m/e 607 (M+H), 629 (M+Na).

$^{1}$H NMR (500 MHz, CDCl$_{3}$): δ 8.00 (d, 1H, J=9.0 Hz), 7.76 (d, 2H, J=1.5 Hz), 7.60 (t, 1H, J=1.5 Hz), 7.42 (d, 2H, J=8.5 Hz), 7.39 (d, 2H, J=8.5 Hz), 7.30 (t, 1H, =8.5 Hz), 6.67 (d, 2H, J=8.5 Hz), 5.53 (m, 1H), 3.89 (m, 1H), 3.74 (s, 6H), 3.69 (m, 1H), 2.98 (m, 2H), 2.67 (m, 1H), 2.08 (m, 1H), 1.73 (s, 3H) more polar diastereomer:

MS: m/e 607 (M+H), 629 (M+Na). $^{1}$H NMR (500 MHz, CDCl$_{3}$): δ 8.07 (d, 1H, J=9.0 Hz), 7.79 (d, 2H, J=1.5 Hz), 7.60 (t, 1H, J=1.5 Hz), 7.41 (d, 2H, J=8.0 Hz), 7.38 (d, 2H, J=8.0 Hz), 7.28 (t, 1H, J=8.5 Hz), 6.66 (d, 2H, J=8.5 Hz), 5.56 (m, 1H), 3.88 (m, 1H), 3.74 (s, 6H), 3.70 (m, 1H), 3.01 (m, 2H), 2.69 (m, 1H), 2.09 (m, 1H), 1.72 (s, 3H)

EXAMPLE 145 AND EXAMPLE 146

N-(3,5-Dichlorobenzenesulfonyl)-2(R) or 2(S)-methylazetidine-2-carbonyl-3(R)-amino-3-(4-methoxyphenyl)-propionic acid and N-(3,5-dichlorobenzenesulfonyl)-2(S) or 2(R)-methylazetidine-2-carbonyl-3(R)-amino-3-(4-methoxyphenyl)-propionic Acid Step A. N-(tert-Butoxycarbonyl)-(3R)-amino-3-(4-methoxyphenyl)-propionic Acid, Methyl Ester To a solution of N-tert-butoxycarbonyl-3(R)-amino-3-(4-hydroxy-phenyl)propionic acid, methyl ester (1.69 mmol, 0.5 g) in acetone (7.0 mL) was added potassium carbonate (5.0 equiv; 8.46 mmol, 1.17 g) and iodomethane (10.0 equiv; 16.9 mmol, 2.4 g, 1.05 mL). The resulting suspension was heated at reflux temperature for 4.5 h. After this time, additional quantities of potassium carbonate (2.5 equiv; 4.23 mmol, 0.59 g) and iodomethane (5.0 equiv; 8.45 mmol, 1.2 g, 0.53 mL) were added and heating was continued for 5.0 h. Water was added and the reaction mixture was extracted with ethyl acetate (2×). The combined organic layer was washed with brine, dried (MgSO$_{4}$), filtered, and evaporated to afford a pale yellow oil which solidified (514 mg, 98% yield) upon exposure to high vacuum and proved to be of satisfactory purity (514 mg, 98% yield).

$^{1}$H NMR (400 MHz, CDCl$_{3}$): δ 7.23 (brd, 2H), 6.87 (brd, 2H), 5.39 (brs, 1H), 5.05 (brs, 1H), 3.80 (s, 3H), 3.63 (s, 3H), 2.83 (m, 2H), 1.44 (s, 9H).

Step B. N-(3,5-Dichlorobenzenesulfonyl)-2(R) or 2(S)-methylazetidine-2-carbonyl-3(R)-amino-3-(4-methoxyphenyl)-propionic Acid, Methyl Ester and N-(3,5-dichlorobenzenesulfonyl)-2(S) or 2(R)-methylazetidine-2-carbonyl-3(R)-amino-3-(4-methoxyphenyl)-propionic Acid, Methyl Ester Deprotection of N-tert-butoxycarbonyl-3(R)-amino-3-(4-methoxyphenyl)-propionic acid, methyl ester (1.65 mmol, 0.51 g) was carried out as described previously (Example 13, Step E) with anhydrous HCl in ethyl acetate to furnish the corresponding hydrochloride salt (0.4 g, 98% yield). The latter (1.05 equiv; 0.525 mmol, 129 mg) was coupled with N-(3,5-Dichlorobenzenesulfonyl)-2(R,S)-methylazetidine-2-carboxylic acid (1.0 equiv; 0.5 mmol, 162 mg) in dichloromethane/tetrahydrofuran (1:1) as described in Example 13, Step D to provide a mixture of the title diastereomeric compounds (0.23 g, 95% yield) which were separated by Biotage flash-coloumn chromatography (35% ethyl acetate, 65% hexanes): less polar diastereomer (0.12 g);

$^{1}$H NMR (500 MHz, CDCl$_{3}$): δ 7.96 (d, 1H, J=8.5 Hz), 7.73 (d, 2H, J=1.5 Hz) 7.61 (t, 1H, J=1.5 Hz), 7.31 (m, 2H), 6.92 (m, 2H), 5.37 (m, 1H), 3.90 (m, 1H), 3.82 (s, 3H), 3.67 (s, 3H), 3.58 (m, 1H), 2.96 (dd, 1H, J=15.5, 6.5 Hz), 2.87 (dd, 1H, J=15.5, 6.5 Hz), 2.66 (m, 1H), 2.06 (m, 1H), 1.79 (s, 3H). more polar diastereomer (0.1.1 g);

$^{1}$H NMR (500 MHz, CDCl$_{3}$): δ 8.17 (d, 1H, J=8.5 Hz), 7.86 (d, 2H, J=2.0 Hz), 7.62 (t, 1H, J=2.0 Hz), 7.30 (m, 2H), 6.91 (m, 2H), 5.40 (m, 1H), 3.93 (m, 1H), 3.82 (s, 3H), 3.68 (s, 3H), 3.64 (m, 1H), 2.94 (dd, 1H, J=15.5, 6.0 Hz), 2.89 (dd, 1H, J=15.5, 5.5 Hz), 2.67 (m, 1H), 2.13 (m, 1H), 1.76 (s, 3H).

Step C. N-(3,5-Dichlorobenzenesulfonyl)-2(R) or 2(S)-methylazetidine-2-carbonyl-3(R)-amino-3-(4-methoxyphenyl)-propionic Acid and N-(3,5-dichlorobenzenesulfonyl)-2(S) or 2(R)-methylazetidine-2-carbonyl-3(R)-amino-3-(4-methoxyphenyl)-propionic Acid Hydrolysis of the two diastereomers obtained in Step B was accomplished as described in Example 13, Step E to give the title compounds in quantitative yield: less polar diastereomer:

MS: m/e 501 (M+H), 523 (M+Na).

$^{1}$H NMR (500 MHz, CDCl$_{3}$): δ 7.89 (d, 1H, J=8.5 Hz), 7.66 (d, 2H, J=2.0 Hz), 7.60 (t, 1H, J=2.0 Hz), 7.32 (m, 2H), 6.92 (m, 2H), 5.37 (m, 1H), 3.87 (m, 1H), 3.81 (s, 3H), 3.58 (m, 1H), 3.00 (dd, 1H, J=16.0, 7.0 Hz), 2.89 (dd, 1H, J=16.0, 6.5 Hz), 2.65 (m, 1H), 2.05 (m, 1H), 1.73 (s, 3H). more polar diastereomer:

MS: m/e 501 (M+H), 523 (M+Na).

$^1$H NMR (500 MHz, CDCl$_3$): δ 7.98 (d, 1H, J=8.5 Hz), 7.75 (d, 2H, J=1.5 Hz), 7.60 (t, 1H, J=1.5 Hz), 7.30 (m, 2H), 6.91 (m, 2H), 5.39 (m, 1H), 3.87 (m, 1H), 3.81 (s, 3H), 3.69 (m, 1H), 2.97 (dd, 1H, J=15.5, 6.5 Hz), 2.91 (dd, 1H, J=15.5, 6.0Hz), 2.63 (m, 1H), 2.07 (m, 1H), 1.66 (s, 3H).

EXAMPLE 147

N-(3,5-Dichlorobenzenesulfonyl)-(S)-prolyl-3(R)-amino-3-(4-(5 '-tert-butyl-2'-thiazolyl)phenyl)-propionic Acid Step A. (SR)-N-(tert-butanesulfinyl)-3(R)-amino-3-(4-(5'-tert-butyl-2'-thiazolyl)phenyl)-propionic Acid A solution of diisopropylamine (1.25 equiv; 2.87 mmol, 0.29 g, 0.4 mL) in anhydrous tetrahydrofuran (4.0 mL) was cooled to –50° C., n-butyllithium (1.3 equiv; 2.99 mmol, 1.2 mL of a 2.5M solution in hexanes) was added dropwise, and the resulting light yellow solution was warmed to 0° C. for 10 min. It was then cooled back to –78° C. and methyl acetate (1.2 equiv; 2.76 mmol, 0.2 g, 0.22 mL) was added dropwise via syringe while stirring was continued for 30 min. After this time, chlorotitanium triisopropoxide (2.6 equiv; 5.98 mmol, 1.56 g, 1.43 mL) dissolved in tetrahydrofuran (1.5 mL) was added dropwise at –78° C. to form a yellow titanium enolate which was stirred at –78° C. for 45 min. At this point, the sulfinyl imine (resulting from condensation of (SR)-tert-butanesulfinamide with 4-(5'-tert-butyl-2'-thiazolyl)-benzaldehyde according to Tang and Ellman in *J. Org. Chem.* 1999, 64, 12; 2.3 mmol, 0.8 g) in tertahydrofuran (1.5 mL) was added dropwise and the reaction mixture was stirred at –78° C. for 5 h. A saturated solution of ammonium chloride was added, the cooling bath was removed, and the insoluble titanium salts formed were dissolved upon addition of 1N hydrochloric acid at ambient temperature. Extraction with ethyl acetate (2×), washing of the combined organic layer with saturated sodium bicarbonate and brine, drying (MgSO$_4$), filtration, and concentration provided a yellow-orange oil which was purified by Biotage flash-coloumn chromatography to give the title compound (0.72 g, 74% yield) as an off-white solid. $^1$H NMR (500 MHz, CDCl$_3$): δ 7.95 (m, 2H), 7.40 (m, 2H), 6.9 (s, 1H), 4.84 (m, 1H), 4.71 (d, 1H, J=4.5), 3.69 (s, 3H), 2.91 (m, 2H), 1.40 (s, 9H), 1.25 (s, 9H).

Step B. N-(3,5-Dichlorobenzenesulfonyl)-(S)-prolyl-(3R)-amino-3-(4-(5'-tert-butyl-2'-thiazolyl)phenyl)-propionic Acid, Methyl Ester (S$_R$)-N-(tert-butanesulfinyl)-3(R)-amino-3-(4-(5'-tert-butyl-2'-thiazolyl)phenyl)-propionic acid (0.5 mmol, 211 mg) was dissolved in methanol (2.5 mL) and treated with 1M hydrochloric acid in ethyl acetate (5.0 equiv; 2.5 mmol, 2.5 mL). The resulting solution was stirred at ambient temperature for 0.5 h after which time solvents were evaporated carefully to furnish the corresponding hydrochloride salt (0.17 g, 96% yield) as a pale yellow solid. The latter (0.35 mmol, 124 mg) was coupled with N-(3,5-Dichlorobenzenesulfonyl)-(S)-proline (1.1 equiv; 0.385 mmol, 125 mg) in dichloromethane/tetrahydrofuran (1:1) as described in Example 13, Step D to provide the title compound (165 mg, 69% yield) after purification by Biotage flash-coloumn chromatography (35% ethyl acetate, 65% hexanes).

$^1$H NMR (500 MHz, CDCl$_3$): δ 7.94 (m, 2H), 7.87 (d, 1H, J=8.5 Hz), 7.76 (d, 2J=1.5 Hz), 7.64 (t, 1H, J=1.5 Hz), 7.37 (m, 2H), 6.90 (s, 1H), 5.45 (m, 1H), 4.18 (m, 1H), 3.69 (s, 3H), 3.65 (m, 1H), 3.22 (m, 1H), 3.02 (dd, 1H, J=16.0, 5.5 Hz), 2.94 (dd, 1H, J=16.0, 6.0 Hz), 2.21 (m, 1H), 1.79 (m, 3H), 1.40 (s, 9H).

Step C. N-(3,5-Dichlorobenzenesulfonyl)-(S)-prolyl-(3R)-amino-3-(4-(5'-tert-butyl-2'-thiazolyl)phenyl)-propionic Acid Hydrolysis of N-(3,5-Dichlorobenzenesulfonyl)-(S)-prolyl-3(R)-amino-3-(4-(5'-tert-butyl-2'-thiazolyl)phenyl)-propionic acid, methyl ester obtained in Step B was accomplished as described in Example 13, Step E to give the title compound in quantitative yield.

MS: m/e 610 (M+H);

$^1$H NMR (500 MHz, CDCl$_3$): 7.92 (m, 2H), 7.85 (d, 1H, J=8.5 Hz), 7.73 (d, 2H, J=1.5 Hz), 7.61 (t, 1H, J=1.5 Hz), 7.38 (m, 2H), 6.89 (s, 1H), 5.46 (m, 1H), 4.18 (m, 1H), 3.62 (m, 1H), 3.18 (m, 1H), 3.07 (dd, 1H, J=16.0, 5.5 Hz), 2.98 (dd, 1H, J=16.0, 6.5 Hz), 2.19 (m, 1H), 1.76 (m, 3H), 1.40 (s, 9H). $^{13}$C NMR (125 MHz, CDCl$_3$): δ 174.60, 170.36, 167.70, 166.26, 141.53, 138.83, 136.42, 133.65, 133.39, 126.99, 126.71, 126.04, 110.37, 62.60, 49.96, 49.46, 39.21, 34.94, 30.47, 30.06, 24.53.

EXAMPLE 148

Inhibition of VLA-4 Dependent Adhesion to BSA-CS-1 Conjugate

Step A. Preparation of CS-1 Coated Plates.

Untreated 96 well polystyrene flat bottom plates were coated with bovine serum albumin (BSA; 20 μg/ml) for 2 hours at room temperature and washed twice with phosphate buffered saline (PBS). The albumin coating was next derivatized with 10 μg/ml 3-(2-pyridyldithio) propionic acid N-hydroxysuccinimide ester (SPDP), a heterobifunctional crosslinker, for 30 minutes at room temperature and washed twice with PBS. The CS-1 peptide (Cys-Leu-His-Gly-Pro-Glu-Ile-Leu-Asp-Val-Pro-Ser-Thr SEQ ID no. 1), which was synthesized by conventional solid phase chemistry and purified by reverse phase HPLC, was next added to the derivatized BSA at a concentration of 2.5 μg/ml and allowed to react for 2 hours at room temperature. The plates were washed twice with PBS and stored at 4° C.

Step B. Preparation of Fluorescently Labeled Jurkat Cells.

Jurkat cells, clone E6-1, obtained from the American Type Culture Collection (Rockville, Md.; cat # ATCC TIB-152) were grown and maintained in RPMI-1640 culture medium containing 10% fetal calf serum (FCS), 50 units/ml penicillin, 50 μg/ml streptomycin and 2 mM glutamine. Fluorescence activated cell sorter analysis with specific monoclonal antibodies confirmed that the cells expressed both the α4 and β1 chains of VLA-4. The cells were centrifuged at 400×g for five minutes and washed twice with PBS. The cells were incubated at a concentration of 26×10$^6$ cells/ml in PBS containing a 1 μM concentration of a fluorogenic esterase substrate (2',7'-bis-(2-carboxyethyl)-5-(and -6)-carboxyfluorescein, acetoxymethyl ester; BCECF-AM; Molecular Probes Inc., Eugene, Oregon; catalog #B-1150) for 30–60 minutes at 37° C. in a 5% CO$_2$/air incubator. The fluorescently labeled Jurkat cells were washed two times in PBS and resuspended in RPMI containing 0.25% BSA at a final concentration of 2.0×10$^6$ cells/ml.

Step C. Assay Procedure.

Compounds of this invention were prepared in DMSO at 100× the desired final assay concentration. Final concentrations were selected from a range between 0.001 nM-100 μM. Three μL of diluted compound, or vehicle alone, were premixed with 300 μL of cell suspension in 96-well polystyrene plates with round bottom wells. 100 μL aliquots of the cell/compound mixture were then transferred in duplicate to CS-1 coated wells. The cells were next incubated for 30 minutes at room temperature. The non-adherent cells were removed by two gentle washings with PBS. The remaining adherent cells were quantitated by reading the plates on a Cytofluor II fluorescence plate reader (Perseptive Biosystems Inc., Framingham, Mass.; excitation and emission filter settings were 485 nm and 530 nm, respectively). Control wells containing vehicle alone were used to determine the level of cell adhesion corresponding to 0% inhibition. Control wells coated with BSA and crosslinker (no CS-1 peptide) were used to determine the level of cell adhesion corresponding to 100% inhibition. Cell adhesion to wells coated with BSA and crosslinker was usually less than 5% of that observed to CS-1 coated wells in the presence of vehicle. Percent inhibition was then calculated for each test well and the $IC_{50}$ was determined from a ten point titration using a validated four parameter fit algorithm.

EXAMPLE 149

Antagonism of VLA-4 Dependent Binding to VCAM-Ig Fusion Protein

Step A. Preparation of VCAM-Ig.

The signal peptide as well as domains 1 and 2 of human VCAM (GenBank Accession no. M30257) were amplified by PCR using the human VCAM cDNA (R & D Systems) as template and the following primer sequences: 3'-PCR primer:5'-AATTATAATTTGATCAACTTAC CTGTCAATTCTTTTACAGCCTGCC-3'(SEQ ID NO:2) 5'-PCR primer:
5'-ATAGGAATTCCAGCTGCCACCATGCCTGGG AAGATGGTCG-3'(SEQ ID NO: 3);

The 5'-PCR primer contained EcoRI and PvuII restriction sites followed by a Kozak consensus sequence (CCACC) proximal to the initiator methionine ATG. The 3'-PCR primer contained a BclI site and a splice donor sequence. PCR was performed for 30 cycles using the following parameters: 1 min. at 94° C., 2 min. at 55° C., and 2 min. at 72° C. The amplified region encoded the following sequence of human VCAM-1:

MPGKMVVILGASNILWIMFAASQAFKI-ETTPESRYLAQIGDSVSLTCSTTGCES PFFSWRT-QIDSPLNGKVTNEGTTSTLTMNPVSF-GNEHSYLCTATCESRKLEKG IQVEIYSFPKDPEIHLSGPLEAGK-PITVKCSVADVYPFDRLEIDLLKGDHLMKS QEFLEDADRKSLETKSLEVTFT-PVIEDIGKVLVCRAKLHIDEMDSVPTVRQAV KEL. The resulting PCR product of 650 bp was digested with EcoRI and BclI and ligated to expression vector pIg-Tail (R & D Systems, Minneapolis, Minn.) digested with EcoRI and BamHI. The pIg-Tail vector contains the genomic fragment which encodes the hinge region, CH2 and CH3 of human IgGI (GenBank Accession no. Z17370). The DNA sequence of the resulting VCAM fragment was verified using Sequenase (U.S. Biochemical, Cleveland, Ohio). The fragment encoding the entire VCAM-Ig fusion was subsequently excised from pIg-Tail with EcoRI and NotI and ligated to pCI-neo (Promega, Madison, Wisc.) digested with EcoRI and NotI. The resulting vector, designated pCI-neo/VCAM-Ig was transfected into CHO-K1 (ATCC CCL 61) cells using calcium-phosphate DNA precipitation (Specialty Media, Lavalette, N.J.). Stable VCAM-Ig producing clones were selected according to standard protocols using 0.2–0.8 mg/ml active G418 (Gibco, Grand Island, N.Y.), expanded, and cell supernatants were screened for their ability to mediate Jurkat adhesion to wells previously coated with 1.5 μg/ml (total protein) goat anti-human IgG (Sigma, St. Louis, Mo.). A positive CHO-K1/NVCAM-Ig clone was subsequently adapted to CHO-SFM serum-free media (Gibco) and maintained under selection for stable expression of VCAM-Ig. VCAM-Ig was purified from crude culture supernatants by affinity chromatography on Protein A/G Sepharose (Pierce, Rockford, Ill.) according to the manufacturer's instructions and desalted into 50 mM sodium phosphate buffer, pH 7.6, by ultrafiltration on a YM-30 membrane (Amicon, Beverly, Mass.).

Step B. Preparation of $^{125}$I-VCAM-Ig.

VCAM-Ig was labeled to a specific radioactivity greater that 1000 Ci/mmole with $^{125}$I-Bolton Hunter reagent (New England Nuclear, Boston, Mass.; cat # NEX120-0142) according to the manufacturer's instructions. The labeled protein was separated from unincorporated isotope by means of a calibrated HPLC gel filtration column (G2000SW; 7.5×600 mm; Tosoh, Japan) using uv and radiometric detection.

Step C. VCAM-Ig Binding Assay.

Compounds of this invention were prepared in DMSO at 100× the desired final assay concentration. Final concentrations were selected from a range between 0.001 nM-100 μM. Jurkat cells were centrifuged at 400×g for five minutes and resuspended in binding buffer (25 mM HEPES, 150 mM NaCl, 3 mM KCl, 2 mM glucose, 0.1% bovine serum albumin, pH 7.4). The cells were centrifuged again and resuspended in binding buffer supplemented with $MnCl_2$ at a final concentration of 1 mM. Compounds were assayed in Millipore MHVB multiscreen plates (cat# MHVBN4550, Millipore Corp., Mass.) by making the following additions to duplicate wells: (i) 200 μL of binding buffer containing 1 mM $MnCl_2$; (ii) 20 μL of $^{125}$I-VCAM-Ig in binding buffer containing 1 mM $MnCl_2$ (final assay concentration ~100 pM); (iii) 2.5 μL of compound solution or DMSO; (iv) and 0.5×10$^6$ cells in a volume of 30 μL. The plates were incubated at room temperature for 30 minutes, filtered on a vacuum box, and washed on the same apparatus by the addition of 100 μL of binding buffer containing 1 mM $MnCl_2$. After insertion of the multiscreen plates into adapter plates (Packard, Meriden, Conn., cat# 6005178), 100 μL of Microscint-20 (Packard cat# 6013621) was added to each well. The plates were then sealed, placed on a shaker for 30 seconds, and counted on a Topcount microplate scintillation counter (Packard). Control wells containing DMSO alone were used to determine the level of VCAM-Ig binding corresponding to 0% inhibition. Contol wells in which cells were omitted were used to determine the level of binding corresponding to 100% inhibition. Binding of $^{125}$I-VCAM-Ig in the absence of cells was usually less than 5% of that observed using cells in the presence of vehicle. Percent inhibition was then calculated for each test well and the $IC_{50}$ was determined from a ten point titration using a validated four parameter fit algorithm.

EXAMPLE 150

Antagonism of $\alpha_4\beta_7$ Dependent Binding to VCAM-Ig Fusion Protein

Step A. $\alpha_4\beta_7$ Cell line.

RPMI-8866 cells (a human B cell line $\alpha_4^{+-}\beta_7^+$; a gift from Prof. John Wilkins, University of Manitoba, Canada) were grown in RPMI/10% fetal calf serum/100 U penicillin/

100 μg streptomycin/2 mM L-glutamine at 37° C., 5% carbon dioxide. The cells were pelleted at 1000 rpm for 5 minutes and then washed twice and resuspended in binding buffer (25 mM Hepes, 150 mM NaCl , 0.1% BSA, 3 mM KCl, 2 mM Glucose, pH 7.4).

Step B. VCAM-Ig Binding Assay.

Compounds of this invention were prepared in DMSO at 100× the desired final assay concentration. Final concentrations were selected from a range between 0.001 nM-100 μM. Compounds were assayed in Millipore MHVB multiscreen plates (Cat# MHVBN4550) by making the following sequential additions to duplicate wells: (i) 100 μl/well of binding buffer containing 1.5 mM MnCl$_2$; (ii) 10 μl/well $^{125}$I-VCAM-Ig in binding buffer (final assay concentration <500 pM); (iii) 1.5 μl/well test compound or DMSO alone; (iv) 38 μl/well RPMI-8866 cell suspension (1.25×106 cells/well). The plates were incubated at room temperature for 45 minutes on a plate shaker at 200 rpm, filtered on a vacuum box, and washed on the same apparatus by the addition of 100 μL of binding buffer containing 1mM MnCl$_2$. After insertion of the multiscreen plates into adapter plates (Packard, Meriden, Coon., cat# 6005178), 100 μL of Microscint-20 (Packard cat# 6013621) was added to each well. The plates were then sealed, placed on a shaker for 30 seconds, and counted on a Topcount microplate scintillation counter (Packard). Control wells containing DMSO alone were used to determine the level of VCAM-Ig binding corresponding to 0% inhibition. Wells in which cells were omitted were used to determine the level of binding corresponding to 100% inhibition. Percent inhibition was then calculated for each test well and the IC$_{50}$ was determined from a ten point titration using a validated four parameter fit algorithm.

What is claimed is:

1. A compound having the formula Ib:

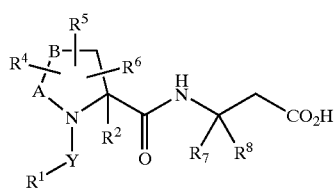

Ib wherein $R^1$ is phenyl optionally substituted with one or two groups selected from halogen, O—$C_{1-3}$alkyl, and trifluoromethyl;

$R^2$ is H or methyl;

B is O, S, a bond or $CH_2$;

A is —C—;

Y is —$SO_2$;

$R^4$, $R^5$, $R^6$ are independently selected from H, $C_{1-3}$ alkyl and halogen;

$R^7$ is hydrogen;

$R^8$ is aryl, heteroaryl, aryl-aryl, aryl-heteroaryl or heteroaryl-aryl wherein aryl and heteroaryl are optionally substituted with one to three groups selected from halogen, CN, $OR^d$, $O(CO)R^e$, $C_{1-5}$alkyl optionally substituted with one or two groups selected from $R^c$, $CF_3$, and $OC(O)NR^dR^e$;

$R^c$ is 1) halogen,
2) CN,
3) $NH(C_{1-5}alkyl)$,
4) $N(C_{1-5}alkyl)_2$,
5) amino,
6) carboxy,
7) $C_{1-4}alkyl$,
8) $C_{1-4}alkoxy$,
9) aryl,
10) aryl $C_{1-4}alkyl$, or
11) aryloxy;

$R^d$ and $R^e$ are independently selected from hydrogen, $C_{1-10}$alkyl, $C_{2-10}$alkenyl, $C_{2-10}$alkynyl, Cy and Cy–$C_{1-10}$alkyl, wherein alkyl, alkenyl, alkynyl and Cy is optionally substituted with one to four substituents independently selected from $R^c$; or $R^d$ and $R^e$ together with the atoms to which they are attached form a heterocyclic ring of 5 to 7 members containing 0–2 additional heteroatoms independently selected from oxygen, sulfur and nitrogen;

Cy is cycloalkyl, heterocyclyl, aryl or heteroaryl.

2. A compound of claim 1 having the formula Ic:

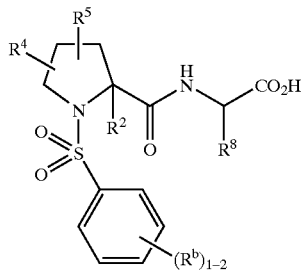

Ic wherein $R^4$ and $R^5$ are independently H, halogen or $CH_3$;

$R^8$ is aryl, aryl-aryl, heteroaryl-aryl (wherein aryl is attached to the propionic acid backbone) and wherein aryl and heteroaryl are optionally substituted with one to three groups selected from halogen, CN, $OR^d$, $O(CO)R^d$, $C_{1-5}$alkyl optionally substituted with one or two groups selected from $R^c$, $CF_3$, and $OC(O)NR^dR^e$;

$R^b$ is halogen, O-$C_{1-3}$alkyl or trifluoromethyl.

3. A compound of claim 2 wherein for $R^8$ aryl is phenyl and heteroaryl is selected from the group consisting of pyridyl, pyrimidinyl, thiazolyl and oxadiazolyl.

4. A compound of claim 1 having the formula Id:

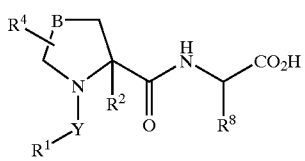

wherein

B is a bond, O or S;

Y is $SO_2$;

$R^1$ is phenyl optionally substituted with one or two groups selected from halogen, $O-C_{1-3}$alkyl, and trifluoromethyl;

$R^2$ is H or methyl;

$R^4$ is selected from H, $C_{1-3}$alkyl and halogen;

$R^8$ is aryl, heteroaryl, aryl-aryl, aryl-heteroaryl or heteroaryl-aryl wherein aryl and heteroaryl are optionally substituted with one to three groups selected from halogen, CN, $OR^d$, $O(CO)R^d$, $C_{1-5}$alkyl optionally substituted with one or two groups selected from $R^c$, $CF_3$, and $OC(O)NR^dR^e$.

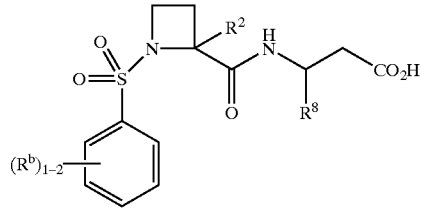

5. A compound of claim 4 having the formula Ie:

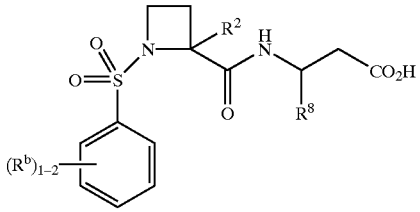

wherein $R^2$ is H or methyl;

$R^8$ is aryl, heteroaryl, aryl-aryl, aryl-heteroaryl or heteroaryl-aryl wherein aryl and heteroaryl are optionally substituted with one to three groups selected from halogen, CN, $OR^d$, $O(CO)R^d$, $C_{1-5}$alkyl optionally substituted with one or two groups selected from $R^c$, $CF_3$, and $OC(O)NR^dR^e$;

$R^b$ is halogen, $OC_{1-3}$alkyl or $CF_3$.

6. A compound of claim 4 having the formula If:

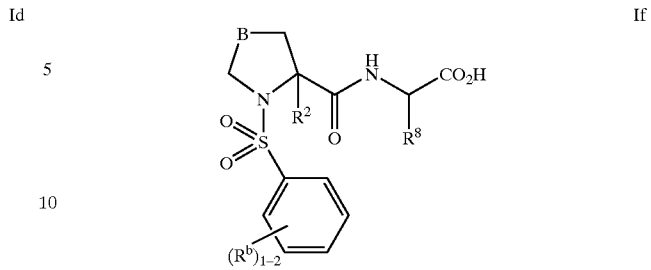

wherein

B is O or S;

$R^2$ is H or methyl; $R^8$ is aryl, heteroaryl, aryl-aryl, aryl-heteroaryl or heteroaryl-aryl wherein aryl and heteroaryl are optionally substituted with one to three groups selected from halogen, CN, $OR^d$, $O(CO)R^d$, $C_{1-5}$alkyl optionally substituted with one or two groups selected from $R^c$, $CF_3$, and $OC(O)NR^dR^e$;

$R^b$ is halogen, $OC_{1-3}$alkyl or $CF_3$.

7. A compound of claim 1 selected from the group consisting of:

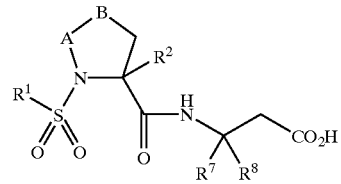

$R^7$ is hydogen unless otherwise specified,

| 2/3* | A-B | $R^1$ | $R^2$ | $R^8$ |
|---|---|---|---|---|
| S/R | $CH_2-CH_2$ | 3,5-diCl-Ph | H | phenyl |
| S/S | $CH_2-CH_2$ | 3,5-diCl-Ph | H | phenyl |
| S/R | $CH_2-CH_2$ | 3-Cl-Ph | H | phenyl |
| S/R | $CH_2-CH_2$ | 3,5-diCl-Ph | $CH_3$ | 4-F-phenyl |
| S/R | $CH_2-CH_2$ | 3,5-diCl-Ph | H | 4-fluorophenyl |
| S/S | $CH_2-CH_2$ | 3,5-diCl-Ph | H | 4-fluorophenyl |
| S/S | $CH_2-CH_2$ | 3,5-diCl-Ph | $CH_3$ | 4-F-phenyl |
| S/R | $CH_2-CH_2$ | 3,5-diCl-Ph | H | biphenyl |
| S/S | $CH_2-CH_2$ | 3,5-diCl-Ph | H | biphenyl |
| S/R | $CH_2-CH_2$ | 3,5-diCl-Ph | H | 2'-methoxybiphenyl |
| S/S | $CH_2-CH_2$ | 3,5-diCl-Ph | H | 2'-methoxybiphenyl |
| S/R | $CH_2-CH_2$ | 3,5-diCl-Ph | H | 4-hydroxyphenyl |
| S/S | $CH_2-CH_2$ | 3,5-diCl-Ph | H | 4-hydroxyphenyl |
| S/R | $CH_2-CH_2$ | 3,5-diCl-Ph | H | 4-t-butoxyphenyl |
| S/R | $CH_2-CH_2$ | 3,5-diCl-Ph | H | 2'-cyanobiphenyl |
| S/R | $CH_2-CH_2$ | 3,5-diCl-Ph | H | 2'-formylbiphenyl |
| S/R | $CH_2-CH_2$ | 3,5-diCl-Ph | H | 2'-dimethylamino-methylbiphenyl |
| S/R | $CH_2-CH_2$ | 3,5-diCl-Ph | H | 2'-hydroxymethyl-biphenyl |
| S/R | $CH_2-CH_2$ | 3,5-diCl-Ph | H | 4-(2-methyl-5-$CF_3$-benzoxazol-7-yl)-phenyl |
| S/R | $CH_2-CH_2$ | 3,5-diCl-Ph | H | 4-(pyrimidin-5-yl)-phenyl |
| S/R | $CH_2-CH_2$ | Ph | H | 2'-methoxybiphenyl |
| S/R | $CH_2-CH_2$ | Ph | $CH_3$ | 2'-methoxybiphenyl |
| S/R | $CH_2-CH_2$ | 3,5-diCl-Ph | $CH_3$ | 2'-methoxybiphenyl |
| S/R | $CH_2-CH_2$ | Ph | $CH_3$ | 4'-fluorobiphenyl |
| S/R | $CH_2-CH_2$ | 3,5-diCl-Ph | H | 4'-fluorobiphenyl |
| S/R | $CH_2CH_2$ | 3,5-diCl-Ph | H | 2'-$CF_3$O-biphenyl |
| S/R | $CH_2-CH_2$ | 3,5-diCl-Ph | $CH_3$ | 2'-$CF_3$O-biphenyl |

| 2/3* | A-B | R¹ | R² | R⁸ |
|---|---|---|---|---|
| S/R | CH₂—CH₂ | 3,5-diCl-Ph | CH₃ | 3'-methoxybiphenyl |
| S/R | CH₂—CH₂ | 3,5-diCl-Ph | H | 3'-methoxybiphenyl |
| S/R | CH₂—CH₂ | 3,5-diCl-Ph | CH₃ | 2'-methoxy-3'-F-biphenyl |
| S/R | CH₂—CH₂ | 3,5-diCl-Ph | H | 2'-methoxy-3'-F-biphenyl |
| S/R | CH₂—CH₂ | 3,5-diCl-Ph | CH₃ | 3'-methoxy-2'-F-biphenyl |
| S/R | CH₂—CH₂ | 3,5-diCl-Ph | H | 3'-methoxy-2'-F-biphenyl |
| S/R | CH₂—CH₂ | 3,5-diCl-Ph | CH₃ | 2'-methoxy-5'-F-biphenyl |
| S/R | CH₂—CH₂ | 3,5-diCl-Ph | H | 2'-methoxy-5'-F-biphenyl |
| S/R | CH₂—CH₂ | 3,5-diCl-Ph | CH₃ | 3'-methoxy-5'-F-biphenyl |
| S/R | CH₂—CH₂ | 3,5-diCl-Ph | H | 3'-methoxy-5'-F-biphenyl |
| S/R | CH₂—CH₂ | 3,5-diCl-Ph | CH₃ | 2'-methoxy-6'-F-biphenyl |
| S/R | CH₂—CH₂ | 3,5-diCl-Ph | H | 2'-methoxy-6'-F-biphenyl |
| S/R | CH₂—CH₂ | 3-Cl-Ph | CH₃ | 2'-methoxybiphenyl |
| S/R | CH₂—CH₂ | 3,5-diCl-Ph | CH₃ | 4-methoxyphenyl |
| S/R | CH₂—CH₂ | 3,5-diCl-Ph | H | 4-methoxyphenyl |
| S/R | CH₂—CH₂ | 3,5-diCl-Ph | CH₃ | 2'-CF₃O-4'-F-biphenyl |
| S/R | CH₂—CH₂ | 3,5-diCl-Ph | H | 2'-CF₃O-4'-F-biphenyl |
| S/R | CH₂—CH₂ | 3,5-diCl-Ph | H | 2'-methoxy-4'-F-biphenyl |
| S/R | CH₂—CH₂ | 3,5-diCl-Ph | CH₃ | 4-hydroxyphenyl |
| S/R | CH₂—CH₂ | 3,5-diCl-Ph | CH₃ | 4-(3'-pyridyl)phenyl |
| S/R | CH₂—CH₂ | 3,5-diCl-Ph | H | 4-(N-pyrrolidinyl-carbonyl)oxyphenyl |
| S/R | CH₂—CH₂ | 3,5-diCl-Ph | H | 3-(N-pyrrolidinyl-carbonyl)oxyphenyl |
| S/R | CH₂—CH₂ | 3,5-diCl-Ph | H | 4-(2-methoxyethoxy)-phenyl |
| S/R | CH₂—CH₂ | 3,5-diCl-Ph | CH₃ | 4-(2-methoxyethoxy)-phenyl |
| S/R | CH₂—CH₂ | 3,5-diCl-Ph | H | 2'-cyanophenoxy-phenyl |
| S/R | CH₂—CH₂ | 3,5-diCl-Ph | H | 3-(2'-methoxyphenyl)-phenyl |
| S/R | CH₂—CH₂ | 3,5-diCl-Ph | CH₃ | 4-pyridyl |
| S/R | CH₂—CH₂ | 3,5-diCl-Ph | CH₃ | 4-pyridyl |
| S/R | CH₂—CH₂ | 3,5-diCl-Ph | CH₃ | 3-quinolyl |
| S/R | CH₂—CH₂ | 3,5-diCl-Ph | H | 4-(2-pyridyl)phenyl |
| S/R | CH₂—CH₂ | 3,5-diCl-Ph | CH₃ | 4-(2-oxo-3-pyridyl)-phenyl |
| S/R | CH₂—CH₂ | 3,5-diCl-Ph | H | 4-(2-oxo-3-pyridyl)-phenyl |
| S/R | CH₂—CH₂ | 3,5-diCl-Ph | CH₃ | 4-(2-methoxy-3-pyridyl)phenyl |
| S/R | CH₂—CH₂ | 3,5-diCl-Ph | H | 4-(2'-cyclopropoxy)-biphenyl |
| S/R | CH₂—CH₂ | 3,5-diCl-Ph | CH₃ | 4-(2'-cyclopropoxy)-biphenyl |
| S/R | CH₂—CH₂ | 3,5-diCl-Ph | H | 4-CF₃O-phenyl |
| S/R | CH₂—CH₂ | 3,5-diCl-Ph | H | 2-fluorophenyl |
| S/R | CH₂ | 3,5-diCl-Ph | H | 4-methoxyphenyl |
| S/R | CH₂ | 3,5-diCl-Ph | H | phenyl |
| S/R | CH₂—CH₂ | Ph | CH₃ | 2',6'-dimethoxy-biphenyl |
| S/R | CH₂—CH₂ | 3,5-diCl-Ph | H | 2',6'-dimethoxy-biphenyl |
| S/R | CH₂—CH₂ | 3,5-diCl-Ph | CH₃ | 2',6'-dimethoxy-biphenyl |
| S/R | CH₂ | 3,5-diCl-Ph | H | 2',6'-dimethoxy-biphenyl |
| S/R | CH₂ | 3,5-diCl-Ph | H | 2'-methoxybiphenyl |
| S/R | CH₂—CH₂ | 3,5-diCl-Ph | H | 2',5'-dimethoxy-biphenyl |
| S/R | CH₂—CH₂ | 3,5-diCl-Ph | CH₃ | 2',5'-dimethoxy-biphenyl |
| S/R | CH₂—CH₂ | 3,5-diCl-Ph | CH₃ | 2'-CF₃O-6'-methoxy-biphenyl |
| S/R | CH₂ | 3,5-diCl-Ph | CH₃ | 2'-CF₃O-6'-methoxy-biphenyl |
| S/R | CH₂ | 3,5-diCl-Ph | H | 2'-fluoro-4',6'-dimethoxybiphenyl |
| S/R | CH₂—CH₂ | 3,5-diCl-Ph | CH₃ | 2'-fluoro-4',6'-dimethoxybiphenyl |
| S/R | CH₂—CH₂ | 3,5-diCl-Ph | CH₃ | 2',6'-dimethoxy-3'-fluorobiphenyl |
| S/R | CH₂—CH₂ | 3,5-diCl-Ph | H | 2',6'-dimethoxy-3'-fluorobiphenyl |
| S/R | CH₂ | 3,5-diCl-Ph | H | 2',6'-dimethoxy-3'-fluorobiphenyl |
| S/R | CH₂—CH₂ | 3,5-diCl-Ph | CH₃ | 2',6'-dimethoxy-3',5'-difluorobiphenyl |
| S/R | CH₂O | 3,5-diCl-Ph | H | 2'-methoxybiphenyl |
| S/R | CH₂—CH₂ | 3,5-diCl-Ph | H | 4-(2'-thiazolyl)phenyl |
| S/R | CH₂O | 3,5-diCl-Ph | H | 2',6'-dimethoxy-biphenyl |
| S/R | CH₂O | 3,5-diCl-Ph | H | phenyl |
| S/R | CH₂O | 3,5-diCl-Ph | H | 4-methoxyphenyl |
| S/R | CH₂O | 3,5-diCl-Ph | CH₃ | 2',6'-dimethoxy-biphenyl |
| S/R | CH₂O | 3,5-diCl-Ph | CH₃ | 2'-methoxybiphenyl |
| S/R | CH₂O | Ph | CH₃ | 2',6'-dimethoxy-biphenyl |
| S/R | CH₂ | 2-thiophene | H | phenyl |
| R/R | CH₂S | 3,5-diCl-Ph | H | phenyl |
| S/R | CH₂S | 3,5-diCl-Ph | H | phenyl |
| S/R | CH₂CH₂ (3-Me)** | 3,5-diCl-Ph | H | phenyl |
| S/R | CH₂—CH₂ | Ph | H | 2'-cyclopropoxy-biphenyl |
| S/R | CH₂—CH₂ | 3-CF3-Ph | H | 2'-cyclopropoxy-biphenyl |
| S/R | CH₂ | 3-Cl-Ph | H | 2'-cyclopropoxy-biphenyl |
| S/R | CH₂—CF₂ | Ph | H | 2'-cyclopropoxy-biphenyl |
| S/R | CH₂ | 3,5-diCl-Ph | H | 2',6'-dicyclopropoxy-biphenyl |
| S/R | CH₂ | 3,5-diCl-Ph | H | 2'-cyclopropoxy-6'-fluorobiphenyl |
| S/R | CH₂ | 3-Cl-Ph | H | 2'-cyclopropoxy-6'-fluorobiphenyl |
| S/R | CH₂ | 2-thiophene | H | 2'-cyclopropoxy-6'-fluorobiphenyl |
| S/R | CH₂ | 3-F-Ph | H | 2',6'-dimethoxy-biphenyl |
| S/R | CH₂ | 2-thiophene | H | 2',6'-dimethoxy-biphenyl |
| S/R | CH₂ | 3,5-diMe-isoxazole | H | 2',6'-dimethoxy-biphenyl |
| S/R | CH₂ | 3,5-diCl-Ph | H | 4-ethoxyphenyl |
| S/R | CH₂—CH₂ | 3,5-diCl-Ph | H | 4-cyclopentoxyphenyl |
| S/R | CH₂ | 3,5-diCl-Ph | H | 4-(2,2,2-trifluoro-ethoxy)phenyl |
| S/R | CH₂ | 3,5-diCl-Ph | H | 4-(fluoromethoxy)-phenyl |
| S/R | CH₂ | 3,5-diCl-Ph | H | 4-(3-tetrahydrofuryl-oxy)phenyl |
| S/R | CH₂—CH₂ | 3,5-diCl-Ph | H | 4-(cyclopropoxy)-phenyl |
| S/R | CH₂ | 3,5-diCl-Ph | H | 4-(difluoromethoxy)-phenyl |

-continued

| 2/3* | A-B | R¹ | R² | R⁸ |
|---|---|---|---|---|
| S/R | $CH_2$ | 3,5-diCl-Ph | H | 6-methoxy-3-pyridyl |
| S/R | $CH_2-CH_2$ | 3,5-diCl-Ph | H | 3-benzyl-1,2,4-oxadiazol-5-yl |
| S/R | $CH_2-CH_2$ | 3,5-diCl-Ph | H | 3-(2'-fluorobenzyl)-1,2,4-oxadiazol-5-yl |
| S/R | $CH_2-CH_2$ | 3,5-diCl-Ph | H | 3-(2'-methoxybenzyl)-1,2,4-oxadiazol-5-yl |
| S/R | $CH_2$ | 3,5-diCl-Ph | $CH_3$ | 2',6'-dimethoxy-biphenyl |
| R/R | $CH_2$ | 3,5-diCl-Ph | $CH_3$ | 2',6'-dimethoxy-biphenyl |

-continued

| 2/3* | A-B | R¹ | R² | R⁸ |
|---|---|---|---|---|
| S/R | $CH_2$ | 3,5-diCl-Ph | $CH_3$ | 4-methoxyphenyl |
| R/R | $CH_2$ | 3,5-diCl-Ph | $CH_3$ | 4-methoxyphenyl |
| S/R | $CH_2-CH_2$ | 3,5-diCl-Ph | H | 4-(5'-t-butyl-2-thiazolyl)phenyl |

*Stereoconfiguration at the indicated positions
**ring is 3-methylpyrrolidine

\* \* \* \* \*

UNITED STATES PATENT AND TRADEMARK OFFICE
CERTIFICATE OF CORRECTION

PATENT NO. : 6,645,939 B1  Page 1 of 1
DATED : November 11, 2003
INVENTOR(S) : Philippe L. Durette et al.

It is certified that error appears in the above-identified patent and that said Letters Patent is hereby corrected as shown below:

Column 81,
Line 56, should read -- halogen, CN,$OR^d$, $O(CO)R^d$, $C_{1-5}$ alkyl optionally sub- --.
Line 60, should read -- 1) halogen, --.

Column 83,
Lines 32–40 should be omitted.

Signed and Sealed this

Twenty-fifth Day of May, 2004

JON W. DUDAS
*Acting Director of the United States Patent and Trademark Office*

SEQUENCE LISTING

```
<160> NUMBER OF SEQ ID NOS: 4

<210> SEQ ID NO 1
<211> LENGTH: 13
<212> TYPE: PRT
<213> ORGANISM: Homo sapiens

<400> SEQUENCE: 1

Cys Leu His Gly Pro Glu Ile Leu Asp Val Pro Ser Thr
1               5                   10

<210> SEQ ID NO 2
<211> LENGTH: 46
<212> TYPE: DNA
<213> ORGANISM: Homo sapiens

<400> SEQUENCE: 2
aattataatt tgatcaactt acctgtcaat tcttttacag cctgcc            46

<210> SEQ ID NO 3
<211> LENGTH: 40
<212> TYPE: DNA
<213> ORGANISM: Homo sapiens

<400> SEQUENCE: 3
ataggaattc cagctgccac catgcctggg aagatggtcg                   40

<210> SEQ ID NO 4
<211> LENGTH: 214
<212> TYPE: PRT
<213> ORGANISM: Homo sapien

<400> SEQUENCE: 4

Met Pro Gly Lys Met Val Val Ile Leu Gly Ala Ser Asn Ile Leu Trp
1               5                   10                  15

Ile Met Phe Ala Ala Ser Gln Ala Phe Lys Ile Glu Thr Thr Pro Glu
                20                  25                  30

Ser Arg Tyr Leu Ala Ile Gly Asp Ser Val Ser Leu Thr Cys Ser Thr
            35                  40                  45

Thr Gly Cys Glu Ser Pro Phe Phe Ser Trp Arg Thr Gln Ile Asp Ser
        50                  55                  60

Pro Leu Asn Gly Lys Val Thr Asn Glu Gly Thr Thr Ser Thr Leu Thr
65                  70                  75                  80
```

```
Met Asn Pro Val Ser Phe Gly Asn Glu His Ser Tyr Leu Cys Thr Ala
            85              90                  95
Thr Cys Glu Ser Arg Lys Leu Glu Lys Gly Ile Gln Val Glu Ile Tyr
            100             105                 110
Ser Phe Pro Lys Asp Pro Glu Ile His Leu Ser Gly Pro Leu Glu Ala
            115             120                 125
Gly Lys Pro Ile Thr Val Lys Cys Ser Val Ala Asp Val Tyr Pro Asp
    130             135             140
Arg Leu Glu Ile Asp Leu Leu Lys Gly Asp His Leu Met Asp Ser Gln
145             150              155              160
Glu Phe Leu Glu Asp Ala Asp Arg Lys Ser Leu Glu Thr Lys Ser Leu
            165             170              175
Glu Thr Phe Thr Pro Val Ile Glu Asp Ile Gly Lys Val Leu Val Cys
            180             185              190
Arg Ala Lys Leu His Ile Asp Glu Met Asp Ser Val Pro Thr Val Arg
    195             200              205
Gln Ala Val Lys Glu Leu
    210
```